United States Patent [19]
Broomfield et al.

[11] Patent Number: 6,001,625
[45] Date of Patent: *Dec. 14, 1999

[54] SITE-DIRECTED MUTAGENESIS OF ESTERASES

[75] Inventors: Clarence A. Broomfield, Jarrettsville; Charles B. Millard, Edgewood, both of Md.; Oksana Lockridge, Bellevue, Nebr.

[73] Assignee: The United States of America as represented by the Secretary of the Army, Washington, D.C.

[*] Notice: This patent is subject to a terminal disclaimer.

[21] Appl. No.: 08/446,100

[22] Filed: May 19, 1995

[51] Int. Cl.$^6$ .............................. C12N 9/18; C12N 15/09; C12N 15/55; A62D 3/00
[52] U.S. Cl. ........................ 435/197; 435/262.5; 435/440
[58] Field of Search ................................. 435/172.3, 197, 435/172.1, 262.5, 440

[56] References Cited

U.S. PATENT DOCUMENTS 5,312,743  5/1994  Schumacher et al. ............... 435/172.3

OTHER PUBLICATIONS

G. Gibney et al., "Mutagenesis of Essential Functional Residues in Acetylcholinesterase", Proc. Natl. Acad. Sci. 87: 7546–7550, Oct. 1990.

*Primary Examiner*—Rebecca E. Prouty
*Attorney, Agent, or Firm*—Charles H. Harris; John Francis Moran

[57] ABSTRACT

A method of modifying esterases by substitution with histadine of at least one amino acid within 6 Å of an active site serine provides esterases useful for detoxifying organophasphates.

10 Claims, No Drawings

SITE-DIRECTED MUTAGENESIS OF ESTERASES

FIELD OF THE INVENTION

This invention relates to use of organophosphorus acid anhydride (OPAA) hydrolyzing enzymes to detoxify organophosphates (OP) using site directed mutagenesis of esterases that strongly bind OP compounds, including acetylcholinesterases, butyrylcholinesterases, carboxylesterases and lipases.

BACKGROUND OF THE INVENTION

Poisoning with organophosphates presents a problem for agricultural workers that must be exposed to some agricultural chemicals and to military personnel exposed to chemicals used in chemical warfare. Furthermore the stock-piling of organophosphates has resulted in need to find ways to detoxify such stocks, including decontamination of land where OP's have been stored.

Present treatment for poisoning by organophosphates (OP) consists of a combination of drugs such as carbamates (e.g., pyridostigmine), anti-muscarinic (e.g., atropine), and reactivators (e.g., 2-[hydroxyiminomethyl]-1-methylpyridinium chloride, pralidoxime chloride) administered in post-exposure modalities. Although this drug regimen is effective in protecting experimental animals against lethality by OP poisoning, it is not effective in preventing convulsions, performance deficits, or permanent brain damage. To alleviate these post-exposure symptoms, the use of cholinesterases (ChEs) as a pretreatment drug was successfully tested in animals including non-human primates for the sequestration of highly toxic OP anti-ChEs before they reach their physiological targets. For example, pretreatment of rhesus monkeys with FBS AChE or horse serum butyrylcholinesterase protected them against a challenge up to 5 $LD_{50}$ of O-pinacolyl methylphosphonofluoridate (soman), a highly toxic OP. These monkeys pretreated with FBS AChE were devoid of any behavioral incapacitation after soman challenge, as measured by the serial probe recognition task or the primate equilibrium platform performance task. In vivo and in vitro titration of ChEs with a variety of OPs produce a 1:1 stoichiometry between organophosphate inhibited enzymes and the cumulative dose of the toxic nerve agent. These results substantiated the hypothesis that exogenously administered ChEs can effectively sequester in vivo OPs before they reach their physiological targets.

Although the use of cholinesterases as a single pretreatment drug for highly potent OPs is sufficient to provide complete protection without the need for postexposure treatment, its practical use at the present time may be limited. Large quantities of enzymes will be required to provide sufficient protection due to 1:1 stoichiometry (i.e., a single turnover) between OP and enzyme required to provide protection.

Various approaches have been considered for improving the efficacy of ChEs as pretreatment drugs. First, production of catalytic antibodies that hydrolyze OPs has been attempted. The second approach is the use of hydrolytic enzymes such as OP hydrolases. Parathion hydrolase from bacteria was shown to hydrolyze tabun with a sufficient rate to be useful as a pretreatment drug but it has a very short half-life in mice, but did provide protection from soman at dosage of 2 $LD_{50}$.

SUMMARY OF THE INVENTION

It is a purpose of this invention to provide improved means for detoxifying organophosphates by use of mutant esterases. In a preferred embodiment a butyrylcholinesterase which is particularly effective in detoxifying sites contaminated with OP's is exemplified. A human butyrylcholinesterase in which the glycine residue at the 117 position is substituted by histidine (identified as G117H) was particularly resistent to inactivation by OPAA and particularly effective for use in detoxification of organophosphorus anti-cholinesterase compounds. The method of detoxifying an organophosphate consists of (1) modifying an esterase by substitution with histadine of at least one amino acid within 6 angstrom units (A) of an active site serine and (2) contacting the organophosphate with a composition containing at least one of the esterases produced by step (1).

DETAILED DESCRIPTION OF THE INVENTION

It is the purpose of this invention to produce organophosporus acid anhydride (OPAA) hydrolyzing enzyme by site-directed mutagenesis of esterases that are stongly inhibited by OPAA compounds, including acetylcholinesterases, butyrylcholinesterases, and lipases. One example of such an esterase is the butyrylchoninesterase mutant identified as G117H wherein a glycine residue at position 117 is substituted by histidine. This mutant has been shown to be particularly effective for catalyzing the hydrolysis of sarin (isopropyl methylphosphonofluoridate, DFP (diisopropyl phosphorofluoridate), VX (o-ethyl-S-[2-bis(methylethyl) aminoethyl] methylphosphonothioate and Echothiophate. Furthermore, G117H was shown to be highly resistant to inhibition by organophosphorus inhibitors while maintaining its ability to catalyze the hydrolysis of normal substrates such as acetylcholine, butyrylcholine, acetylthiocholine, butyrylthiocholine, 4-nitophenyacetate and benzoylcholine.

The mutant enzymes present several advantages over the naturally-occurring OPAA hydrolyzing enzymes, showing increased efficiency. For example, G117H is able to catalyze the hydrolysis of VX at 25° C., pH 7.5 with turnover number of $5\times10^{-4}$ per second, which represents more than 350 fold increase over spontaneous hydrolysis under the same conditions. None of the naturally occurring OPAA hydrolases catalyze the hydrolysis of VX.

The mutants were prepared by site-directed mutagenesis using a conventional oligonucleotide directed in vitro mutagenesis system described by Eckstein and co-workers in Nucleic Acids Research 13, 8749–8785 (1985). Other conventional PCR techniques known in the art may be used. The selection of residues for replacement was based on a molecular model, using the crystal structure of AcChE published by Sussman, et al. on an Evans and Sutherland PS390 platform with Biosym software. This is really the critical factor; once the appropriate residue has been identified the mutagenesis is quite straightforward.

The nature of the residue being displaced is irrelevant so long as it is not critical for the maintenance of the structure of the protein. The important factor is the position of the substituted residue with respect to the active site serine. Usually the preferred substitution involves replacement of at least one amino acid with a histidine. We know that substitution at most other sites would have no effect at all, unless it disrupted the structure of the protein.

The cholinesterases of the invention can be produced in accord with the teachings of Fischer, U.S. Pat. No. 5,248,604, which is incorporated herein by reference in its entirety.

The butyryl cholinesterase and acetylcholinesterase have been modified extensively in the manner described.

Human Butyrylcholinesterase - Wild Type (unmutated)

MHSKVTIICIRFLFWFLLLCMLIGKSHTEDDIIIATKNGKVRGMNLTVFGGTVTAFLGIPYAQ    (Seq. #1)
PPLGRLRFKKPQSLTKWSDIWNATKYANSCCQNIDQSFPGFHGSEMWNPNTDLSEDCLYLNVW
IPAPKPKNATVLIWIYGGGFQTGTSSLHVYDGKFLARVERVIVVSMNYRVGALGFLALPGNPE
APGNMGLFDQQLALQWVQKNIAAFGGNPKSVTLFGESAGAASVSLHLLSPGSHSLFTRAILQS
GSFNAPWAVTSLYEARNRTLNLAKLTGCSRENETEIIKCLRNKDPQEILLNEAFVVPYGTPLS
VNFGPTVDGDFLTDMPDILLELGQFKKTQILVGVNKDEGTAFLVYGAPGFSKDNNSIITRKEF
QEGLKIFFPGVSEFGKESILFHYTDWVDDQRPENYREALGDVVGDYNFICPALEFTKKFSEWG
NNAFFYYFEHRSSKLPWPEWMGVMHGYEIEFVFGLPLERRDNYTKAEEILSRSIVKRWANFAK
YGNPNETQNNSTSWPVFKSTEQKYLTLNTESTRIMTKLRAQQCRFWTSFFPKVLEMTGNIDEA
EWEWKAGFHRWNNYMMDWKNQFNDYTSKKESCVGL

Human BuChE G117-->H

MHSKVTIICIRFLFWFLLLCMLIGKSHTEDDIIIATKNGKVRGMNLTVFGGTVTAFLGIPYAQ    (Seq #2)
PPLGRLRFKKPQSLTKWSDIWNATKYANSCCQNIDQSFPGFHGSEMWNPNTDLSEDCLYLNVW
IPAPKPKNATVLIWIYGGHFQTGTSSLHVYDGKFLARVERVIVVSMNYRVGALGFLALPGNPE

APGNMGLFDQQLALQWVQKNIAAFGGNPKSVTLFGESAGAASVSLHLLSPGSHSLFTRAILQS

GSFNAPWAVTSLYEARNRTLNLAKLTGCSRENETEIIKCLRNKDPQEILLNEAFVVPYGTPLS

VNFGPTVDGDFLTDMPDILLELGQFKKTQILVGVNKDEGTAFLVYGAPGFSKDNNSIITRKEF

QEGLKIFFPGVSEFGKESILFHYTDWVDDQRPENYREALGDVVGDYNFICPALEFTKKFSEWG

NNAFFYYFEHRSSKLPWPEWMGVMHGYEIEFVFGLPLERRDNYTKAEEILSRSIVKRWANFAK

YGNPNETQNNSTSWPVFKSTEQKYLTLNTESTRIMTKLRAQQCRFWTSFFPKVLEMTGNIDEA

EWEWKAGFHRWNNYMMDWKNQFNDYTSKKESCVGL

Human BuChE L286-->H

MHSKVTIICIRFLFWFLLLCMLIGKSHTEDDIIIATKNGKVRGMNLTVFGGTVTAFLGIPYAQ (Seq. #3)

PPLGRLRFKKPQSLTKWSDIWNATKYANSCCQNIDQSFPGFHGSEMWNPNTDLSEDCLYLNVW

IPAPKPKNATVLIWIYGGGFQTGTSSLHVYDGKFLARVERVIVVSMNYRVGALGFLALPGNPE

APGNMGLFDQQLALQWVQKNIAAFGGNPKSVTLFGESAGAASVSLHLLSPGSHSLFTRAILQS

GSFNAPWAVTSLYEARNRTLNLAKLTGCSRENETEIIKCLRNKDPQEILLNEAFVVPYGTPHS

VNFGPTVDGDFLTDMPDILLELGQFKKTQILVGVNKDEGTAFLVYGAPGFSKDNNSIITRKEF

QEGLKIFFPGVSEFGKESILFHYTDWVDDQRPENYREALGDVVGDYNFICPALEFTKKFSEWG

NNAFFYYFEHRSSKLPWPEWMGVMHGYEIEFVFGLPLERRDNYTKAEEILSRSIVKRWANFAK

YGNPNETQNNSTSWPVFKSTEQKYLTLNTESTRIMTKLRAQQCRFWTSFFPKVLEMTGNIDEA

EWEWKAGFHRWNNYMMDWKNQFNDYTSKKESCVGL

Human BuChE L286-->H

MHSKVTIICIRFLFWFLLLCMLIGKSHTEDDIIIATKNGKVRGMNLTVFGGTVTAFLGIPYAQ (Seq. #4)

PPLGRLRFKKPQSLTKWSDIWNATKYANSCCQNIDQSFPGFHGSEMWNPNTDLSEDCLYLNVW

IPAPKPKNATVLIWIYGGGFQTGTSSLHVYDGKFLARVERVIVVSMNYRVGALGFLALPGNPE

APGNMGLFDQQLALQWVQKNIAAFGGNPKSVTLFGESAGAASVSLHLLSPGSHSLFTRAILQS

GSFNAPWAVTSLYEARNRTLNLAKLTGCSRENETEIIKCLRNKDPQEILLNEAFVVPYGTPHS

VNFGPTVDGDFLTDMPDILLELGQFKKTQILVGVNKDEGTAFLVYGAPGFSKDNNSIITRKEF

QEGLKIFFPGVSEFGKESILFHYTDWVDDQRPENYREALGDVVGDYNFICPALEFTKKFSEWG

NNAFFYYFEHRSSKLPWPEWMGVMHGYEIEFVFGLPLERRDNYTKAEEILSRSIVKRWANFAK

YGNPNETQNNSTSWPVFKSTEQKYLTLNTESTRIMTKLRAQQCRFWTSFFPKVLEMTGNIDEA

EWEWKAGFHRWNNYMMDWKNQFNDYTSKKESCVGL

Human BuChE V288--->H

MHSKVTIICIRFLFWFLLLCMLIGKSHTEDDIIIATKNGKVRGMNLTVFGGTVTAFLGIPYAQPP     (Seq. #5)

LGRLRFKKPQSLTKWSDIWNATKYANSCCQNIDQSFPGFHGSEMWNPNTDLSEDCLYLNVWIPAP

KPKNATVLIWIYGGGFQTGTSSLHVYDGKFLARVERVIVVSMNYRVGALGFLALPGNPEAPGNMG

LFDQQLALQWVQKNIAAFGGNPKSVTLFGESAGAASVSLHLLSPGSHSLFTRAILQSGSFNAPWA

VTSLYEARNRTLNLAKLTGCSRENETEIIKCLRNKDPQEILLNEAFVVPYGTPLSHNFGPTVDGD

FLTDMPDILLELGQFKKTQILVGVNKDEGTAFLVYGAPGFSKDNNSIITRKEFQEGLKIFFPGVS

EFGKESILFHYTDWVDDQRPENYREALGDVVGDYNFICPALEFTKKFSEWGNNAFFYYFEHRSSK

LPWPEWMGVMHGYEIEFVFGLPLERRDNYTKAEEILSRSIVKRWANFAKYGNPNETQNNSTSWPV

FKSTEQKYLTLNTESTRIMTKLRAQQCRFWTSFFPKVLEMTGNIDEAEWEWKAGFHRWNNYMMDW

KNQFNDYTSKKESCVGL

Human BuChE G117--->K

MHSKVTIICIRFLFWFLLLCMLIGKSHTEDDIIIATKNGKVRGMNLTVFGGTVTAFLGIPYAQ     (Seq. #6)

PPLGRLRFKKPQSLTKWSDIWNATKYANSCCQNIDQSFPGFHGSEMWNPNTDLSEDCLYLNVW

IPAPKPKNATVLIWIYGGKFQTGTSSLHVYDGKFLARVERVIVVSMNYRVGALGFLALPGNPE

APGNMGLFDQQLALQWVQKNIAAFGGNPKSVTLFGESAGAASVSLHLLSPGSHSLFTRAILQS

GSFNAPWAVTSLYEARNRTLNLAKLTGCSRENETEIIKCLRNKDPQEILLNEAFVVPYGTPLS

VNFGPTVDGDFLTDMPDILLELGQFKKTQILVGVNKDEGTAFLVYGAPGFSKDNNSIITRKEF

QEGLKIFFPGVSEFGKESILFHYTDWVDDQRPENYREALGDVVGDYNFICPALEFTKKFSEWG

NNAFFYYFEHRSSKLPWPEWMGVMHGYEIEFVFGLPLERRDNYTKAEEILSRSIVKRWANFAK

YGNPNETQNNSTSWPVFKSTEQKYLTLNTESTRIMTKLRAQQCRFWTSFFPKVLEMTGNIDEA

EWEWKAGFHRWNNYMMDWKNQFNDYTSKKESCVGL

Human BuChE G117-->C

MHSKVTIICIRFLFWFLLLCMLIGKSHTEDDIIIATKNGKVRGMNLTVFGGTVTAFLGIPYAQ (Seq. #7)

PPLGRLRFKKPQSLTKWSDIWNATKYANSCCQNIDQSFPGFHGSEMWNPNTDLSEDCLYLNVW

IPAPKPKNATVLIWIYGGCFQTGTSSLHVYDGKFLARVERVIVVSMNYRVGALGFLALPGNPE

APGNMGLFDQQLALQWVQKNIAAFGGNPKSVTLFGESAGAASVSLHLLSPGSHSLFTRAILQS

GSFNAPWAVTSLYEARNRTLNLAKLTGCSRENETEIIKCLRNKDPQEILLNEAFVVPYGTPLS

VNFGPTVDGDFLTDMPDILLELGQFKKTQILVGVNKDEGTAFLVYGAPGFSKDNNSIITRKEF

QEGLKIFFPGVSEFGKESILFHYTDWVDDQRPENYREALGDVVGDYNFICPALEFTKKFSEWG

NNAFFYYFEHRSSKLPWPEWMGVMHGYEIEFVFGLPLERRDNYTKAEEILSRSIVKRWANFAK

YGNPNETQNNSTSWPVFKSTEQKYLTLNTESTRIMTKLRAQQCRFWTSFFPKVLEMTGNIDEA

EWEWKAGFHRWNNYMMDWKNQFNDYTSKKESCVGL

Human BuChE G117-->H, Q119-->E

MHSKVTIICIRFLFWFLLLCMLIGKSHTEDDIIIATKNGKVRGMNLTVFGGTVTAFLGIPYAQ (Seq. #8)

PPLGRLRFKKPQSLTKWSDIWNATKYANSCCQNIDQSFPGFHGSEMWNPNTDLSEDCLYLNVW

IPAPKPKNATVLIWIYGGHFETGTSSLHVYDGKFLARVERVIVVSMNYRVGALGFLALPGNPE

APGNMGLFDQQLALQWVQKNIAAFGGNPKSVTLFGESAGAASVSLHLLSPGSHSLFTRAILQS

GSFNAPWAVTSLYEARNRTLNLAKLTGCSRENETEIIKCLRNKDPQEILLNEAFVVPYGTPLS

VNFGPTVDGDFLTDMPDILLELGQFKKTQILVGVNKDEGTAFLVYGAPGFSKDNNSIITRKEF

QEGLKIFFPGVSEFGKESILFHYTDWVDDQRPENYREALGDVVGDYNFICPALEFTKKFSEWG

NNAFFYYFEHRSSKLPWPEWMGVMHGYEIEFVFGLPLERRDNYTKAEEILSRSIVKRWANFAK

YGNPNETQNNSTSWPVFKSTEQKYLTLNTESTRIMTKLRAQQCRFWTSFFPKVLEMTGNIDEA

EWEWKAGFHRWNNYMMDWKNQFNDYTSKKESCVGL

Human BuChE L286-->H, F329-->D

MHSKVTIICIRFLFWFLLLCMLIGKSHTEDDIIIATKNGKVRGMNLTVFGGTVTAFLGIPYAQ (Seq. #9)

PPLGRLRFKKPQSLTKWSDIWNATKYANSCCQNIDQSFPGFHGSEMWNPNTDLSEDCLYLNVW

IPAPKPKNATVLIWIYGGGFQTGTSSLHVYDGKFLARVERVIVVSMNYRVGALGFLALPGNPE

APGNMGLFDQQLALQWVQKNIAAFGGNPKSVTLFGESAGAASVSLHLLSPGSHSLFTRAILQS

GSFNAPWAVTSLYEARNRTLNLAKLTGCSRENETEIIKCLRNKDPQEILLNEAFVVPYGTPHS

VNFGPTVDGDFLTDMPDILLELGQFKKTQILVGVNKDEGTADLVYGAPGFSKDNNSIITRKEF

QEGLKIFFPGVSEFGKESILFHYTDWVDDQRPENYREALGDVVGDYNFICPALEFTKKFSEWG

NNAFFYYFEHRSSKLPWPEWMGVMHGYEIEFVFGLPLERRDNYTKAEEILSRSIVKRWANFAK

YGNPNETQNNSTSWPVFKSTEQKYLTLNTESTRIMTKLRAQQCRFWTSFFPKVLEMTGNIDEA

EWEWKAGFHRWNNYMMDWKNQFNDYTSKKESCVGL

Human BuChE L286-->H, F329-->E

MHSKVTIICIRFLFWFLLLCMLIGKSHTEDDIIIATKNGKVRGMNLTVFGGTVTAFLGIPYAQ (Seq. #10)

PPLGRLRFKKPQSLTKWSDIWNATKYANSCCQNIDQSFPGFHGSEMWNPNTDLSEDCLYLNVW

IPAPKPKNATVLIWIYGGGFQTGTSSLHVYDGKFLARVERVIVVSMNYRVGALGFLALPGNPE

APGNMGLFDQQLALQWVQKNIAAFGGNPKSVTLFGESAGAASVSLHLLSPGSHSLFTRAILQS

GSFNAPWAVTSLYEARNRTLNLAKLTGCSRENETEIIKCLRNKDPQEILLNEAFVVPYGTPHS

VNFGPTVDGDFLTDMPDILLELGQFKKTQILVGVNKDEGTAELVYGAPGFSKDNNSIITRKEF

QEGLKIFFPGVSEFGKESILFHYTDWVDDQRPENYREALGDVVGDYNFICPALEFTKKFSEWG

NNAFFYYFEHRSSKLPWPEWMGVMHGYEIEFVFGLPLERRDNYTKAEEILSRSIVKRWANFAK

YGNPNETQNNSTSWPVFKSTEQKYLTLNTESTRIMTKLRAQQCRFWTSFFPKVLEMTGNIDEA

EWEWKAGFHRWNNYMMDWKNQFNDYTSKKESCVGL

Human BuChE V288-->H, G291-->E

MHSKVTIICIRFLFWFLLLCMLIGKSHTEDDIIIATKNGKVRGMNLTVFGGTVTAFLGIPYAQ (Seq. #11)

PPLGRLRFKKPQSLTKWSDIWNATKYANSCCQNIDQSFPGFHGSEMWNPNTDLSEDCLYLNVW

IPAPKPKNATVLIWIYGGGFQTGTSSLHVYDGKFLARVERVIVVSMNYRVGALGFLALPGNPE

APGNMGLFDQQLALQWVQKNIAAFGGNPKSVTLFGESAGAASVSLHLLSPGSHSLFTRAILQS

GSFNAPWAVTSLYEARNRTLNLAKLTGCSRENETEIIKCLRNKDPQEILLNEAFVVPYGTPLS

HNFEPTVDGDFLTDMPDILLELGQFKKTQILVGVNKDEGTAFLVYGAPGFSKDNNSIITRKEF

QEGLKIFFPGVSEFGKESILFHYTDWVDDQRPENYREALGDVVGDYNFICPALEFTKKFSEWG

NNAFFYYFEHRSSKLPWPEWMGVMHGYEIEFVFGLPLERRDNYTKAEEILSRSIVKRWANFAK

YGNPNETQNNSTSWPVFKSTEQKYLTLNTESTRIMTKLRAQQCRFWTSFFPKVLEMTGNIDEA

EWEWKAGFHRWNNYMMDWKNQFNDYTSKKESCVGL

-continued

Human BuChE V288-->H, G291-->D

MHSKVTIICIRFLFWFLLLCMLIGKSHTEDDIIIATKNGKVRGMNLTVFGGTVTAFLGIPYAQ (Seq. #12)
PPLGRLRFKKPQSLTKWSDIWNATKYANSCCQNIDQSFPGFHGSEMWNPNTDLSEDCLYLNVW
IPAPKPKNATVLIWIYGGGFQTGTSSLHVYDGKFLARVERVIVVSMNYRVGALGFLALPGNPE
APGNMGLFDQQLALQWVQKNIAAFGGNPKSVTLFGESAGAASVSLHLLSPGSHSLFTRAILQS
GSFNAPWAVTSLYEARNRTLNLAKLTGCSRENETEIIKCLRNKDPQEILLNEAFVVPYGTPLS
HNFDPTVDGDFLTDMPDILLELGQFKKTQILVGVNKDEGTAFLVYGAPGFSKDNNSIITRKEF
QEGLKIFFPGVSEFGKESILFHYTDWVDDQRPENYREALGDVVGDYNFICPALEFTKKFSEWG
NNAFFYYFEHRSSKLPWPEWMGVMHGYEIEFVFGLPLERRDNYTKAEEILSRSIVKRWANFAK
YGNPNETQNNSTSWPVFKSTEQKYLTLNTESTRIMTKLRAQQCRFWTSFFPKVLEMTGNIDEA
EWEWKAGFHRWNNYMMDWKNQFNDYTSKKESCVGL

Human BuChE H119-->H

MHSKVTIICIRFLFWFLLLCMLIGKSHTEDDIIIATKNGKVRGMNLTVFGGTVTAFLGIPYAQ (Seq #13)
PPLGRLRFKKPQSLTKWSDIWNATKYANSCCQNIDQSFPGFHGSEMWNPNTDLSEDCLYLNVW
IPAPKPKNATVLIWIYGGGFHTGTSSLHVYDGKFLARVERVIVVSMNYRVGALGFLALPGNPE
APGNMGLFDQQLALQWVQKNIAAFGGNPKSVTLFGESAGAASVSLHLLSPGSHSLFTRAILQS
GSFNAPWAVTSLYEARNRTLNLAKLTGCSRENETEIIKCLRNKDPQEILLNEAFVVPYGTPLS
VNFGPTVDGDFLTDMPDILLELGQFKKTQILVGVNKDEGTAFLVYGAPGFSKDNNSIITRKEF
QEGLKIFFPGVSEFGKESILFHYTDWVDDQRPENYREALGDVVGDYNFICPALEFTKKFSEWG
NNAFFYYFEHRSSKLPWPEWMGVMHGYEIEFVFGLPLERRDNYTKAEEILSRSIVKRWANFAK
YGNPNETQNNSTSWPVFKSTEQKYLTLNTESTRIMTKLRAQQCRFWTSFFPKVLEMTGNIDEA
EWEWKAGFHRWNNYMMDWKNQFNDYTSKKESCVGL

Human BuChE Q119-->H, V288-->E

MHSKVTIICIRFLFWFLLLCMLIGKSHTEDDIIIATKNGKVRGMNLTVFGGTVTAFLGIPYAQ (Seq #14)
PPLGRLRFKKPQSLTKWSDIWNATKYANSCCQNIDQSFPGFHGSEMWNPNTDLSEDCLYLNVW
IPAPKPKNATVLIWIYGGGFHTGTSSLHVYDGKFLARVERVIVVSMNYRVGALGFLALPGNPE
APGNMGLFDQQLALQWVQKNIAAFGGNPKSVTLFGESAGAASVSLHLLSPGSHSLFTRAILQS
GSFNAPWAVTSLYEARNRTLNLAKLTGCSRENETEIIKCLRNKDPQEILLNEAFVVPYGTPLS
ENFGPTVDGDFLTDMPDILLELGQFKKTQILVGVNKDEGTAFLVYGAPGFSKDNNSIITRKEF
QEGLKIFFPGVSEFGKESILFHYTDWVDDQRPENYREALGDVVGDYNFICPALEFTKKFSEWG
NNAFFYYFEHRSSKLPWPEWMGVMHGYEIEFVFGLPLERRDNYTKAEEILSRSIVKRWANFAK
YGNPNETQNNSTSWPVFKSTEQKYLTLNTESTRIMTKLRAQQCRFWTSFFPKVLEMTGNIDEA
EWEWKAGFHRWNNYMMDWKNQFNDYTSKKESCVGL

Human BuChE V288-->H, Q119-->D

MHSKVTIICIRFLFWFLLLCMLIGKSHTEDDIIIATKNGKVRGMNLTVFGGTVTAFLGIPYAQ (Seq #15)
PPLGRLRFKKPQSLTKWSDIWNATKYANSCCQNIDQSFPGFHGSEMWNPNTDLSEDCLYLNVW
IPAPKPKNATVLIWIYGGGFDTGTSSLHVYDGKFLARVERVIVVSMNYRVGALGFLALPGNPE
APGNMGLFDQQLALQWVQKNIAAFGGNPKSVTLFGESAGAASVSLHLLSPGSHSLFTRAILQS
GSFNAPWAVTSLYEARNRTLNLAKLTGCSRENETEIIKCLRNKDPQEILLNEAFVVPYGTPLS
HNFGPTVDGDFLTDMPDILLELGQFKKTQILVGVNKDEGTAFLVYGAPGFSKDNNSIITRKEF
QEGLKIFFPGVSEFGKESILFHYTDWVDDQRPENYREALGDVVGDYNFICPALEFTKKFSEWG

NNAFFYYFEHRSSKLPWPEWMGVMHGYEIEFVFGLPLERRDNYTKAEEILSRSIVKRWANFAK
YGNPNETQNNSTSWPVFKSTEQKYLTLNTESTRIMTKLRAQQCRFWTSFFPKVLEMTGNIDEA
EWEWKAGFHRWNNYMMDWKNQFNDYTSKKESCVGL

Human BuChE V288-->H, Q119-->E

MHSKVTIICIRFLFWFLLLCMLIGKSHTEDDIIIATKNGKVRGMNLTVFGGTVTAFLGIPYAQ  (Seq #16)
PPLGRLRFKKPQSLTKWSDIWNATKYANSCCQNIDQSFPGFHGSEMWNPNTDLSEDCLYLNVW
IPAPKPKNATVLIWIYGGGDTGTSSLHVYDGKFLARVERVIVVSMNYRVGALGFLALPGNPE
APGNMGLFDQQLALQWVQKNIAAFGGNPKSVTLFGESAGAASVSLHLLSPGSHSLFTRAILQS
GSFNAPWAVTSLYEARNRTLNLAKLTGCSRENETEIIKCLRNKDPQEILLNEAFVVPYGTPLS
HNFGPTVDGDFLTDMPDILLELGQFKKTQILVGVNKDEGTAFLVYGAPGFSKDNNSIITRKEF
QEGLKIFFPGVSEFGKESILFHYTDWVDDQRPENYREALGDVVGDYNFICPALEFTKKFSEWG
NNAFFYYFEHRSSKLPWPEWMGVMHGYEIEFVFGLPLERRDNYTKAEEILSRSIVKRWANFAK
YGNPNETQNNSTSWPVFKSTEQKYLTLNTESTRIMTKLRAQQCRFWTSFFPKVLEMTGNIDEA
EWEWKAGFHRWNNYMMDWKNQFNDYTSKKESCVGL

Human BuChE V288-->H, A277-->D

MHSKVTIICIRFLFWFLLLCMLIGKSHTEDDIIIATKNGKVRGMNLTVFGGTVTAFLGIPYAQ  (Seq. #17)
PPLGRLRFKKPQSLTKWSDIWNATKYANSCCQNIDQSFPGFHGSEMWNPNTDLSEDCLYLNVW
IPAPKPKNATVLIWIYGGGFQTGTSSLHVYDGKFLARVERVIVVSMNYRVGALGFLALPGNPE
APGNMGLFDQQLALQWVQKNIAAFGGNPKSVTLFGESAGAASVSLHLLSPGSHSLFTRAILQS
GSFNAPWAVTSLYEARNRTLNLAKLTGCSRENETEIIKCLRNKDPQEILLNEDFVVPYGTPLS
HNFGPTVDGDFLTDMPDILLELGQFKKTQILVGVNKDEGTAFLVYGAPGFSKDNNSIITRKEF
QEGLKIFFPGVSEFGKESILFHYTDWVDDQRPENYREALGDVVGDYNFICPALEFTKKFSEWG
NNAFFYYFEHRSSKLPWPEWMGVMHGYEIEFVFGLPLERRDNYTKAEEILSRSIVKRWANFAK
YGNPNETQNNSTSWPVFKSTEQKYLTLNTESTRIMTKLRAQQCRFWTSFFPKVLEMTGNIDEA
EWEWKAGFHRWNNYMMDWKNQFNDYTSKKESCVGL

Human BuChE V288-->H, A277-->E

MHSKVTIICIRFLFWFLLLCMLIGKSHTEDDIIIATKNGKVRGMNLTVFGGTVTAFLGIPYAQ (Seq. #18)
PPLGRLRFKKPQSLTKWSDIWNATKYANSCCQNIDQSFPGFHGSEMWNPNTDLSEDCLYLNVW
IPAPKPKNATVLIWIYGGGFQTGTSSLHVYDGKFLARVERVIVVSMNYRVGALGFLALPGNPE
APGNMGLFDQQLALQWVQKNIAAFGGNPKSVTLFGESAGAASVSLHLLSPGSHSLFTRAILQS
GSFNAPWAVTSLYEARNRTLNLAKLTGCSRENETEIIKCLRNKDPQEILLNEEFVVPYGTPLS
HNFGPTVDGDFLTDMPDILLELGQFKKTQILVGVNKDEGTAFLVYGAPGFSKDNNSIITRKEF
QEGLKIFFPGVSEFGKESILFHYTDWVDDQRPENYREALGDVVGDYNFICPALEFTKKFSEWG
NNAFFYYFEHRSSKLPWPEWMGVMHGYEIEFVFGLPLERRDNYTKAEEILSRSIVKRWANFAK
YGNPNETQNNSTSWPVFKSTEQKYLTLNTESTRIMTKLRAQQCRFWTSFFPKVLEMTGNIDEA
EWEWKAGFHRWNNYMMDWKNQFNDYTSKKESCVGL

The acetylcholinesterase was also mutated in similiar fashion.

Human Acetylcholinesterase (AChE; EC 3.1.1.7) Wildtype

MRPPQCLLHTPSLASPLLLLLLWLLGGGVGAEGREDAELLVTVRGGRLRGIRLKTPGGPVSAF (Seq. #19)
LGIPFAEPPMGPRRFLPPEPKQPWSGVVDATTFQSVCYQYVDTLYPGFEGTEMWNPNRELSED

-continued

CLYLNVWTPYPRPTSPTPVLVWIYGGGFYSGASSLDVYDGRFLVQAERTVLVSMNYRVGAFGF
LALPGSREAPGNVGLLDQRLALQWVQENVAAFGGDPTSVTLFGESAGAASVGMHLLSPPSRGL
FHRAVLQSGAPNGPWATVGMGEARRRATQLAHLVGCPPGGTGGNDTELVACLRTRPAQVLVNH
EWHVLPQESVFRFSFVPVVDGDFLSDTPEALINAGDFHGLQVLVGVVKDEGSYFLVYGAPGFS
KDNESLISRAEFLAGVRVGVPQVSDLAAEAVVLHYTDWLHPEDPARLREALSDVVGDHNVVCP
VAQLAGRLAAQGARVYAYVFEHRASTLSWPLWMGVPHGYEIEFIFGIPLDPSRNYTAEEKIFA
QRLMRYWANFARTGDPNEPRDPKAPQWPPYTAGAQQYVSLDLRPLEVRRGLRAQACAFWNRFL
PKLLSATDTLDEAERQWKAEFHRWSSYMVHWKNQFDHYSKQDRCSDL

Human AChE G121-->H

MRPPQCLLHTPSLASPLLLLLLWLLGGGVGAEGREDAELLVTVRGGRLRGIRLKTPGGPVSAF    (Seq. #20)
LGIPFAEPPMGPRRFLPPEPKQPWSGVVDATTFQSVCYQYVDTLYPGFEGTEMWNPNRELSED
CLYLNVWTPYPRPTSPTPVLVWIYGGHFYSGASSLDVYDGRFLVQAERTVLVSMNYRVGAFGF
LALPGSREAPGNVGLLDQRLALQWVQENVAAFGGDPTSVTLFGESAGAASVGMHLLSPPSRGL
FHRAVLQSGAPNGPWATVGMGEARRRATQLAHLVGCPPGGTGGNDTELVACLRTRPAQVLVNH
EWHVLPQESVFRFSFVPVVDGDFLSDTPEALINAGDFHGLQVLVGVVKDEGSYFLVYGAPGFS
KDNESLISRAEFLAGVRVGVPQVSDLAAEAVVLHYTDWLHPEDPARLREALSDVVGDHNVVCP
VAQLAGRLAAQGARVYAYVFEHRASTLSWPLWMGVPHGYEIEFIFGIPLDPSRNYTAEEKIFA
QRLMRYWANFARTGDPNEPRDPKAPQWPPYTAGAQQYVSLDLRPLEVRRGLRAQACAFWNRFL
PKLLSATDTLDEAERQWKAEFHRWSSYMVHWKNQFDHYSKQDRCSDL

Human AChE F290-->H

MRPPQCLLHTPSLASPLLLLLLWLLGGGVGAEGREDAELLVTVRGGRLRGIRLKTPGGPVSAF    (Seq. #21)
LGIPFAEPPMGPRRFLPPEPKQPWSGVVDATTFQSVCYQYVDTLYPGFEGTEMWNPNRELSED
CLYLNVWTPYPRPTSPTPVLVWIYGGGFYSGASSLDVYDGRFLVQAERTVLVSMNYRVGAFGF
LALPGSREAPGNVGLLDQRLALQWVQENVAAFGGDPTSVTLFGESAGAASVGMHLLSPPSRGL
FHRAVLQSGAPNGPWATVGMGEARRRATQLAHLVGCPPGGTGGNDTELVACLRTRPAQVLVNH
EWHVLPQESVHRFSFVPVVDGDFLSDTPEALINAGDFHGLQVLVGVVKDEGSYFLVYGAPGFS
KDNESLISRAEFLAGVRVGVPQVSDLAAEAVVLHYTDWLHPEDPARLREALSDVVGDHNVVCP
VAQLAGRLAAQGARVYAYVFEHRASTLSWPLWMGVPHGYEIEFIFGIPLDPSRNYTAEEKIFA
QRLMRYWANFARTGDPNEPRDPKAPQWPPYTAGAQQYVSLDLRPLEVRRGLRAQACAFWNRFL
PKLLSATDTLDEAERQWKAEFHRWSSYMVHWKNQFDHYSKQDRCSDL

Human AChE F290-->H, F333-->D

MRPPQCLLHTPSLASPLLLLLLWLLGGGVGAEGREDAELLVTVRGGRLRGIRLKTPGGPVSAF    (Seq #22)
LGIPFAEPPMGPRRFLPPEPKQPWSGVVDATTFQSVCYQYVDTLYPGFEGTEMWNPNRELSED
CLYLNVWTPYPRPTSPTPVLVWIYGGGFYSGASSLDVYDGRFLVQAERTVLVSMNYRVGAFGF
LALPGSREAPGNVGLLDQRLALQWVQENVAAFGGDPTSVTLFGESAGAASVGMHLLSPPSRGL
FHRAVLQSGAPNGPWATVGMGEARRRATQLAHLVGCPPGGTGGNDTELVACLRTRPAQVLVNH
EWHVLPQESVHRFSFVPVVDGDFLSDTPEALINAGDFHGLQVLVGVVKDEGSYDLVYGAPGFS
KDNESLISRAEFLAGVRVGVPQVSDLAAEAVVLHYTDWLHPEDPARLREALSDVVGDHNVVCP
VAQLAGRLAAQGARVYAYVFEHRASTLSWPLWMGVPHGYEIEFIFGIPLDPSRNYTAEEKIFA
QRLMRYWANFARTGDPNEPRDPKAPQWPPYTAGAQQYVSLDLRPLEVRRGLRAQACAFWNRFL

-continued

PKLLSATDTLDEAERQWKAEFHRWSSYMVHWKNQFDHYSKQDRCSDL

Human AChE F290-->H, F333-->E

MRPPQCLLHTPSLASPLLLLLLWLLGGGVGAEGREDAELLVTVRGGRLRGIRLKTPGGPVSAF  (Seq #23)
LGIPFAEPPMGPRRFLPPEPKQPWSGVVDATTFQSVCYQYVDTLYPGFEGTEMWNPNRELSED
CLYLNVWTPYPRPTSPTPVLVWIYGGGFYSGASSLDVYDGRFLVQAERTVLVSMNYRVGAFGF
LALPGSREAPGNVGLLDQRLALQWVQENVAAFGGDPTSVTLFGESAGAASVGMHLLSPPSRGL
FHRAVLQSGAPNGPWATVGMGEARRRATQLAHLVGCPPGGTGGNDTELVACLRTRPAQVLVNH
EWHVLPQESVHRFSFVPVVDGDFLSDTPEALINAGDFHGLQVLVGVVKDEGSYELVYGAPGFS
KDNESLISRAEFLAGVRVGVPQVSDLAAEAVVLHYTDWLHPEDPARLREALSDVVGDHNVVCP
VAQLAGRLAAQGARVYAYVFEHRASTLSWPLWMGVPHGYEIEFIFGIPLDPSRNYTAEEKIFA
QRLMRYWANFARTGDPNEPRDPKAPQWPPYTAGAQQYVSLDLRPLEVRRGLRAQACAFWNRFL
PKLLSATDTLDEAERQWKAEFHRWSSYMVHWKNQFDHYSKQDRCSDL

Human AChE Y123-->H

MRPPQCLLHTPSLASPLLLLLLWLLGGGVGAEGREDAELLVTVRGGRLRGIRLKTPGGPVSAF  (Seq. #24)
LGIPFAEPPMGPRRFLPPEPKQPWSGVVDATTFQSVCYQYVDTLYPGFEGTEMWNPNRELSED
CLYLNVWTPYPRPTSPTPVLVWIYGGGFYSGASSLDVYDGRFLVQAERTVLVSMNYRVGAFGF
LALPGSREAPGNVGLLDQRLALQWVQENVAAFGGDPTSVTLFGESAGAASVGMHLLSPPSRGL
FHRAVLQSGAPNGPWATVGMGEARRRATQLAHLVGCPPGGTGGNDTELVACLRTRPAQVLVNH
EWHVLPQESVFRHSFVPVVDGDFLSDTPEALINAGDFHGLQVLVGVVKDEGSYFLVYGAPGFS
KDNESLISRAEFLAGVRVGVPQVSDLAAEAVVLHYTDWLHPEDPARLREALSDVVGDHNVVCP
VAQLAGRLAAQGARVYAYVFEHRASTLSWPLWMGVPHGYEIEFIFGIPLDPSRNYTAEEKIFA
QRLMRYWANFARTGDPNEPRDPKAPQWPPYTAGAQQYVSLDLRPLEVRRGLRAQACAFWNRFL
PKLLSATDTLDEAERQWKAEFHRWSSYMVHWKNQFDHYSKQDRCSDL

Human AChE Y123-->H

MRPPQCLLHTPSLASPLLLLLLWLLGGGVGAEGREDAELLVTVRGGRLRGIRLKTPGGPVSAF  (Seq. #25)
LGIPFAEPPMGPRRFLPPEPKQPWSGVVDATTFQSVCYQYVDTLYPGFEGTEMWNPNRELSED
CLYLNVWTPYPRPTSPTPVLVWIYGGGFHSGASSLDVYDGRFLVQAERTVLVSMNYRVGAFGF
LALPGSREAPGNVGLLDQRLALQWVQENVAAFGGDPTSVTLFGESAGAASVGMHLLSPPSRGL
FHRAVLQSGAPNGPWATVGMGEARRRATQLAHLVGCPPGGTGGNDTELVACLRTRPAQVLVNH
EWHVLPQESVFRFSFVPVVDGDFLSDTPEALINAGDFHGLQVLVGVVKDEGSYFLVYGAPGFS
KDNESLISRAEFLAGVRVGVPQVSDLAAEAVVLHYTDWLHPEDPARLREALSDVVGDHNVVCP
VAQLAGRLAAQGARVYAYVFEHRASTLSWPLWMGVPHGYEIEFIFGIPLDPSRNYTAEEKIFA
QRLMRYWANFARTGDPNEPRDPKAPQWPPYTAGAQQYVSLDLRPLEVRRGLRAQACAFWNRFL
PKLLSATDTLDEAERQWKAEFHRWSSYMVHWKNQFDHYSKQDRCSDL

Carboxylesterase was also mutated.

Human Liver Carboxylesterase (CaE) Wildtype

EHCLYLNIYTPADLTKKNRLPVMVWIHGGGLMVGAASTYDGLALAAHENVVVVTIQYRLGIWG  (Seq #26)
FFSTGDEHSRGNWGHLDQVAALRWVQDNIASFGGNPGSVTIFGESAGGESVSVLVLSPLAKNL
FHRAISESGVALTSVLVKKGDVKPLAEQIAITAGCKTTTSAAMVHCLRQKTEEELLETTLKIG
NSYLWTYRETQRESTLLGTVIDGMLLLKTPEELQRERNFHTVPYMVGINKQEFGWLIPMQLMS
YPLSEGQLDQKTAMSLLGSPIPLFAIAKELIPEATEKYLGGTDDTVKKKDLILDLIADVMFGV

PSVIVARNHRDAGAPTYMYEFQYRPSFSSDMKPKTVIGDHGDELFSVFGAPFLKEGASEEEIR
LSKMVMKFWANFARNGNPNGKGLPHWPEYNQKEGYLQIGANTQAAQKLKDKEVAFWTNLFAKK
AVEKPPQTDHIEL

Human Liver Carboxylesterase (CaE) G30-->H

EHCLYLNIYTPADLTKKNRLPVMVWIHGGHLMVGAASTYDGLALAAHENVVVVTIQYRLGIWG  (Seq #27)
FFSTGDEHSRGNWGHLDQVAALRWVQDNIASFGGNPGSVTIFGESAGGESVSVLVLSPLAKNL
FHRAISESGVALTSVLVKKGDVKPLAEQIAITAGCKTTTSAAMVHCLRQKTEEELLETTLKIG
NSYLWTYRETQRESTLLGTVIDGMLLLKTPEELQRERNFHTVPYMVGINKQEFGWLIPMQLMS
YPLSEGQLDQKTAMSLLGSPIPLFAIAKELIPEATEKYLGGTDDTVKKKDLILDLIADVMFGV
PSVIVARNHRDAGAPTYMYEFQYRPSFSSDMKPKTVIGDHGDELFSVFGAPFLKEGASEEEIR
LSKMVMKFWANFARNGNPNGKGLPHWPEYNQKEGYLQIGANTQAAQKLKDKEVAFWTNLFAKK
AVEKPPQTDHIEL

Human CaE G30-->H, M32-->E

EHCLYLNIYTPADLTKKNRLPVMVWIHGGHLEVGAASTYDGLALAAHENVVVVTIQYRLGIWG  (Seq #28)
FFSTGDEHSRGNWGHLDQVAALRWVQDNIASFGGNPGSVTIFGESAGGESVSVLVLSPLAKNL
FHRAISESGVALTSVLVKKGDVKPLAEQIAITAGCKTTTSAAMVHCLRQKTEEELLETTLKIG
NSYLWTYRETQRESTLLGTVIDGMLLLKTPEELQRERNFHTVPYMVGINKQEFGWLIPMQLMS
YPLSEGQLDQKTAMSLLGSPIPLFAIAKELIPEATEKYLGGTDDTVKKKDLILDLIADVMFGV
PSVIVARNHRDAGAPTYMYEFQYRPSFSSDMKPKTVIGDHGDELFSVFGAPFLKEGASEEEIR
LSKMVMKFWANFARNGNPNGKGLPHWPEYNQKEGYLQIGANTQAAQKLKDKEVAFWTNLFAKK
AVEKPPQTDHIEL

Human CaE G30-->H, M32-->D

EHCLYLNIYTPADLTKKNRLPVMVWIHGGHLDVGAASTYDGLALAAHENVVVVTIQYRLGIWG  (Seq. #29)
FFSTGDEHSRGNWGHLDQVAALRWVQDNIASFGGNPGSVTIFGESAGGESVSVLVLSPLAKNL
FHRAISESGVALTSVLVKKGDVKPLAEQIAITAGCKTTTSAAMVHCLRQKTEEELLETTLKIG
NSYLWTYRETQRESTLLGTVIDGMLLLKTPEELQRERNFHTVPYMVGINKQEFGWLIPMQLMS
YPLSEGQLDQKTAMSLLGSPIPLFAIAKELIPEATEKYLGGTDDTVKKKDLILDLIADVMFGV
PSVIVARNHRDAGAPTYMYEFQYRPSFSSDMKPKTVIGDHGDELFSVFGAPFLKEGASEEEIR
LSKMVMKFWANFARNGNPNGKGLPHWPEYNQKEGYLQIGANTQAAQKLKDKEVAFWTNLFAKK
AVEKPPQTDHIEL

Human CaE E202-->H

EHCLYLNIYTPADLTKKNRLPVMVWIHGGGLMVGAASTYDGLALAAHENVVVVTIQYRLGIWG  (Seq. #30)
FFSTGDEHSRGNWGHLDQVAALRWVQDNIASFGGNPGSVTIFGESAGGESVSVLVLSPLAKNL
FHRAISESGVALTSVLVKKGDVKPLAEQIAITAGCKTTTSAAMVHCLRQKTEEELLETTLKIG
NSYLWTYRETQRHSTLLGTVIDGMLLLKTPEELQRERNFHTVPYMVGINKQEFGWLIPMQLMS
YPLSEGQLDQKTAMSLLGSPIPLFAIAKELIPEATEKYLGGTDDTVKKKDLILDLIADVMFGV
PSVIVARNHRDAGAPTYMYEFQYRPSFSSDMKPKTVIGDHGDELFSVFGAPFLKEGASEEEIR
LSKMVMKFWANFARNGNPNGKGLPHWPEYNQKEGYLQIGANTQAAQKLKDKEVAFWTNLFAKK
AVEKPPQTDHIEL

Human CaE T204-->H

-continued

```
EHCLYLNIYTPADLTKKNRLPVMVWIHGGGLMVGAASTYDGLALAAHENVVVVTIQYRLGIWG    (Seq #31)

FFSTGDEHSRGNWGHLDQVAALRWVQDNIASFGGNPGSVTIFGESAGGESVSVLVLSPLAKNL

FHRAISESGVALTSVLVKKGDVKPLAEQIAITAGCKTTTSAAMVHCLRQKTEEELLETTLKIG

NSYLWTYRETQRESHLLGTVIDGMLLLKTPEELQRERNFHTVPYMVGINKQEFGWLIPMQLMS

YPLSEGQLDQKTAMSLLGSPIPLFAIAKELIPEATEKYLGGTDDTVKKKDLILDLIADVMFGV

PSVIVARNHRDAGAPTYMYEFQYRPSFSSDMKPKTVIGDHGDELFSVFGAPFLKEGASEEEIR

LSKMVMKFWANFARNGNPNGKGLPHWPEYNQKEGYLQIGANTQAAQKLKDKEVAFWTNLFAKK

AVEKPPQTDHIEL
```

If the catalyst is to be used in vitro to destroy nerve agent stocks it could simply be stirred into an aqueous solution of the nerve agent and allowed to stand at ambient temperature for a time. For in vivo use as a pretreatment against nerve agent exposure it could be administered parenterally (for example, intravenously, subcutaneously or intramuscularly, or delivered via inhalation via a gene transfer vector. There is no need for an oxime with these mutants.

Kinetic data, both substrate hydrolysis and reaction with inhibitors for mutant BuChE G117H that compares the mutant with the wild type enzyme, is provided. Specifically, $K_m$ and $V_{max}$ for hydrolysis of benzoylcholine, acetylthiocholine, butyrylthiocholine and p-nitrophenyl acetate have been compared. Data also shows comparison of inhibition and reactivation rates for GA, GB, GD, VX, DFP, and Echothiophate using the G117H.

As indicated previously, the nature of the residue being displaced is irrelevant so long as it is not critical for the maintenance of the structure of the protein. The important factor is the position of the substituted residue with respect to the active site serine in the folded molecule.

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
      (A) LENGTH: 602 amino acids
      (B) TYPE: amino acid
      (C) STRANDEDNESS: single
      (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
      (A) ORGANISM: human esterases (xi) SEQUENCE DESCRIPTION: SEQ ID NO:1:

```
Met His Ser Lys Val Thr Ile Ile Cys Ile Arg Phe Leu Phe Trp Phe
1               5                   10                  15

Leu Leu Leu Cys Met Leu Ile Gly Lys Ser His Thr Glu Asp Asp Ile
                20                  25                  30

Ile Ile Ala Thr Lys Asn Gly Lys Val Arg Gly Met Asn Leu Thr Val
                35                  40                  45

Phe Gly Gly Thr Val Thr Ala Phe Leu Gly Ile Pro Tyr Ala Gln Pro
    50                  55                  60

Pro Leu Gly Arg Leu Arg Phe Lys Lys Pro Gln Ser Leu Thr Lys Trp
65                  70                  75                  80

Ser Asp Ile Trp Asn Ala Thr Lys Tyr Ala Asn Ser Cys Cys Gln Asn
                85                  90                  95
```

-continued

```
Ile Asp Gln Ser Phe Pro Gly Phe His Gly Ser Glu Met Trp Asn Pro
            100                 105                 110

Asn Thr Asp Leu Ser Glu Asp Cys Leu Tyr Leu Asn Val Trp Ile Pro
            115                 120                 125

Ala Pro Lys Pro Lys Asn Ala Thr Val Leu Ile Trp Ile Tyr Gly Gly
            130                 135                 140

Gly Phe Gln Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
                165                 170                 175

Gly Ala Leu Gly Phe Leu Ala Leu Pro Gly Asn Pro Glu Ala Pro Gly
                180                 185                 190

Asn Met Gly Leu Phe Asp Gln Gln Leu Ala Leu Gln Trp Val Gln Lys
            195                 200                 205

Asn Ile Ala Ala Phe Gly Gly Asn Pro Lys Ser Val Thr Leu Phe Gly
            210                 215                 220

Glu Ser Ala Gly Ala Ala Ser Val Ser Leu His Leu Leu Ser Pro Gly
225                 230                 235                 240

Ser His Ser Leu Phe Thr Arg Ala Ile Leu Gln Ser Gly Ser Phe Asn
                245                 250                 255

Ala Pro Trp Ala Val Thr Ser Leu Tyr Glu Ala Arg Asn Arg Thr Leu
            260                 265                 270

Asn Leu Ala Lys Leu Thr Gly Cys Ser Arg Glu Asn Glu Thr Glu Ile
            275                 280                 285

Ile Lys Cys Leu Arg Asn Lys Asp Pro Gln Glu Ile Leu Leu Asn Glu
            290                 295                 300

Ala Phe Val Val Pro Tyr Gly Thr Pro Leu Ser Val Asn Phe Gly Pro
305                 310                 315                 320

Thr Val Asp Gly Asp Phe Leu Thr Asp Met Pro Asp Ile Leu Leu Glu
                325                 330                 335

Leu Gly Gln Phe Lys Lys Thr Gln Ile Leu Val Gly Val Asn Lys Asp
            340                 345                 350

Glu Gly Thr Ala Phe Leu Val Tyr Gly Ala Pro Gly Phe Ser Lys Asp
            355                 360                 365

Asn Asn Ser Ile Ile Thr Arg Lys Glu Phe Gln Glu Gly Leu Lys Ile
            370                 375                 380

Phe Phe Pro Gly Val Ser Glu Phe Gly Lys Glu Ser Ile Leu Phe His
385                 390                 395                 400

Tyr Thr Asp Trp Val Asp Asp Gln Arg Pro Glu Asn Tyr Arg Glu Ala
                405                 410                 415

Leu Gly Asp Val Val Gly Asp Tyr Asn Phe Ile Cys Pro Ala Leu Glu
            420                 425                 430

Phe Thr Lys Lys Phe Ser Glu Trp Gly Asn Asn Ala Phe Phe Tyr Tyr
            435                 440                 445

Phe Glu His Arg Ser Ser Lys Leu Pro Trp Pro Glu Trp Met Gly Val
            450                 455                 460

Met His Gly Tyr Glu Ile Glu Phe Val Phe Gly Leu Pro Leu Glu Arg
465                 470                 475                 480

Arg Asp Asn Tyr Thr Lys Ala Glu Glu Ile Leu Ser Arg Ser Ile Val
                485                 490                 495

Lys Arg Trp Ala Asn Phe Ala Lys Tyr Gly Asn Pro Asn Glu Thr Gln
            500                 505                 510

Asn Asn Ser Thr Ser Trp Pro Val Phe Lys Ser Thr Glu Gln Lys Tyr
            515                 520                 525
```

```
Leu Thr Leu Asn Thr Glu Ser Thr Arg Ile Met Thr Lys Leu Arg Ala
        530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
            580                 585                 590

Thr Ser Lys Lys Glu Ser Cys Val Gly Leu
        595                 600
```

(2) INFORMATION FOR SEQ ID NO:2:

(i) SEQUENCE CHARACTERISTICS:
        (A) LENGTH: 602 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
       (A) ORGANISM: human esterases (xi) SEQUENCE DESCRIPTION: SEQ ID NO:2:

```
Met His Ser Lys Val Thr Ile Ile Cys Ile Arg Phe Leu Phe Trp Phe
1               5                   10                  15

Leu Leu Leu Cys Met Leu Ile Gly Lys Ser His Thr Glu Asp Asp Ile
            20                  25                  30

Ile Ile Ala Thr Lys Asn Gly Lys Val Arg Gly Met Asn Leu Thr Val
                35                  40                  45

Phe Gly Gly Thr Val Thr Ala Phe Leu Gly Ile Pro Tyr Ala Gln Pro
    50                  55                  60

Pro Leu Gly Arg Leu Arg Phe Lys Lys Pro Gln Ser Leu Thr Lys Trp
65                  70                  75                  80

Ser Asp Ile Trp Asn Ala Thr Lys Tyr Ala Asn Ser Cys Cys Gln Asn
                85                  90                  95

Ile Asp Gln Ser Phe Pro Gly Phe His Gly Ser Glu Met Trp Asn Pro
                100                 105                 110

Asn Thr Asp Leu Ser Glu Asp Cys Leu Tyr Leu Asn Val Trp Ile Pro
                115                 120                 125

Ala Pro Lys Pro Lys Asn Ala Thr Val Leu Ile Trp Ile Tyr Gly Gly
    130                 135                 140

His Phe Gln Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
                165                 170                 175

Gly Ala Leu Gly Phe Leu Ala Leu Pro Gly Asn Pro Glu Ala Pro Gly
            180                 185                 190

Asn Met Gly Leu Phe Asp Gln Gln Leu Ala Leu Gln Trp Val Gln Lys
        195                 200                 205

Asn Ile Ala Ala Phe Gly Gly Asn Pro Lys Ser Val Thr Leu Phe Gly
    210                 215                 220
```

```
Glu Ser Ala Gly Ala Ala Ser Val Ser Leu His Leu Ser Pro Gly
225                 230                 235                 240

Ser His Ser Leu Phe Thr Arg Ala Ile Leu Gln Ser Gly Ser Phe Asn
                245                 250                 255

Ala Pro Trp Ala Val Thr Ser Leu Tyr Glu Ala Arg Asn Arg Thr Leu
                260                 265                 270

Asn Leu Ala Lys Leu Thr Gly Cys Ser Arg Glu Asn Glu Thr Glu Ile
                275                 280                 285

Ile Lys Cys Leu Arg Asn Lys Asp Pro Gln Glu Ile Leu Leu Asn Glu
290                 295                 300

Ala Phe Val Val Pro Tyr Gly Thr Pro Leu Ser Val Asn Phe Gly Pro
305                 310                 315                 320

Thr Val Asp Gly Asp Phe Leu Thr Asp Met Pro Asp Ile Leu Leu Glu
                325                 330                 335

Leu Gly Gln Phe Lys Lys Thr Gln Ile Leu Val Gly Val Asn Lys Asp
                340                 345                 350

Glu Gly Thr Ala Phe Leu Val Tyr Gly Ala Pro Gly Phe Ser Lys Asp
                355                 360                 365

Asn Asn Ser Ile Ile Thr Arg Lys Glu Phe Gln Glu Gly Leu Lys Ile
370                 375                 380

Phe Phe Pro Gly Val Ser Glu Phe Gly Lys Glu Ser Ile Leu Phe His
385                 390                 395                 400

Tyr Thr Asp Trp Val Asp Asp Gln Arg Pro Glu Asn Tyr Arg Glu Ala
                405                 410                 415

Leu Gly Asp Val Val Gly Asp Tyr Asn Phe Ile Cys Pro Ala Leu Glu
                420                 425                 430

Phe Thr Lys Lys Phe Ser Glu Trp Gly Asn Asn Ala Phe Phe Tyr Tyr
                435                 440                 445

Phe Glu His Arg Ser Ser Lys Leu Pro Trp Pro Glu Trp Met Gly Val
                450                 455                 460

Met His Gly Tyr Glu Ile Glu Phe Val Phe Gly Leu Pro Leu Glu Arg
465                 470                 475                 480

Arg Asp Asn Tyr Thr Lys Ala Glu Glu Ile Leu Ser Arg Ser Ile Val
                485                 490                 495

Lys Arg Trp Ala Asn Phe Ala Lys Tyr Gly Asn Pro Asn Glu Thr Gln
                500                 505                 510

Asn Asn Ser Thr Ser Trp Pro Val Phe Lys Ser Thr Glu Gln Lys Tyr
                515                 520                 525

Leu Thr Leu Asn Thr Glu Ser Thr Arg Ile Met Thr Lys Leu Arg Ala
530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
                580                 585                 590

Thr Ser Lys Lys Glu Ser Cys Val Gly Leu
                595                 600
```

(2) INFORMATION FOR SEQ ID NO:3:

(i) SEQUENCE CHARACTERISTICS:
        (A) LENGTH: 602 amino acids
        (B) TYPE: amino acid
        (C) STRANDEDNESS: single (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
    (A) ORGANISM: human esterases (xi) SEQUENCE DESCRIPTION: SEQ ID NO:3:

```
Met His Ser Lys Val Thr Ile Ile Cys Ile Arg Phe Leu Phe Trp Phe
1               5                   10                  15

Leu Leu Leu Cys Met Leu Ile Gly Lys Ser His Thr Glu Asp Asp Ile
            20                  25                  30

Ile Ile Ala Thr Lys Asn Gly Lys Val Arg Gly Met Asn Leu Thr Val
        35                  40                  45

Phe Gly Gly Thr Val Thr Ala Phe Leu Gly Ile Pro Tyr Ala Gln Pro
    50                  55                  60

Pro Leu Gly Arg Leu Arg Phe Lys Lys Pro Gln Ser Leu Thr Lys Trp
65                  70                  75                  80

Ser Asp Ile Trp Asn Ala Thr Lys Tyr Ala Asn Ser Cys Cys Gln Asn
                85                  90                  95

Ile Asp Gln Ser Phe Pro Gly Phe His Gly Ser Glu Met Trp Asn Pro
            100                 105                 110

Asn Thr Asp Leu Ser Glu Asp Cys Leu Tyr Leu Asn Val Trp Ile Pro
        115                 120                 125

Ala Pro Lys Pro Lys Asn Ala Thr Val Leu Ile Trp Ile Tyr Gly Gly
    130                 135                 140

Gly Phe Gln Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
                165                 170                 175

Gly Ala Leu Gly Phe Leu Ala Leu Pro Gly Asn Pro Glu Ala Pro Gly
            180                 185                 190

Asn Met Gly Leu Phe Asp Gln Gln Leu Ala Leu Gln Trp Val Gln Lys
        195                 200                 205

Asn Ile Ala Ala Phe Gly Gly Asn Pro Lys Ser Val Thr Leu Phe Gly
    210                 215                 220

Glu Ser Ala Gly Ala Ala Ser Val Ser Leu His Leu Leu Ser Pro Gly
225                 230                 235                 240

Ser His Ser Leu Phe Thr Arg Ala Ile Leu Gln Ser Gly Ser Phe Asn
                245                 250                 255

Ala Pro Trp Ala Val Thr Ser Leu Tyr Glu Ala Arg Asn Arg Thr Leu
            260                 265                 270

Asn Leu Ala Lys Leu Thr Gly Cys Ser Arg Glu Asn Glu Thr Glu Ile
        275                 280                 285

Ile Lys Cys Leu Arg Asn Lys Asp Pro Gln Glu Ile Leu Leu Asn Glu
    290                 295                 300

Ala Phe Val Val Pro Tyr Gly Thr Pro His Ser Val Asn Phe Gly Pro
305                 310                 315                 320

Thr Val Asp Gly Asp Phe Leu Thr Asp Met Pro Asp Ile Leu Leu Glu
                325                 330                 335

Leu Gly Gln Phe Lys Lys Thr Gln Ile Leu Val Gly Val Asn Lys Asp
```

-continued

```
            340                 345                 350
Glu Gly Thr Ala Phe Leu Val Tyr Gly Ala Pro Gly Phe Ser Lys Asp
            355                 360                 365
Asn Asn Ser Ile Ile Thr Arg Lys Glu Phe Gln Glu Gly Leu Lys Ile
        370                 375                 380
Phe Phe Pro Gly Val Ser Glu Phe Gly Lys Glu Ser Ile Leu Phe His
385                 390                 395                 400
Tyr Thr Asp Trp Val Asp Asp Gln Arg Pro Glu Asn Tyr Arg Glu Ala
                405                 410                 415
Leu Gly Asp Val Val Gly Asp Tyr Asn Phe Ile Cys Pro Ala Leu Glu
                420                 425                 430
Phe Thr Lys Lys Phe Ser Glu Trp Gly Asn Asn Ala Phe Phe Tyr Tyr
            435                 440                 445
Phe Glu His Arg Ser Ser Lys Leu Pro Trp Pro Glu Trp Met Gly Val
        450                 455                 460
Met His Gly Tyr Glu Ile Glu Phe Val Phe Gly Leu Pro Leu Glu Arg
465                 470                 475                 480
Arg Asp Asn Tyr Thr Lys Ala Glu Glu Ile Leu Ser Arg Ser Ile Val
                485                 490                 495
Lys Arg Trp Ala Asn Phe Ala Lys Tyr Gly Asn Pro Asn Glu Thr Gln
                500                 505                 510
Asn Asn Ser Thr Ser Trp Pro Val Phe Lys Ser Thr Glu Gln Lys Tyr
            515                 520                 525
Leu Thr Leu Asn Thr Glu Ser Thr Arg Ile Met Thr Lys Leu Arg Ala
        530                 535                 540
Gln Gln Cys Arg Phe Trp Thr Ser Phe Phe Pro Lys Val Leu Glu Met
545                 550                 555                 560
Thr Gly Asn Ile Asp Glu Ala Glu Trp Glu Trp Lys Ala Gly Phe His
                565                 570                 575
Arg Trp Asn Asn Tyr Met Met Asp Trp Lys Asn Gln Phe Asn Asp Tyr
                580                 585                 590
Thr Ser Lys Lys Glu Ser Cys Val Gly Leu
            595                 600
```

(2) INFORMATION FOR SEQ ID NO:4:

(i) SEQUENCE CHARACTERISTICS:
        (A) LENGTH: 602 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:4:

```
Met His Ser Lys Val Thr Ile Ile Cys Ile Arg Phe Leu Phe Trp Phe
1                   5                   10                  15
Leu Leu Leu Cys Met Leu Ile Gly Lys Ser His Thr Glu Asp Asp Ile
            20                  25                  30
Ile Ile Ala Thr Lys Asn Gly Lys Val Arg Gly Met Asn Leu Thr Val
```

```
                      35                  40                  45
Phe Gly Gly Thr Val Thr Ala Phe Leu Gly Ile Pro Tyr Ala Gln Pro
 50                      55                  60

Pro Leu Gly Arg Leu Arg Phe Lys Lys Pro Gln Ser Leu Thr Lys Trp
 65                  70                  75                  80

Ser Asp Ile Trp Asn Ala Thr Lys Tyr Ala Asn Ser Cys Cys Gln Asn
                     85                  90                  95

Ile Asp Gln Ser Phe Pro Gly Phe His Gly Ser Glu Met Trp Asn Pro
                100                 105                 110

Asn Thr Asp Leu Ser Glu Asp Cys Leu Tyr Leu Asn Val Trp Ile Pro
                115                 120                 125

Ala Pro Lys Pro Lys Asn Ala Thr Val Leu Ile Trp Ile Tyr Gly Gly
130                 135                 140

Gly Phe Gln Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
                165                 170                 175

Gly Ala Leu Gly Phe Leu Ala Leu Pro Gly Asn Pro Glu Ala Pro Gly
                180                 185                 190

Asn Met Gly Leu Phe Asp Gln Gln Leu Ala Leu Gln Trp Val Gln Lys
                195                 200                 205

Asn Ile Ala Ala Phe Gly Gly Asn Pro Lys Ser Val Thr Leu Phe Gly
210                 215                 220

Glu Ser Ala Gly Ala Ala Ser Val Ser Leu His Leu Leu Ser Pro Gly
225                 230                 235                 240

Ser His Ser Leu Phe Thr Arg Ala Ile Leu Gln Ser Gly Ser Phe Asn
                245                 250                 255

Ala Pro Trp Ala Val Thr Ser Leu Tyr Glu Ala Arg Asn Arg Thr Leu
                260                 265                 270

Asn Leu Ala Lys Leu Thr Gly Cys Ser Arg Glu Asn Glu Thr Glu Ile
                275                 280                 285

Ile Lys Cys Leu Arg Asn Lys Asp Pro Gln Glu Ile Leu Leu Asn Glu
                290                 295                 300

Ala Phe Val Val Pro Tyr Gly Thr Pro His Ser Val Asn Phe Gly Pro
305                 310                 315                 320

Thr Val Asp Gly Asp Phe Leu Thr Asp Met Pro Asp Ile Leu Leu Glu
                325                 330                 335

Leu Gly Gln Phe Lys Lys Thr Gln Ile Leu Val Gly Val Asn Lys Asp
                340                 345                 350

Glu Gly Thr Ala Phe Leu Val Tyr Gly Ala Pro Gly Phe Ser Lys Asp
                355                 360                 365

Asn Asn Ser Ile Ile Thr Arg Lys Glu Phe Gln Glu Gly Leu Lys Ile
                370                 375                 380

Phe Phe Pro Gly Val Ser Glu Phe Gly Lys Glu Ser Ile Leu Phe His
385                 390                 395                 400

Tyr Thr Asp Trp Val Asp Asp Gln Arg Pro Glu Asn Tyr Arg Glu Ala
                405                 410                 415

Leu Gly Asp Val Val Gly Asp Tyr Asn Phe Ile Cys Pro Ala Leu Glu
                420                 425                 430

Phe Thr Lys Lys Phe Ser Glu Trp Gly Asn Asn Ala Phe Phe Tyr Tyr
                435                 440                 445

Phe Glu His Arg Ser Ser Lys Leu Pro Trp Pro Glu Trp Met Gly Val
450                 455                 460
```

```
Met His Gly Tyr Glu Ile Glu Phe Val Phe Gly Leu Pro Leu Glu Arg
465                 470                 475                 480

Arg Asp Asn Tyr Thr Lys Ala Glu Glu Ile Leu Ser Arg Ser Ile Val
                485                 490                 495

Lys Arg Trp Ala Asn Phe Ala Lys Tyr Gly Asn Pro Asn Glu Thr Gln
            500                 505                 510

Asn Asn Ser Thr Ser Trp Pro Val Phe Lys Ser Thr Glu Gln Lys Tyr
            515                 520                 525

Leu Thr Leu Asn Thr Glu Ser Thr Arg Ile Met Thr Lys Leu Arg Ala
            530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
            580                 585                 590

Thr Ser Lys Lys Glu Ser Cys Val Gly Leu
            595                 600
```

(2) INFORMATION FOR SEQ ID NO:5:

(i) SEQUENCE CHARACTERISTICS:
        (A) LENGTH: 602 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:5:

```
Met His Ser Lys Val Thr Ile Ile Cys Ile Arg Phe Leu Phe Trp Phe
1               5                   10                  15

Leu Leu Leu Cys Met Leu Ile Gly Lys Ser His Thr Glu Asp Asp Ile
                20                  25                  30

Ile Ile Ala Thr Lys Asn Gly Lys Val Arg Gly Met Asn Leu Thr Val
            35                  40                  45

Phe Gly Gly Thr Val Thr Ala Phe Leu Gly Ile Pro Tyr Ala Gln Pro
50                  55                  60

Pro Leu Gly Arg Leu Arg Phe Lys Lys Pro Gln Ser Leu Thr Lys Trp
65                  70                  75                  80

Ser Asp Ile Trp Asn Ala Thr Lys Tyr Ala Asn Ser Cys Cys Gln Asn
                85                  90                  95

Ile Asp Gln Ser Phe Pro Gly Phe His Gly Ser Glu Met Trp Asn Pro
            100                 105                 110

Asn Thr Asp Leu Ser Glu Asp Cys Leu Tyr Leu Asn Val Trp Ile Pro
            115                 120                 125

Ala Pro Lys Pro Lys Asn Ala Thr Val Leu Ile Trp Ile Tyr Gly Gly
            130                 135                 140

Gly Phe Gln Thr Gly Thr Ser Ser Leu His Val Tyr Asp Gly Lys Phe
145                 150                 155                 160
```

-continued

```
Leu Ala Arg Val Glu Arg Val Ile Val Val Ser Met Asn Tyr Arg Val
                165                 170                 175
Gly Ala Leu Gly Phe Leu Ala Leu Pro Gly Asn Pro Glu Ala Pro Gly
            180                 185                 190
Asn Met Gly Leu Phe Asp Gln Gln Leu Ala Leu Gln Trp Val Gln Lys
        195                 200                 205
Asn Ile Ala Ala Phe Gly Gly Asn Pro Lys Ser Val Thr Leu Phe Gly
    210                 215                 220
Glu Ser Ala Gly Ala Ala Ser Val Ser Leu His Leu Leu Ser Pro Gly
225                 230                 235                 240
Ser His Ser Leu Phe Thr Arg Ala Ile Leu Gln Ser Gly Ser Phe Asn
                245                 250                 255
Ala Pro Trp Ala Val Thr Ser Leu Tyr Glu Ala Arg Asn Arg Thr Leu
            260                 265                 270
Asn Leu Ala Lys Leu Thr Gly Cys Ser Arg Glu Asn Glu Thr Glu Ile
        275                 280                 285
Ile Lys Cys Leu Arg Asn Lys Asp Pro Gln Glu Ile Leu Leu Asn Glu
    290                 295                 300
Ala Phe Val Val Pro Tyr Gly Thr Pro Leu Ser His Asn Phe Gly Pro
305                 310                 315                 320
Thr Val Asp Gly Asp Phe Leu Thr Asp Met Pro Asp Ile Leu Leu Glu
                325                 330                 335
Leu Gly Gln Phe Lys Lys Thr Gln Ile Leu Val Gly Val Asn Lys Asp
            340                 345                 350
Glu Gly Thr Ala Phe Leu Val Tyr Gly Ala Pro Gly Phe Ser Lys Asp
        355                 360                 365
Asn Asn Ser Ile Ile Thr Arg Lys Glu Phe Gln Glu Gly Leu Lys Ile
    370                 375                 380
Phe Phe Pro Gly Val Ser Glu Phe Gly Lys Glu Ser Ile Leu Phe His
385                 390                 395                 400
Tyr Thr Asp Trp Val Asp Asp Gln Arg Pro Glu Asn Tyr Arg Glu Ala
                405                 410                 415
Leu Gly Asp Val Val Gly Asp Tyr Asn Phe Ile Cys Pro Ala Leu Glu
            420                 425                 430
Phe Thr Lys Lys Phe Ser Glu Trp Gly Asn Asn Ala Phe Phe Tyr Tyr
        435                 440                 445
Phe Glu His Arg Ser Ser Lys Leu Pro Trp Pro Glu Trp Met Gly Val
    450                 455                 460
Met His Gly Tyr Glu Ile Glu Phe Val Phe Gly Leu Pro Leu Glu Arg
465                 470                 475                 480
Arg Asp Asn Tyr Thr Lys Ala Glu Glu Ile Leu Ser Arg Ser Ile Val
                485                 490                 495
Lys Arg Trp Ala Asn Phe Ala Lys Tyr Gly Asn Pro Asn Glu Thr Gln
            500                 505                 510
Asn Asn Ser Thr Ser Trp Pro Val Phe Lys Ser Thr Glu Gln Lys Tyr
        515                 520                 525
Leu Thr Leu Asn Thr Glu Ser Thr Arg Ile Met Thr Lys Leu Arg Ala
    530                 535                 540
Gln Gln Cys Arg Phe Trp Thr Ser Phe Phe Pro Lys Val Leu Glu Met
545                 550                 555                 560
Thr Gly Asn Ile Asp Glu Ala Glu Trp Glu Trp Lys Ala Gly Phe His
                565                 570                 575
Arg Trp Asn Asn Tyr Met Met Asp Trp Lys Asn Gln Phe Asn Asp Tyr
            580                 585                 590
```

```
Thr Ser Lys Lys Glu Ser Cys Val Gly Leu
        595                 600
```

(2) INFORMATION FOR SEQ ID NO:6:

(i) SEQUENCE CHARACTERISTICS:
        (A) LENGTH: 602 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:6:

```
Met His Ser Lys Val Thr Ile Ile Cys Ile Arg Phe Leu Phe Trp Phe
1               5                   10                  15

Leu Leu Leu Cys Met Leu Ile Gly Lys Ser His Thr Glu Asp Asp Ile
            20                  25                  30

Ile Ile Ala Thr Lys Asn Gly Lys Val Arg Gly Met Asn Leu Thr Val
                35                  40                  45

Phe Gly Gly Thr Val Thr Ala Phe Leu Gly Ile Pro Tyr Ala Gln Pro
    50                  55                  60

Pro Leu Gly Arg Leu Arg Phe Lys Pro Gln Ser Leu Thr Lys Trp
65                  70                  75                  80

Ser Asp Ile Trp Asn Ala Thr Lys Tyr Ala Asn Ser Cys Cys Gln Asn
                85                  90                  95

Ile Asp Gln Ser Phe Pro Gly Phe His Gly Ser Glu Met Trp Asn Pro
                100                 105                 110

Asn Thr Asp Leu Ser Glu Asp Cys Leu Tyr Leu Asn Val Trp Ile Pro
            115                 120                 125

Ala Pro Lys Pro Lys Asn Ala Thr Val Leu Ile Trp Ile Tyr Gly Gly
        130                 135                 140

Lys Phe Gln Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
                165                 170                 175

Gly Ala Leu Gly Phe Leu Ala Leu Pro Gly Asn Pro Glu Ala Pro Gly
            180                 185                 190

Asn Met Gly Leu Phe Asp Gln Gln Leu Ala Leu Gln Trp Val Gln Lys
        195                 200                 205

Asn Ile Ala Ala Phe Gly Gly Asn Pro Lys Ser Val Thr Leu Phe Gly
210                 215                 220

Glu Ser Ala Gly Ala Ala Ser Val Ser Leu His Leu Leu Ser Pro Gly
225                 230                 235                 240

Ser His Ser Leu Phe Thr Arg Ala Ile Leu Gln Ser Gly Ser Phe Asn
                245                 250                 255

Ala Pro Trp Ala Val Thr Ser Leu Tyr Glu Ala Arg Asn Arg Thr Leu
            260                 265                 270

Asn Leu Ala Lys Leu Thr Gly Cys Ser Arg Glu Asn Glu Thr Glu Ile
        275                 280                 285
```

```
Ile Lys Cys Leu Arg Asn Lys Asp Pro Gln Glu Ile Leu Leu Asn Glu
    290                 295                 300
Ala Phe Val Val Pro Tyr Gly Thr Pro Leu Ser Val Asn Phe Gly Pro
305                 310                 315                 320
Thr Val Asp Gly Asp Phe Leu Thr Asp Met Pro Asp Ile Leu Leu Glu
                325                 330                 335
Leu Gly Gln Phe Lys Lys Thr Gln Ile Leu Val Gly Val Asn Lys Asp
                340                 345                 350
Glu Gly Thr Ala Phe Leu Val Tyr Gly Ala Pro Gly Phe Ser Lys Asp
            355                 360                 365
Asn Asn Ser Ile Ile Thr Arg Lys Glu Phe Gln Glu Gly Leu Lys Ile
        370                 375                 380
Phe Phe Pro Gly Val Ser Glu Phe Gly Lys Glu Ser Ile Leu Phe His
385                 390                 395                 400
Tyr Thr Asp Trp Val Asp Asp Gln Arg Pro Glu Asn Tyr Arg Glu Ala
                405                 410                 415
Leu Gly Asp Val Val Gly Asp Tyr Asn Phe Ile Cys Pro Ala Leu Glu
                420                 425                 430
Phe Thr Lys Lys Phe Ser Glu Trp Gly Asn Asn Ala Phe Phe Tyr Tyr
            435                 440                 445
Phe Glu His Arg Ser Ser Lys Leu Pro Trp Pro Glu Trp Met Gly Val
        450                 455                 460
Met His Gly Tyr Glu Ile Glu Phe Val Phe Gly Leu Pro Leu Glu Arg
465                 470                 475                 480
Arg Asp Asn Tyr Thr Lys Ala Glu Glu Ile Leu Ser Arg Ser Ile Val
                485                 490                 495
Lys Arg Trp Ala Asn Phe Ala Lys Tyr Gly Asn Pro Asn Glu Thr Gln
                500                 505                 510
Asn Asn Ser Thr Ser Trp Pro Val Phe Lys Ser Thr Glu Gln Lys Tyr
            515                 520                 525
Leu Thr Leu Asn Thr Glu Ser Thr Arg Ile Met Thr Lys Leu Arg Ala
        530                 535                 540
Gln Gln Cys Arg Phe Trp Thr Ser Phe Phe Pro Lys Val Leu Glu Met
545                 550                 555                 560
Thr Gly Asn Ile Asp Glu Ala Glu Trp Glu Trp Lys Ala Gly Phe His
                565                 570                 575
Arg Trp Asn Asn Tyr Met Met Asp Trp Lys Asn Gln Phe Asn Asp Tyr
                580                 585                 590
Thr Ser Lys Lys Glu Ser Cys Val Gly Leu
        595                 600

(2) INFORMATION FOR SEQ ID NO:7:

(i) SEQUENCE CHARACTERISTICS:
        (A) LENGTH: 602 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases
```

(xi) SEQUENCE DESCRIPTION: SEQ ID NO:7:

Met His Ser Lys Val Thr Ile Ile Cys Ile Arg Phe Leu Phe Trp Phe
1               5                   10                  15

Leu Leu Leu Cys Met Leu Ile Gly Lys Ser His Thr Glu Asp Asp Ile
            20                  25                  30

Ile Ile Ala Thr Lys Asn Gly Lys Val Arg Gly Met Asn Leu Thr Val
        35                  40                  45

Phe Gly Gly Thr Val Thr Ala Phe Leu Gly Ile Pro Tyr Ala Gln Pro
    50                  55                  60

Pro Leu Gly Arg Leu Arg Phe Lys Lys Pro Gln Ser Leu Thr Lys Trp
65                  70                  75                  80

Ser Asp Ile Trp Asn Ala Thr Lys Tyr Ala Asn Ser Cys Cys Gln Asn
                85                  90                  95

Ile Asp Gln Ser Phe Pro Gly Phe His Gly Ser Glu Met Trp Asn Pro
            100                 105                 110

Asn Thr Asp Leu Ser Glu Asp Cys Leu Tyr Leu Asn Val Trp Ile Pro
        115                 120                 125

Ala Pro Lys Pro Lys Asn Ala Thr Val Leu Ile Trp Ile Tyr Gly Gly
    130                 135                 140

Cys Phe Gln Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
                165                 170                 175

Gly Ala Leu Gly Phe Leu Ala Leu Pro Gly Asn Pro Glu Ala Pro Gly
            180                 185                 190

Asn Met Gly Leu Phe Asp Gln Gln Leu Ala Leu Gln Trp Val Gln Lys
        195                 200                 205

Asn Ile Ala Ala Phe Gly Gly Asn Pro Lys Ser Val Thr Leu Phe Gly
    210                 215                 220

Glu Ser Ala Gly Ala Ala Ser Val Ser Leu His Leu Leu Ser Pro Gly
225                 230                 235                 240

Ser His Ser Leu Phe Thr Arg Ala Ile Leu Gln Ser Gly Ser Phe Asn
                245                 250                 255

Ala Pro Trp Ala Val Thr Ser Leu Tyr Glu Ala Arg Asn Arg Thr Leu
            260                 265                 270

Asn Leu Ala Lys Leu Thr Gly Cys Ser Arg Glu Asn Glu Thr Glu Ile
        275                 280                 285

Ile Lys Cys Leu Arg Asn Lys Asp Pro Gln Glu Ile Leu Leu Asn Glu
    290                 295                 300

Ala Phe Val Val Pro Tyr Gly Thr Pro Leu Ser Val Asn Phe Gly Pro
305                 310                 315                 320

Thr Val Asp Gly Asp Phe Leu Thr Asp Met Pro Asp Ile Leu Leu Glu
                325                 330                 335

Leu Gly Gln Phe Lys Lys Thr Gln Ile Leu Val Gly Val Asn Lys Asp
            340                 345                 350

Glu Gly Thr Ala Phe Leu Val Tyr Gly Ala Pro Gly Phe Ser Lys Asp
        355                 360                 365

Asn Asn Ser Ile Ile Thr Arg Lys Glu Phe Gln Glu Gly Leu Lys Ile
    370                 375                 380

Phe Phe Pro Gly Val Ser Glu Phe Gly Lys Glu Ser Ile Leu Phe His
385                 390                 395                 400

Tyr Thr Asp Trp Val Asp Asp Gln Arg Pro Glu Asn Tyr Arg Glu Ala 405                 410                 415
Leu Gly Asp Val Val Gly Asp Tyr Asn Phe Ile Cys Pro Ala Leu Glu
                420                 425                 430

Phe Thr Lys Lys Phe Ser Glu Trp Gly Asn Asn Ala Phe Phe Tyr Tyr
            435                 440                 445

Phe Glu His Arg Ser Ser Lys Leu Pro Trp Pro Glu Trp Met Gly Val
    450                 455                 460

Met His Gly Tyr Glu Ile Glu Phe Val Phe Gly Leu Pro Leu Glu Arg
465                 470                 475                 480

Arg Asp Asn Tyr Thr Lys Ala Glu Glu Ile Leu Ser Arg Ser Ile Val
                485                 490                 495

Lys Arg Trp Ala Asn Phe Ala Lys Tyr Gly Asn Pro Asn Glu Thr Gln
            500                 505                 510

Asn Asn Ser Thr Ser Trp Pro Val Phe Lys Ser Thr Glu Gln Lys Tyr
        515                 520                 525

Leu Thr Leu Asn Thr Glu Ser Thr Arg Ile Met Thr Lys Leu Arg Ala
    530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
            580                 585                 590

Thr Ser Lys Lys Glu Ser Cys Val Gly Leu
        595                 600

(2) INFORMATION FOR SEQ ID NO:8:

(i) SEQUENCE CHARACTERISTICS:
        (A) LENGTH: 602 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:8:

Met His Ser Lys Val Thr Ile Ile Cys Ile Arg Phe Leu Phe Trp Phe
1               5                  10                  15

Leu Leu Leu Cys Met Leu Ile Gly Lys Ser His Thr Glu Asp Asp Ile
            20                  25                  30

Ile Ile Ala Thr Lys Asn Gly Lys Val Arg Gly Met Asn Leu Thr Val
        35                  40                  45

Phe Gly Gly Thr Val Thr Ala Phe Leu Gly Ile Pro Tyr Ala Gln Pro
    50                  55                  60

Pro Leu Gly Arg Leu Arg Phe Lys Lys Pro Gln Ser Leu Thr Lys Trp
65              70                  75                  80

Ser Asp Ile Trp Asn Ala Thr Lys Tyr Ala Asn Ser Cys Cys Gln Asn
            85                  90                  95

Ile Asp Gln Ser Phe Pro Gly Phe His Gly Ser Glu Met Trp Asn Pro

-continued

```
                100                 105                 110
Asn Thr Asp Leu Ser Glu Asp Cys Leu Tyr Leu Asn Val Trp Ile Pro
            115                 120                 125
Ala Pro Lys Pro Lys Asn Ala Thr Val Leu Ile Trp Ile Tyr Gly Gly
130                 135                 140
His Phe Glu Thr Gly Thr Ser Ser Leu His Val Tyr Asp Gly Lys Phe
145                 150                 155                 160
Leu Ala Arg Val Glu Arg Val Ile Val Val Ser Met Asn Tyr Arg Val
                165                 170                 175
Gly Ala Leu Gly Phe Leu Ala Leu Pro Gly Asn Pro Glu Ala Pro Gly
            180                 185                 190
Asn Met Gly Leu Phe Asp Gln Gln Leu Ala Leu Gln Trp Val Gln Lys
            195                 200                 205
Asn Ile Ala Ala Phe Gly Gly Asn Pro Lys Ser Val Thr Leu Phe Gly
210                 215                 220
Glu Ser Ala Gly Ala Ala Ser Val Ser Leu His Leu Leu Ser Pro Gly
225                 230                 235                 240
Ser His Ser Leu Phe Thr Arg Ala Ile Leu Gln Ser Gly Ser Phe Asn
                245                 250                 255
Ala Pro Trp Ala Val Thr Ser Leu Tyr Glu Ala Arg Asn Arg Thr Leu
            260                 265                 270
Asn Leu Ala Lys Leu Thr Gly Cys Ser Arg Glu Asn Glu Thr Glu Ile
            275                 280                 285
Ile Lys Cys Leu Arg Asn Lys Asp Pro Gln Glu Ile Leu Leu Asn Glu
            290                 295                 300
Ala Phe Val Val Pro Tyr Gly Thr Pro Leu Ser Val Asn Phe Gly Pro
305                 310                 315                 320
Thr Val Asp Gly Asp Phe Leu Thr Asp Met Pro Asp Ile Leu Leu Glu
                325                 330                 335
Leu Gly Gln Phe Lys Lys Thr Gln Ile Leu Val Gly Val Asn Lys Asp
            340                 345                 350
Glu Gly Thr Ala Phe Leu Val Tyr Gly Ala Pro Gly Phe Ser Lys Asp
            355                 360                 365
Asn Asn Ser Ile Ile Thr Arg Lys Glu Phe Gln Glu Gly Leu Lys Ile
370                 375                 380
Phe Phe Pro Gly Val Ser Glu Phe Gly Lys Glu Ser Ile Leu Phe His
385                 390                 395                 400
Tyr Thr Asp Trp Val Asp Asp Gln Arg Pro Glu Asn Tyr Arg Glu Ala
                405                 410                 415
Leu Gly Asp Val Val Gly Asp Tyr Asn Phe Ile Cys Pro Ala Leu Glu
            420                 425                 430
Phe Thr Lys Lys Phe Ser Glu Trp Gly Asn Asn Ala Phe Phe Tyr Tyr
            435                 440                 445
Phe Glu His Arg Ser Ser Lys Leu Pro Trp Pro Glu Trp Met Gly Val
450                 455                 460
Met His Gly Tyr Glu Ile Glu Phe Val Phe Gly Leu Pro Leu Glu Arg
465                 470                 475                 480
Arg Asp Asn Tyr Thr Lys Ala Glu Glu Ile Leu Ser Arg Ser Ile Val
                485                 490                 495
Lys Arg Trp Ala Asn Phe Ala Lys Tyr Gly Asn Pro Asn Glu Thr Gln
            500                 505                 510
Asn Asn Ser Thr Ser Trp Pro Val Phe Lys Ser Thr Glu Gln Lys Tyr
            515                 520                 525
```

-continued

```
Leu Thr Leu Asn Thr Glu Ser Thr Arg Ile Met Thr Lys Leu Arg Ala
    530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
            580                 585                 590

Thr Ser Lys Lys Glu Ser Cys Val Gly Leu
            595                 600
```

(2) INFORMATION FOR SEQ ID NO:9:

(i) SEQUENCE CHARACTERISTICS:
        (A) LENGTH: 602 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:9:

```
Met His Ser Lys Val Thr Ile Ile Cys Ile Arg Phe Leu Phe Trp Phe
1               5                   10                  15

Leu Leu Leu Cys Met Leu Ile Gly Lys Ser His Thr Glu Asp Asp Ile
            20                  25                  30

Ile Ile Ala Thr Lys Asn Gly Lys Val Arg Gly Met Asn Leu Thr Val
        35                  40                  45

Phe Gly Gly Thr Val Thr Ala Phe Leu Gly Ile Pro Tyr Ala Gln Pro
    50                  55                  60

Pro Leu Gly Arg Leu Arg Phe Lys Lys Pro Gln Ser Leu Thr Lys Trp
65                  70                  75                  80

Ser Asp Ile Trp Asn Ala Thr Lys Tyr Ala Asn Ser Cys Cys Gln Asn
                85                  90                  95

Ile Asp Gln Ser Phe Pro Gly Phe His Gly Ser Glu Met Trp Asn Pro
            100                 105                 110

Asn Thr Asp Leu Ser Glu Asp Cys Leu Tyr Leu Asn Val Trp Ile Pro
        115                 120                 125

Ala Pro Lys Pro Lys Asn Ala Thr Val Leu Ile Trp Ile Tyr Gly Gly
    130                 135                 140

Gly Phe Gln Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
                165                 170                 175

Gly Ala Leu Gly Phe Leu Ala Leu Pro Gly Asn Pro Glu Ala Pro Gly
            180                 185                 190

Asn Met Gly Leu Phe Asp Gln Gln Leu Ala Leu Gln Trp Val Gln Lys
        195                 200                 205

Asn Ile Ala Ala Phe Gly Gly Asn Pro Lys Ser Val Thr Leu Phe Gly
    210                 215                 220
```

-continued

```
Glu Ser Ala Gly Ala Ala Ser Val Ser Leu His Leu Leu Ser Pro Gly
225                 230                 235                 240

Ser His Ser Leu Phe Thr Arg Ala Ile Leu Gln Ser Gly Ser Phe Asn
            245                 250                 255

Ala Pro Trp Ala Val Thr Ser Leu Tyr Glu Ala Arg Asn Arg Thr Leu
            260                 265                 270

Asn Leu Ala Lys Leu Thr Gly Cys Ser Arg Glu Asn Glu Thr Glu Ile
            275                 280                 285

Ile Lys Cys Leu Arg Asn Lys Asp Pro Gln Glu Ile Leu Leu Asn Glu
290                 295                 300

Ala Phe Val Val Pro Tyr Gly Thr Pro His Ser Val Asn Phe Gly Pro
305                 310                 315                 320

Thr Val Asp Gly Asp Phe Leu Thr Asp Met Pro Asp Ile Leu Leu Glu
            325                 330                 335

Leu Gly Gln Phe Lys Lys Thr Gln Ile Leu Val Gly Val Asn Lys Asp
            340                 345                 350

Glu Gly Thr Ala Asp Leu Val Tyr Gly Ala Pro Gly Phe Ser Lys Asp
            355                 360                 365

Asn Asn Ser Ile Ile Thr Arg Lys Glu Phe Gln Glu Gly Leu Lys Ile
370                 375                 380

Phe Phe Pro Gly Val Ser Glu Phe Gly Lys Glu Ser Ile Leu Phe His
385                 390                 395                 400

Tyr Thr Asp Trp Val Asp Asp Gln Arg Pro Glu Asn Tyr Arg Glu Ala
            405                 410                 415

Leu Gly Asp Val Val Gly Asp Tyr Asn Phe Ile Cys Pro Ala Leu Glu
            420                 425                 430

Phe Thr Lys Lys Phe Ser Glu Trp Gly Asn Asn Ala Phe Phe Tyr Tyr
            435                 440                 445

Phe Glu His Arg Ser Ser Lys Leu Pro Trp Pro Glu Trp Met Gly Val
450                 455                 460

Met His Gly Tyr Glu Ile Glu Phe Val Phe Gly Leu Pro Leu Glu Arg
465                 470                 475                 480

Arg Asp Asn Tyr Thr Lys Ala Glu Glu Ile Leu Ser Arg Ser Ile Val
            485                 490                 495

Lys Arg Trp Ala Asn Phe Ala Lys Tyr Gly Asn Pro Asn Glu Thr Gln
            500                 505                 510

Asn Asn Ser Thr Ser Trp Pro Val Phe Lys Ser Thr Glu Gln Lys Tyr
            515                 520                 525

Leu Thr Leu Asn Thr Glu Ser Thr Arg Ile Met Thr Lys Leu Arg Ala
530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
            565                 570                 575

Arg Trp Asn Asn Tyr Met Met Asp Trp Lys Asn Gln Phe Asn Asp Tyr
            580                 585                 590

Thr Ser Lys Lys Glu Ser Cys Val Gly Leu
            595                 600
```

(2) INFORMATION FOR SEQ ID NO:10:

(i) SEQUENCE CHARACTERISTICS:
        (A) LENGTH: 602 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
    (A) ORGANISM: human esterases (xi) SEQUENCE DESCRIPTION: SEQ ID NO:10:

```
Met His Ser Lys Val Thr Ile Ile Cys Ile Arg Phe Leu Phe Trp Phe
1               5                   10                  15

Leu Leu Leu Cys Met Leu Ile Gly Lys Ser His Thr Glu Asp Asp Ile
            20                  25                  30

Ile Ile Ala Thr Lys Asn Gly Lys Val Arg Gly Met Asn Leu Thr Val
                35                  40                  45

Phe Gly Gly Thr Val Thr Ala Phe Leu Gly Ile Pro Tyr Ala Gln Pro
    50                  55                  60

Pro Leu Gly Arg Leu Arg Phe Lys Lys Pro Gln Ser Leu Thr Lys Trp
65                  70                  75                  80

Ser Asp Ile Trp Asn Ala Thr Lys Tyr Ala Asn Ser Cys Cys Gln Asn
                85                  90                  95

Ile Asp Gln Ser Phe Pro Gly Phe His Gly Ser Glu Met Trp Asn Pro
                100                 105                 110

Asn Thr Asp Leu Ser Glu Asp Cys Leu Tyr Leu Asn Val Trp Ile Pro
            115                 120                 125

Ala Pro Lys Pro Lys Asn Ala Thr Val Leu Ile Trp Ile Tyr Gly Gly
            130                 135                 140

Gly Phe Gln Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
                165                 170                 175

Gly Ala Leu Gly Phe Leu Ala Leu Pro Gly Asn Pro Glu Ala Pro Gly
            180                 185                 190

Asn Met Gly Leu Phe Asp Gln Gln Leu Ala Leu Gln Trp Val Gln Lys
            195                 200                 205

Asn Ile Ala Ala Phe Gly Gly Asn Pro Lys Ser Val Thr Leu Phe Gly
210                 215                 220

Glu Ser Ala Gly Ala Ala Ser Val Ser Leu His Leu Leu Ser Pro Gly
225                 230                 235                 240

Ser His Ser Leu Phe Thr Arg Ala Ile Leu Gln Ser Gly Ser Phe Asn
                245                 250                 255

Ala Pro Trp Ala Val Thr Ser Leu Tyr Glu Ala Arg Asn Arg Thr Leu
            260                 265                 270

Asn Leu Ala Lys Leu Thr Gly Cys Ser Arg Glu Asn Glu Thr Glu Ile
            275                 280                 285

Ile Lys Cys Leu Arg Asn Lys Asp Pro Gln Glu Ile Leu Leu Asn Glu
            290                 295                 300

Ala Phe Val Val Pro Tyr Gly Thr Pro His Ser Val Asn Phe Gly Pro
305                 310                 315                 320

Thr Val Asp Gly Asp Phe Leu Thr Asp Met Pro Asp Ile Leu Leu Glu
                325                 330                 335

Leu Gly Gln Phe Lys Lys Thr Gln Ile Leu Val Gly Val Asn Lys Asp
                340                 345                 350
```

-continued

```
Glu Gly Thr Ala Glu Leu Val Tyr Gly Ala Pro Gly Phe Ser Lys Asp
        355                 360                 365

Asn Asn Ser Ile Ile Thr Arg Lys Glu Phe Gln Glu Gly Leu Lys Ile
    370                 375                 380

Phe Phe Pro Gly Val Ser Glu Phe Gly Lys Glu Ser Ile Leu Phe His
385                 390                 395                 400

Tyr Thr Asp Trp Val Asp Asp Gln Arg Pro Glu Asn Tyr Arg Glu Ala
                405                 410                 415

Leu Gly Asp Val Val Gly Asp Tyr Asn Phe Ile Cys Pro Ala Leu Glu
            420                 425                 430

Phe Thr Lys Lys Phe Ser Glu Trp Gly Asn Asn Ala Phe Phe Tyr Tyr
        435                 440                 445

Phe Glu His Arg Ser Ser Lys Leu Pro Trp Pro Glu Trp Met Gly Val
    450                 455                 460

Met His Gly Tyr Glu Ile Glu Phe Val Phe Gly Leu Pro Leu Glu Arg
465                 470                 475                 480

Arg Asp Asn Tyr Thr Lys Ala Glu Glu Ile Leu Ser Arg Ser Ile Val
                485                 490                 495

Lys Arg Trp Ala Asn Phe Ala Lys Tyr Gly Asn Pro Asn Glu Thr Gln
            500                 505                 510

Asn Asn Ser Thr Ser Trp Pro Val Phe Lys Ser Thr Glu Gln Lys Tyr
        515                 520                 525

Leu Thr Leu Asn Thr Glu Ser Thr Arg Ile Met Thr Lys Leu Arg Ala
    530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
            580                 585                 590

Thr Ser Lys Lys Glu Ser Cys Val Gly Leu
        595                 600
```

(2) INFORMATION FOR SEQ ID NO:11:

(i) SEQUENCE CHARACTERISTICS:
        (A) LENGTH: 602 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
       (A) ORGANISM: human esterases (xi) SEQUENCE DESCRIPTION: SEQ ID NO:11:

```
Met His Ser Lys Val Thr Ile Ile Cys Ile Arg Phe Leu Phe Trp Phe
1               5                   10                  15

Leu Leu Leu Cys Met Leu Ile Gly Lys Ser His Thr Glu Asp Asp Ile
            20                  25                  30

Ile Ile Ala Thr Lys Asn Gly Lys Val Arg Gly Met Asn Leu Thr Val
        35                  40                  45
```

```
Phe Gly Gly Thr Val Thr Ala Phe Leu Gly Ile Pro Tyr Ala Gln Pro
 50                      55                      60
Pro Leu Gly Arg Leu Arg Phe Lys Lys Pro Gln Ser Leu Thr Lys Trp
 65                      70                      75                      80
Ser Asp Ile Trp Asn Ala Thr Lys Tyr Ala Asn Ser Cys Cys Gln Asn
                         85                      90                      95
Ile Asp Gln Ser Phe Pro Gly Phe His Gly Ser Glu Met Trp Asn Pro
            100                     105                     110
Asn Thr Asp Leu Ser Glu Asp Cys Leu Tyr Leu Asn Val Trp Ile Pro
        115                     120                     125
Ala Pro Lys Pro Lys Asn Ala Thr Val Leu Ile Trp Ile Tyr Gly Gly
    130                     135                     140
Gly Phe Gln Thr Gly Thr Ser Ser Leu His Val Tyr Asp Gly Lys Phe
145                     150                     155                     160
Leu Ala Arg Val Glu Arg Val Ile Val Val Ser Met Asn Tyr Arg Val
                165                     170                     175
Gly Ala Leu Gly Phe Leu Ala Leu Pro Gly Asn Pro Glu Ala Pro Gly
            180                     185                     190
Asn Met Gly Leu Phe Asp Gln Gln Leu Ala Leu Gln Trp Val Gln Lys
        195                     200                     205
Asn Ile Ala Ala Phe Gly Gly Asn Pro Lys Ser Val Thr Leu Phe Gly
    210                     215                     220
Glu Ser Ala Gly Ala Ala Ser Val Ser Leu His Leu Leu Ser Pro Gly
225                     230                     235                     240
Ser His Ser Leu Phe Thr Arg Ala Ile Leu Gln Ser Gly Ser Phe Asn
                245                     250                     255
Ala Pro Trp Ala Val Thr Ser Leu Tyr Glu Ala Arg Asn Arg Thr Leu
            260                     265                     270
Asn Leu Ala Lys Leu Thr Gly Cys Ser Arg Glu Asn Glu Thr Glu Ile
        275                     280                     285
Ile Lys Cys Leu Arg Asn Lys Asp Pro Gln Glu Ile Leu Leu Asn Glu
    290                     295                     300
Ala Phe Val Val Pro Tyr Gly Thr Pro Leu Ser His Asn Phe Glu Pro
305                     310                     315                     320
Thr Val Asp Gly Asp Phe Leu Thr Asp Met Pro Asp Ile Leu Leu Glu
                325                     330                     335
Leu Gly Gln Phe Lys Lys Thr Gln Ile Leu Val Gly Val Asn Lys Asp
            340                     345                     350
Glu Gly Thr Ala Phe Leu Val Tyr Gly Ala Pro Gly Phe Ser Lys Asp
        355                     360                     365
Asn Asn Ser Ile Ile Thr Arg Lys Glu Phe Gln Glu Gly Leu Lys Ile
    370                     375                     380
Phe Phe Pro Gly Val Ser Glu Phe Gly Lys Glu Ser Ile Leu Phe His
385                     390                     395                     400
Tyr Thr Asp Trp Val Asp Asp Gln Arg Pro Glu Asn Tyr Arg Glu Ala
                405                     410                     415
Leu Gly Asp Val Val Gly Asp Tyr Asn Phe Ile Cys Pro Ala Leu Glu
            420                     425                     430
Phe Thr Lys Lys Phe Ser Glu Trp Gly Asn Asn Ala Phe Phe Tyr Tyr
        435                     440                     445
Phe Glu His Arg Ser Ser Lys Leu Pro Trp Pro Glu Trp Met Gly Val
    450                     455                     460
Met His Gly Tyr Glu Ile Glu Phe Val Phe Gly Leu Pro Leu Glu Arg
```

```
           465                 470                 475                 480
Arg Asp Asn Tyr Thr Lys Ala Glu Glu Ile Leu Ser Arg Ser Ile Val
                        485                 490                 495

Lys Arg Trp Ala Asn Phe Ala Lys Tyr Gly Asn Pro Asn Glu Thr Gln
                500                 505                 510

Asn Asn Ser Thr Ser Trp Pro Val Phe Lys Ser Thr Glu Gln Lys Tyr
                515                 520                 525

Leu Thr Leu Asn Thr Glu Ser Thr Arg Ile Met Thr Lys Leu Arg Ala
            530                 535                 540

Gln Gln Cys Arg Phe Trp Thr Ser Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
                580                 585                 590

Thr Ser Lys Lys Glu Ser Cys Val Gly Leu
            595                 600
```

(2) INFORMATION FOR SEQ ID NO:12:

(i) SEQUENCE CHARACTERISTICS:
        (A) LENGTH: 602 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:12:

```
Met His Ser Lys Val Thr Ile Ile Cys Ile Arg Phe Leu Phe Trp Phe
1                   5                   10                  15

Leu Leu Leu Cys Met Leu Ile Gly Lys Ser His Thr Glu Asp Asp Ile
                20                  25                  30

Ile Ile Ala Thr Lys Asn Gly Lys Val Arg Gly Met Asn Leu Thr Val
            35                  40                  45

Phe Gly Gly Thr Val Thr Ala Phe Leu Gly Ile Pro Tyr Ala Gln Pro
50                  55                  60

Pro Leu Gly Arg Leu Arg Phe Lys Lys Pro Gln Ser Leu Thr Lys Trp
65                  70                  75                  80

Ser Asp Ile Trp Asn Ala Thr Lys Tyr Ala Asn Ser Cys Cys Gln Asn
                85                  90                  95

Ile Asp Gln Ser Phe Pro Gly Phe His Gly Ser Glu Met Trp Asn Pro
                100                 105                 110

Asn Thr Asp Leu Ser Glu Asp Cys Leu Tyr Leu Asn Val Trp Ile Pro
            115                 120                 125

Ala Pro Lys Pro Lys Asn Ala Thr Val Leu Ile Trp Ile Tyr Gly Gly
            130                 135                 140

Gly Phe Gln Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
```

```
                    165                 170                 175
Gly Ala Leu Gly Phe Leu Ala Leu Pro Gly Asn Pro Glu Ala Pro Gly
                180                 185                 190

Asn Met Gly Leu Phe Asp Gln Gln Leu Ala Leu Gln Trp Val Gln Lys
            195                 200                 205

Asn Ile Ala Ala Phe Gly Gly Asn Pro Lys Ser Val Thr Leu Phe Gly
        210                 215                 220

Glu Ser Ala Gly Ala Ala Ser Val Ser Leu His Leu Leu Ser Pro Gly
225                 230                 235                 240

Ser His Ser Leu Phe Thr Arg Ala Ile Leu Gln Ser Gly Ser Phe Asn
                245                 250                 255

Ala Pro Trp Ala Val Thr Ser Leu Tyr Glu Ala Arg Asn Arg Thr Leu
            260                 265                 270

Asn Leu Ala Lys Leu Thr Gly Cys Ser Arg Glu Asn Glu Thr Glu Ile
        275                 280                 285

Ile Lys Cys Leu Arg Asn Lys Asp Pro Gln Glu Ile Leu Leu Asn Glu
290                 295                 300

Ala Phe Val Val Pro Tyr Gly Thr Pro Leu Ser His Asn Phe Asp Pro
305                 310                 315                 320

Thr Val Asp Gly Asp Phe Leu Thr Asp Met Pro Asp Ile Leu Leu Glu
                325                 330                 335

Leu Gly Gln Phe Lys Lys Thr Gln Ile Leu Val Gly Val Asn Lys Asp
            340                 345                 350

Glu Gly Thr Ala Phe Leu Val Tyr Gly Ala Pro Gly Phe Ser Lys Asp
        355                 360                 365

Asn Asn Ser Ile Ile Thr Arg Lys Glu Phe Gln Glu Gly Leu Lys Ile
370                 375                 380

Phe Phe Pro Gly Val Ser Glu Phe Gly Lys Glu Ser Ile Leu Phe His
385                 390                 395                 400

Tyr Thr Asp Trp Val Asp Asp Gln Arg Pro Glu Asn Tyr Arg Glu Ala
                405                 410                 415

Leu Gly Asp Val Val Gly Asp Tyr Asn Phe Ile Cys Pro Ala Leu Glu
            420                 425                 430

Phe Thr Lys Lys Phe Ser Glu Trp Gly Asn Asn Ala Phe Phe Tyr Tyr
        435                 440                 445

Phe Glu His Arg Ser Ser Lys Leu Pro Trp Pro Glu Trp Met Gly Val
450                 455                 460

Met His Gly Tyr Glu Ile Glu Phe Val Phe Gly Leu Pro Leu Glu Arg
465                 470                 475                 480

Arg Asp Asn Tyr Thr Lys Ala Glu Glu Ile Leu Ser Arg Ser Ile Val
                485                 490                 495

Lys Arg Trp Ala Asn Phe Ala Lys Tyr Gly Asn Pro Asn Glu Thr Gln
            500                 505                 510

Asn Asn Ser Thr Ser Trp Pro Val Phe Lys Ser Thr Glu Gln Lys Tyr
        515                 520                 525

Leu Thr Leu Asn Thr Glu Ser Thr Arg Ile Met Thr Lys Leu Arg Ala
    530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
            580                 585                 590
```

Thr Ser Lys Lys Glu Ser Cys Val Gly Leu
        595             600

(2) INFORMATION FOR SEQ ID NO:13:

(i) SEQUENCE CHARACTERISTICS:
        (A) LENGTH: 602 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:13:

Met His Ser Lys Val Thr Ile Ile Cys Ile Arg Phe Leu Phe Trp Phe
1               5                   10                  15

Leu Leu Leu Cys Met Leu Ile Gly Lys Ser His Thr Glu Asp Asp Ile
            20                  25                  30

Ile Ile Ala Thr Lys Asn Gly Lys Val Arg Gly Met Asn Leu Thr Val
        35                  40                  45

Phe Gly Gly Thr Val Thr Ala Phe Leu Gly Ile Pro Tyr Ala Gln Pro
    50                  55                  60

Pro Leu Gly Arg Leu Arg Phe Lys Lys Pro Gln Ser Leu Thr Lys Trp
65                  70                  75                  80

Ser Asp Ile Trp Asn Ala Thr Lys Tyr Ala Asn Ser Cys Cys Gln Asn
                85                  90                  95

Ile Asp Gln Ser Phe Pro Gly Phe His Gly Ser Glu Met Trp Asn Pro
                100                 105                 110

Asn Thr Asp Leu Ser Glu Asp Cys Leu Tyr Leu Asn Val Trp Ile Pro
            115                 120                 125

Ala Pro Lys Pro Lys Asn Ala Thr Val Leu Ile Trp Ile Tyr Gly Gly
        130                 135                 140

Gly Phe His Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
                165                 170                 175

Gly Ala Leu Gly Phe Leu Ala Leu Pro Gly Asn Pro Glu Ala Pro Gly
            180                 185                 190

Asn Met Gly Leu Phe Asp Gln Gln Leu Ala Leu Gln Trp Val Gln Lys
        195                 200                 205

Asn Ile Ala Ala Phe Gly Gly Asn Pro Lys Ser Val Thr Leu Phe Gly
    210                 215                 220

Glu Ser Ala Gly Ala Ala Ser Val Ser Leu His Leu Leu Ser Pro Gly
225                 230                 235                 240

Ser His Ser Leu Phe Thr Arg Ala Ile Leu Gln Ser Gly Ser Phe Asn
                245                 250                 255

Ala Pro Trp Ala Val Thr Ser Leu Tyr Glu Ala Arg Asn Arg Thr Leu
            260                 265                 270

Asn Leu Ala Lys Leu Thr Gly Cys Ser Arg Glu Asn Glu Thr Glu Ile
        275                 280                 285

```
Ile Lys Cys Leu Arg Asn Lys Asp Pro Gln Glu Ile Leu Leu Asn Glu
290                 295                 300

Ala Phe Val Val Pro Tyr Gly Thr Pro Leu Ser Val Asn Phe Gly Pro
305                 310                 315                 320

Thr Val Asp Gly Asp Phe Leu Thr Asp Met Pro Asp Ile Leu Leu Glu
                325                 330                 335

Leu Gly Gln Phe Lys Lys Thr Gln Ile Leu Val Gly Val Asn Lys Asp
                340                 345                 350

Glu Gly Thr Ala Phe Leu Val Tyr Gly Ala Pro Gly Phe Ser Lys Asp
            355                 360                 365

Asn Asn Ser Ile Ile Thr Arg Lys Glu Phe Gln Glu Gly Leu Lys Ile
370                 375                 380

Phe Phe Pro Gly Val Ser Glu Phe Gly Lys Glu Ser Ile Leu Phe His
385                 390                 395                 400

Tyr Thr Asp Trp Val Asp Asp Gln Arg Pro Glu Asn Tyr Arg Glu Ala
                405                 410                 415

Leu Gly Asp Val Val Gly Asp Tyr Asn Phe Ile Cys Pro Ala Leu Glu
                420                 425                 430

Phe Thr Lys Lys Phe Ser Glu Trp Gly Asn Asn Ala Phe Phe Tyr Tyr
            435                 440                 445

Phe Glu His Arg Ser Ser Lys Leu Pro Trp Pro Glu Trp Met Gly Val
450                 455                 460

Met His Gly Tyr Glu Ile Glu Phe Val Phe Gly Leu Pro Leu Glu Arg
465                 470                 475                 480

Arg Asp Asn Tyr Thr Lys Ala Glu Glu Ile Leu Ser Arg Ser Ile Val
                485                 490                 495

Lys Arg Trp Ala Asn Phe Ala Lys Tyr Gly Asn Pro Asn Glu Thr Gln
                500                 505                 510

Asn Asn Ser Thr Ser Trp Pro Val Phe Lys Ser Thr Glu Gln Lys Tyr
            515                 520                 525

Leu Thr Leu Asn Thr Glu Ser Thr Arg Ile Met Thr Lys Leu Arg Ala
530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
                580                 585                 590

Thr Ser Lys Lys Glu Ser Cys Val Gly Leu
            595                 600
```

(2) INFORMATION FOR SEQ ID NO:14:

(i) SEQUENCE CHARACTERISTICS:
        (A) LENGTH: 602 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:14:

```
Met His Ser Lys Val Thr Ile Ile Cys Ile Arg Phe Leu Phe Trp Phe
1               5                   10                  15

Leu Leu Leu Cys Met Leu Ile Gly Lys Ser His Thr Glu Asp Asp Ile
            20                  25                  30

Ile Ile Ala Thr Lys Asn Gly Lys Val Arg Gly Met Asn Leu Thr Val
        35                  40                  45

Phe Gly Gly Thr Val Thr Ala Phe Leu Gly Ile Pro Tyr Ala Gln Pro
    50                  55                  60

Pro Leu Gly Arg Leu Arg Phe Lys Lys Pro Gln Ser Leu Thr Lys Trp
65                  70                  75                  80

Ser Asp Ile Trp Asn Ala Thr Lys Tyr Ala Asn Ser Cys Cys Gln Asn
                85                  90                  95

Ile Asp Gln Ser Phe Pro Gly Phe His Gly Ser Glu Met Trp Asn Pro
            100                 105                 110

Asn Thr Asp Leu Ser Glu Asp Cys Leu Tyr Leu Asn Val Trp Ile Pro
        115                 120                 125

Ala Pro Lys Pro Lys Asn Ala Thr Val Leu Ile Trp Ile Tyr Gly Gly
    130                 135                 140

Gly Phe His Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
                165                 170                 175

Gly Ala Leu Gly Phe Leu Ala Leu Pro Gly Asn Pro Glu Ala Pro Gly
            180                 185                 190

Asn Met Gly Leu Phe Asp Gln Gln Leu Ala Leu Gln Trp Val Gln Lys
        195                 200                 205

Asn Ile Ala Ala Phe Gly Gly Asn Pro Lys Ser Val Thr Leu Phe Gly
    210                 215                 220

Glu Ser Ala Gly Ala Ala Ser Val Ser Leu His Leu Leu Ser Pro Gly
225                 230                 235                 240

Ser His Ser Leu Phe Thr Arg Ala Ile Leu Gln Ser Gly Ser Phe Asn
                245                 250                 255

Ala Pro Trp Ala Val Thr Ser Leu Tyr Glu Ala Arg Asn Arg Thr Leu
            260                 265                 270

Asn Leu Ala Lys Leu Thr Gly Cys Ser Arg Glu Asn Glu Thr Glu Ile
        275                 280                 285

Ile Lys Cys Leu Arg Asn Lys Asp Pro Gln Glu Ile Leu Leu Asn Glu
    290                 295                 300

Ala Phe Val Val Pro Tyr Gly Thr Pro Leu Ser Glu Asn Phe Gly Pro
305                 310                 315                 320

Thr Val Asp Gly Asp Phe Leu Thr Asp Met Pro Asp Ile Leu Leu Glu
                325                 330                 335

Leu Gly Gln Phe Lys Lys Thr Gln Ile Leu Val Gly Val Asn Lys Asp
            340                 345                 350

Glu Gly Thr Ala Phe Leu Val Tyr Gly Ala Pro Gly Phe Ser Lys Asp
        355                 360                 365

Asn Asn Ser Ile Ile Thr Arg Lys Glu Phe Gln Glu Gly Leu Lys Ile
    370                 375                 380

Phe Phe Pro Gly Val Ser Glu Phe Gly Lys Glu Ser Ile Leu Phe His
385                 390                 395                 400

Tyr Thr Asp Trp Val Asp Asp Gln Arg Pro Glu Asn Tyr Arg Glu Ala
                405                 410                 415
```

```
Leu Gly Asp Val Val Gly Asp Tyr Asn Phe Ile Cys Pro Ala Leu Glu
            420                 425                 430

Phe Thr Lys Lys Phe Ser Glu Trp Gly Asn Asn Ala Phe Phe Tyr Tyr
            435                 440                 445

Phe Glu His Arg Ser Ser Lys Leu Pro Trp Pro Glu Trp Met Gly Val
            450                 455                 460

Met His Gly Tyr Glu Ile Glu Phe Val Phe Gly Leu Pro Leu Glu Arg
465                 470                 475                 480

Arg Asp Asn Tyr Thr Lys Ala Glu Glu Ile Leu Ser Arg Ser Ile Val
            485                 490                 495

Lys Arg Trp Ala Asn Phe Ala Lys Tyr Gly Asn Pro Asn Glu Thr Gln
            500                 505                 510

Asn Asn Ser Thr Ser Trp Pro Val Phe Lys Ser Thr Glu Gln Lys Tyr
            515                 520                 525

Leu Thr Leu Asn Thr Glu Ser Thr Arg Ile Met Thr Lys Leu Arg Ala
            530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
            565                 570                 575

Arg Trp Asn Asn Tyr Met Met Asp Trp Lys Asn Gln Phe Asn Asp Tyr
            580                 585                 590

Thr Ser Lys Lys Glu Ser Cys Val Gly Leu
            595                 600

(2) INFORMATION FOR SEQ ID NO:15:

(i) SEQUENCE CHARACTERISTICS:
        (A) LENGTH: 602 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:15:

Met His Ser Lys Val Thr Ile Ile Cys Ile Arg Phe Leu Phe Trp Phe
1               5                   10                  15

Leu Leu Leu Cys Met Leu Ile Gly Lys Ser His Thr Glu Asp Asp Ile
            20                  25                  30

Ile Ile Ala Thr Lys Asn Gly Lys Val Arg Gly Met Asn Leu Thr Val
            35                  40                  45

Phe Gly Gly Thr Val Thr Ala Phe Leu Gly Ile Pro Tyr Ala Gln Pro
50                  55                  60

Pro Leu Gly Arg Leu Arg Phe Lys Lys Pro Gln Ser Leu Thr Lys Trp
65                  70                  75                  80

Ser Asp Ile Trp Asn Ala Thr Lys Tyr Ala Asn Ser Cys Cys Gln Asn
            85                  90                  95

Ile Asp Gln Ser Phe Pro Gly Phe His Gly Ser Glu Met Trp Asn Pro
            100                 105                 110
```

-continued

```
Asn Thr Asp Leu Ser Glu Asp Cys Leu Tyr Leu Asn Val Trp Ile Pro
            115                 120                 125
Ala Pro Lys Pro Lys Asn Ala Thr Val Leu Ile Trp Ile Tyr Gly Gly
        130                 135                 140
Gly Phe Asp Thr Gly Thr Ser Ser Leu His Val Tyr Asp Gly Lys Phe
145                 150                 155                 160
Leu Ala Arg Val Glu Arg Val Ile Val Val Ser Met Asn Tyr Arg Val
                165                 170                 175
Gly Ala Leu Gly Phe Leu Ala Leu Pro Gly Asn Pro Glu Ala Pro Gly
            180                 185                 190
Asn Met Gly Leu Phe Asp Gln Gln Leu Ala Leu Gln Trp Val Gln Lys
        195                 200                 205
Asn Ile Ala Ala Phe Gly Gly Asn Pro Lys Ser Val Thr Leu Phe Gly
    210                 215                 220
Glu Ser Ala Gly Ala Ala Ser Val Ser Leu His Leu Leu Ser Pro Gly
225                 230                 235                 240
Ser His Ser Leu Phe Thr Arg Ala Ile Leu Gln Ser Gly Ser Phe Asn
                245                 250                 255
Ala Pro Trp Ala Val Thr Ser Leu Tyr Glu Ala Arg Asn Arg Thr Leu
            260                 265                 270
Asn Leu Ala Lys Leu Thr Gly Cys Ser Arg Glu Asn Glu Thr Glu Ile
        275                 280                 285
Ile Lys Cys Leu Arg Asn Lys Asp Pro Gln Glu Ile Leu Leu Asn Glu
    290                 295                 300
Ala Phe Val Val Pro Tyr Gly Thr Pro Leu Ser His Asn Phe Gly Pro
305                 310                 315                 320
Thr Val Asp Gly Asp Phe Leu Thr Asp Met Pro Asp Ile Leu Leu Glu
                325                 330                 335
Leu Gly Gln Phe Lys Lys Thr Gln Ile Leu Val Gly Val Asn Lys Asp
            340                 345                 350
Glu Gly Thr Ala Phe Leu Val Tyr Gly Ala Pro Gly Phe Ser Lys Asp
        355                 360                 365
Asn Asn Ser Ile Ile Thr Arg Lys Glu Phe Gln Glu Gly Leu Lys Ile
    370                 375                 380
Phe Phe Pro Gly Val Ser Glu Phe Gly Lys Glu Ser Ile Leu Phe His
385                 390                 395                 400
Tyr Thr Asp Trp Val Asp Asp Gln Arg Pro Glu Asn Tyr Arg Glu Ala
                405                 410                 415
Leu Gly Asp Val Val Gly Asp Tyr Asn Phe Ile Cys Pro Ala Leu Glu
            420                 425                 430
Phe Thr Lys Lys Phe Ser Glu Trp Gly Asn Asn Ala Phe Phe Tyr Tyr
        435                 440                 445
Phe Glu His Arg Ser Ser Lys Leu Pro Trp Pro Glu Trp Met Gly Val
    450                 455                 460
Met His Gly Tyr Glu Ile Glu Phe Val Phe Gly Leu Pro Leu Glu Arg
465                 470                 475                 480
Arg Asp Asn Tyr Thr Lys Ala Glu Glu Ile Leu Ser Arg Ser Ile Val
                485                 490                 495
Lys Arg Trp Ala Asn Phe Ala Lys Tyr Gly Asn Pro Asn Glu Thr Gln
            500                 505                 510
Asn Asn Ser Thr Ser Trp Pro Val Phe Lys Ser Thr Glu Gln Lys Tyr
        515                 520                 525
Leu Thr Leu Asn Thr Glu Ser Thr Arg Ile Met Thr Lys Leu Arg Ala
```

```
               530                 535                 540
Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
                580                 585                 590

Thr Ser Lys Lys Glu Ser Cys Val Gly Leu
            595                 600
```

(2) INFORMATION FOR SEQ ID NO:16:

(i) SEQUENCE CHARACTERISTICS:
        (A) LENGTH: 602 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:16:

```
Met His Ser Lys Val Thr Ile Ile Cys Ile Arg Phe Leu Phe Trp Phe
1               5                  10                  15

Leu Leu Leu Cys Met Leu Ile Gly Lys Ser His Thr Glu Asp Asp Ile
                20                  25                  30

Ile Ile Ala Thr Lys Asn Gly Lys Val Arg Gly Met Asn Leu Thr Val
                35                  40                  45

Phe Gly Gly Thr Val Thr Ala Phe Leu Gly Ile Pro Tyr Ala Gln Pro
50                  55                  60

Pro Leu Gly Arg Leu Arg Phe Lys Lys Pro Gln Ser Leu Thr Lys Trp
65                  70                  75                  80

Ser Asp Ile Trp Asn Ala Thr Lys Tyr Ala Asn Ser Cys Cys Gln Asn
                85                  90                  95

Ile Asp Gln Ser Phe Pro Gly Phe His Gly Ser Glu Met Trp Asn Pro
                100                 105                 110

Asn Thr Asp Leu Ser Glu Asp Cys Leu Tyr Leu Asn Val Trp Ile Pro
                115                 120                 125

Ala Pro Lys Pro Lys Asn Ala Thr Val Leu Ile Trp Ile Tyr Gly Gly
                130                 135                 140

Gly Phe Asp Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
                165                 170                 175

Gly Ala Leu Gly Phe Leu Ala Leu Pro Gly Asn Pro Glu Ala Pro Gly
                180                 185                 190

Asn Met Gly Leu Phe Asp Gln Gln Leu Ala Leu Gln Trp Val Gln Lys
                195                 200                 205

Asn Ile Ala Ala Phe Gly Gly Asn Pro Lys Ser Val Thr Leu Phe Gly
                210                 215                 220

Glu Ser Ala Gly Ala Ala Ser Val Ser Leu His Leu Leu Ser Pro Gly
```

```
                225                 230                 235                 240
Ser His Ser Leu Phe Thr Arg Ala Ile Leu Gln Ser Gly Ser Phe Asn
                    245                 250                 255

Ala Pro Trp Ala Val Thr Ser Leu Tyr Glu Ala Arg Asn Arg Thr Leu
            260                 265                 270

Asn Leu Ala Lys Leu Thr Gly Cys Ser Arg Glu Asn Glu Thr Glu Ile
        275                 280                 285

Ile Lys Cys Leu Arg Asn Lys Asp Pro Gln Glu Ile Leu Leu Asn Glu
    290                 295                 300

Ala Phe Val Val Pro Tyr Gly Thr Pro Leu Ser His Asn Phe Gly Pro
305                 310                 315                 320

Thr Val Asp Gly Asp Phe Leu Thr Asp Met Pro Asp Ile Leu Leu Glu
                325                 330                 335

Leu Gly Gln Phe Lys Lys Thr Gln Ile Leu Val Gly Val Asn Lys Asp
            340                 345                 350

Glu Gly Thr Ala Phe Leu Val Tyr Gly Ala Pro Gly Phe Ser Lys Asp
        355                 360                 365

Asn Asn Ser Ile Ile Thr Arg Lys Glu Phe Gln Glu Gly Leu Lys Ile
    370                 375                 380

Phe Phe Pro Gly Val Ser Glu Phe Gly Lys Glu Ser Ile Leu Phe His
385                 390                 395                 400

Tyr Thr Asp Trp Val Asp Asp Gln Arg Pro Glu Asn Tyr Arg Glu Ala
                405                 410                 415

Leu Gly Asp Val Val Gly Asp Tyr Asn Phe Ile Cys Pro Ala Leu Glu
            420                 425                 430

Phe Thr Lys Lys Phe Ser Glu Trp Gly Asn Asn Ala Phe Phe Tyr Tyr
        435                 440                 445

Phe Glu His Arg Ser Ser Lys Leu Pro Trp Pro Glu Trp Met Gly Val
    450                 455                 460

Met His Gly Tyr Glu Ile Glu Phe Val Phe Gly Leu Pro Leu Glu Arg
465                 470                 475                 480

Arg Asp Asn Tyr Thr Lys Ala Glu Glu Ile Leu Ser Arg Ser Ile Val
                485                 490                 495

Lys Arg Trp Ala Asn Phe Ala Lys Tyr Gly Asn Pro Asn Glu Thr Gln
            500                 505                 510

Asn Asn Ser Thr Ser Trp Pro Val Phe Lys Ser Thr Glu Gln Lys Tyr
        515                 520                 525

Leu Thr Leu Asn Thr Glu Ser Thr Arg Ile Met Thr Lys Leu Arg Ala
    530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
            580                 585                 590

Thr Ser Lys Lys Glu Ser Cys Val Gly Leu
        595                 600

(2) INFORMATION FOR SEQ ID NO:17:

(i) SEQUENCE CHARACTERISTICS:
        (A) LENGTH: 602 amino acids
        (B) TYPE: amino acid
        (C) STRANDEDNESS: single
        (D) TOPOLOGY: unknown
```

(ii) MOLECULE TYPE: protein (iii) HYPOTHETICAL: YES (iv) ANTI-SENSE: YES (v) FRAGMENT TYPE: N-terminal (vi) ORIGINAL SOURCE:
     (A) ORGANISM: human esterases (xi) SEQUENCE DESCRIPTION: SEQ ID NO:17:

```
Met His Ser Lys Val Thr Ile Ile Cys Ile Arg Phe Leu Phe Trp Phe
1               5                   10                  15
Leu Leu Leu Cys Met Leu Ile Gly Lys Ser His Thr Glu Asp Asp Ile
            20                  25                  30
Ile Ile Ala Thr Lys Asn Gly Lys Val Arg Gly Met Asn Leu Thr Val
        35                  40                  45
Phe Gly Gly Thr Val Thr Ala Phe Leu Gly Ile Pro Tyr Ala Gln Pro
    50                  55                  60
Pro Leu Gly Arg Leu Arg Phe Lys Lys Pro Gln Ser Leu Thr Lys Trp
65                  70                  75                  80
Ser Asp Ile Trp Asn Ala Thr Lys Tyr Ala Asn Ser Cys Cys Gln Asn
                85                  90                  95
Ile Asp Gln Ser Phe Pro Gly Phe His Gly Ser Glu Met Trp Asn Pro
            100                 105                 110
Asn Thr Asp Leu Ser Glu Asp Cys Leu Tyr Leu Asn Val Trp Ile Pro
        115                 120                 125
Ala Pro Lys Pro Lys Asn Ala Thr Val Leu Ile Trp Ile Tyr Gly Gly
    130                 135                 140
Gly Phe Gln Thr Gly Thr Ser Ser Leu His Val Tyr Asp Gly Lys Phe
145                 150                 155                 160
Leu Ala Arg Val Glu Arg Val Ile Val Val Ser Met Asn Tyr Arg Val
                165                 170                 175
Gly Ala Leu Gly Phe Leu Ala Leu Pro Gly Asn Pro Glu Ala Pro Gly
            180                 185                 190
Asn Met Gly Leu Phe Asp Gln Gln Leu Ala Leu Gln Trp Val Gln Lys
        195                 200                 205
Asn Ile Ala Ala Phe Gly Gly Asn Pro Lys Ser Val Thr Leu Phe Gly
    210                 215                 220
Glu Ser Ala Gly Ala Ala Ser Val Ser Leu His Leu Leu Ser Pro Gly
225                 230                 235                 240
Ser His Ser Leu Phe Thr Arg Ala Ile Leu Gln Ser Gly Ser Phe Asn
                245                 250                 255
Ala Pro Trp Ala Val Thr Ser Leu Tyr Glu Ala Arg Asn Arg Thr Leu
            260                 265                 270
Asn Leu Ala Lys Leu Thr Gly Cys Ser Arg Glu Asn Glu Thr Glu Ile
        275                 280                 285
Ile Lys Cys Leu Arg Asn Lys Asp Pro Gln Glu Ile Leu Leu Asn Glu
    290                 295                 300
Asp Phe Val Val Pro Tyr Gly Thr Pro Leu Ser His Asn Phe Gly Pro
305                 310                 315                 320
Thr Val Asp Gly Asp Phe Leu Thr Asp Met Pro Asp Ile Leu Leu Glu
                325                 330                 335
Leu Gly Gln Phe Lys Lys Thr Gln Ile Leu Val Gly Val Asn Lys Asp
            340                 345                 350
```

```
Glu Gly Thr Ala Phe Leu Val Tyr Gly Ala Pro Gly Phe Ser Lys Asp
            355                 360                 365

Asn Asn Ser Ile Ile Thr Arg Lys Glu Phe Gln Glu Gly Leu Lys Ile
        370                 375                 380

Phe Phe Pro Gly Val Ser Glu Phe Gly Lys Glu Ser Ile Leu Phe His
385                 390                 395                 400

Tyr Thr Asp Trp Val Asp Asp Gln Arg Pro Glu Asn Tyr Arg Glu Ala
                405                 410                 415

Leu Gly Asp Val Val Gly Asp Tyr Asn Phe Ile Cys Pro Ala Leu Glu
            420                 425                 430

Phe Thr Lys Lys Phe Ser Glu Trp Gly Asn Asn Ala Phe Phe Tyr Tyr
            435                 440                 445

Phe Glu His Arg Ser Ser Lys Leu Pro Trp Pro Glu Trp Met Gly Val
            450                 455                 460

Met His Gly Tyr Glu Ile Glu Phe Val Phe Gly Leu Pro Leu Glu Arg
465                 470                 475                 480

Arg Asp Asn Tyr Thr Lys Ala Glu Glu Ile Leu Ser Arg Ser Ile Val
                485                 490                 495

Lys Arg Trp Ala Asn Phe Ala Lys Tyr Gly Asn Pro Asn Glu Thr Gln
            500                 505                 510

Asn Asn Ser Thr Ser Trp Pro Val Phe Lys Ser Thr Glu Gln Lys Tyr
            515                 520                 525

Leu Thr Leu Asn Thr Glu Ser Thr Arg Ile Met Thr Lys Leu Arg Ala
            530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
                580                 585                 590

Thr Ser Lys Lys Glu Ser Cys Val Gly Leu
            595                 600
```

(2) INFORMATION FOR SEQ ID NO:18:

(i) SEQUENCE CHARACTERISTICS:
        (A) LENGTH: 602 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:18:

```
Met His Ser Lys Val Thr Ile Ile Cys Ile Arg Phe Leu Phe Trp Phe
1                   5                   10                  15

Leu Leu Leu Cys Met Leu Ile Gly Lys Ser His Thr Glu Asp Asp Ile
                20                  25                  30

Ile Ile Ala Thr Lys Asn Gly Lys Val Arg Gly Met Asn Leu Thr Val
                35                  40                  45
```

```
Phe Gly Gly Thr Val Thr Ala Phe Leu Gly Ile Pro Tyr Ala Gln Pro
     50                  55                  60

Pro Leu Gly Arg Leu Arg Phe Lys Lys Pro Gln Ser Leu Thr Lys Trp
 65                  70                  75                  80

Ser Asp Ile Trp Asn Ala Thr Lys Tyr Ala Asn Ser Cys Cys Gln Asn
                 85                  90                  95

Ile Asp Gln Ser Phe Pro Gly Phe His Gly Ser Glu Met Trp Asn Pro
                100                 105                 110

Asn Thr Asp Leu Ser Glu Asp Cys Leu Tyr Leu Asn Val Trp Ile Pro
            115                 120                 125

Ala Pro Lys Pro Lys Asn Ala Thr Val Leu Ile Trp Ile Tyr Gly Gly
        130                 135                 140

Gly Phe Gln Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
                165                 170                 175

Gly Ala Leu Gly Phe Leu Ala Leu Pro Gly Asn Pro Glu Ala Pro Gly
            180                 185                 190

Asn Met Gly Leu Phe Asp Gln Leu Ala Leu Gln Trp Val Gln Lys
        195                 200                 205

Asn Ile Ala Ala Phe Gly Gly Asn Pro Lys Ser Val Thr Leu Phe Gly
210                 215                 220

Glu Ser Ala Gly Ala Ala Ser Val Ser Leu His Leu Leu Ser Pro Gly
225                 230                 235                 240

Ser His Ser Leu Phe Thr Arg Ala Ile Leu Gln Ser Gly Ser Phe Asn
                245                 250                 255

Ala Pro Trp Ala Val Thr Ser Leu Tyr Glu Ala Arg Asn Arg Thr Leu
            260                 265                 270

Asn Leu Ala Lys Leu Thr Gly Cys Ser Arg Glu Asn Glu Thr Glu Ile
        275                 280                 285

Ile Lys Cys Leu Arg Asn Lys Asp Pro Gln Glu Ile Leu Leu Asn Glu
    290                 295                 300

Glu Phe Val Val Pro Tyr Gly Thr Pro Leu Ser His Asn Phe Gly Pro
305                 310                 315                 320

Thr Val Asp Gly Asp Phe Leu Thr Asp Met Pro Asp Ile Leu Leu Glu
                325                 330                 335

Leu Gly Gln Phe Lys Lys Thr Gln Ile Leu Val Gly Val Asn Lys Asp
            340                 345                 350

Glu Gly Thr Ala Phe Leu Val Tyr Gly Ala Pro Gly Phe Ser Lys Asp
        355                 360                 365

Asn Asn Ser Ile Ile Thr Arg Lys Glu Phe Gln Glu Gly Leu Lys Ile
    370                 375                 380

Phe Phe Pro Gly Val Ser Glu Phe Gly Lys Glu Ser Ile Leu Phe His
385                 390                 395                 400

Tyr Thr Asp Trp Val Asp Asp Gln Arg Pro Glu Asn Tyr Arg Glu Ala
                405                 410                 415

Leu Gly Asp Val Val Gly Asp Tyr Asn Phe Ile Cys Pro Ala Leu Glu
            420                 425                 430

Phe Thr Lys Lys Phe Ser Glu Trp Gly Asn Asn Ala Phe Phe Tyr Tyr
        435                 440                 445

Phe Glu His Arg Ser Ser Lys Leu Pro Trp Pro Glu Trp Met Gly Val
    450                 455                 460

Met His Gly Tyr Glu Ile Glu Phe Val Phe Gly Leu Pro Leu Glu Arg
465                 470                 475                 480
```

```
Arg Asp Asn Tyr Thr Lys Ala Glu Glu Ile Leu Ser Arg Ser Ile Val
                485                 490                 495

Lys Arg Trp Ala Asn Phe Ala Lys Tyr Gly Asn Pro Asn Glu Thr Gln
            500                 505                 510

Asn Asn Ser Thr Ser Trp Pro Val Phe Lys Ser Thr Glu Gln Lys Tyr
            515                 520                 525

Leu Thr Leu Asn Thr Glu Ser Thr Arg Ile Met Thr Lys Leu Arg Ala
            530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
                580                 585                 590

Thr Ser Lys Lys Glu Ser Cys Val Gly Leu
                595                 600

(2) INFORMATION FOR SEQ ID NO:19:

(i) SEQUENCE CHARACTERISTICS:
        (A) LENGTH: 614 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:19:

Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Val Gly Ala Glu
            20                  25                  30

Gly Arg Glu Asp Ala Glu Leu Leu Val Thr Val Arg Gly Gly Arg Leu
            35                  40                  45

Arg Gly Ile Arg Leu Lys Thr Pro Gly Gly Pro Val Ser Ala Phe Leu
        50                  55                  60

Gly Ile Pro Phe Ala Glu Pro Pro Met Gly Pro Arg Arg Phe Leu Pro
65                  70                  75                  80

Pro Glu Pro Lys Gln Pro Trp Ser Gly Val Val Asp Ala Thr Thr Phe
                85                  90                  95

Gln Ser Val Cys Tyr Gln Tyr Val Asp Thr Leu Tyr Pro Gly Phe Glu
            100                 105                 110

Gly Thr Glu Met Trp Asn Pro Asn Arg Glu Leu Ser Glu Asp Cys Leu
            115                 120                 125

Tyr Leu Asn Val Trp Thr Pro Tyr Pro Arg Pro Thr Ser Pro Thr Pro
        130                 135                 140

Val Leu Val Trp Ile Tyr Gly Gly Phe Tyr Ser Gly Ala Ser Ser
145                 150                 155                 160

Leu Asp Val Tyr Asp Gly Arg Phe Leu Val Gln Ala Glu Arg Thr Val
                165                 170                 175
```

```
Leu Val Ser Met Asn Tyr Arg Val Gly Ala Phe Gly Phe Leu Ala Leu
            180                 185                 190

Pro Gly Ser Arg Glu Ala Pro Gly Asn Val Gly Leu Leu Asp Gln Arg
            195                 200                 205

Leu Ala Leu Gln Trp Val Gln Glu Asn Val Ala Ala Phe Gly Gly Asp
            210                 215                 220

Pro Thr Ser Val Thr Leu Phe Gly Glu Ser Ala Gly Ala Ala Ser Val
225                 230                 235                 240

Gly Met His Leu Leu Ser Pro Pro Ser Arg Gly Leu Phe His Arg Ala
                245                 250                 255

Val Leu Gln Ser Gly Ala Pro Asn Gly Pro Trp Ala Thr Val Gly Met
            260                 265                 270

Gly Glu Ala Arg Arg Arg Ala Thr Gln Leu Ala His Leu Val Gly Cys
            275                 280                 285

Pro Pro Gly Gly Thr Gly Gly Asn Asp Thr Glu Leu Val Ala Cys Leu
            290                 295                 300

Arg Thr Arg Pro Ala Gln Val Leu Val Asn His Glu Trp His Val Leu
305                 310                 315                 320

Pro Gln Glu Ser Val Phe Arg Phe Ser Phe Val Pro Val Val Asp Gly
                325                 330                 335

Asp Phe Leu Ser Asp Thr Pro Glu Ala Leu Ile Asn Ala Gly Asp Phe
            340                 345                 350

His Gly Leu Gln Val Leu Val Gly Val Val Lys Asp Glu Gly Ser Tyr
            355                 360                 365

Phe Leu Val Tyr Gly Ala Pro Gly Phe Ser Lys Asp Asn Glu Ser Leu
            370                 375                 380

Ile Ser Arg Ala Glu Phe Leu Ala Gly Val Arg Val Gly Val Pro Gln
385                 390                 395                 400

Val Ser Asp Leu Ala Ala Glu Ala Val Val Leu His Tyr Thr Asp Trp
                405                 410                 415

Leu His Pro Glu Asp Pro Ala Arg Leu Arg Glu Ala Leu Ser Asp Val
            420                 425                 430

Val Gly Asp His Asn Val Val Cys Pro Val Ala Gln Leu Ala Gly Arg
            435                 440                 445

Leu Ala Ala Gln Gly Ala Arg Val Tyr Ala Tyr Val Phe Glu His Arg
            450                 455                 460

Ala Ser Thr Leu Ser Trp Pro Leu Trp Met Gly Val Pro His Gly Tyr
465                 470                 475                 480

Glu Ile Glu Phe Ile Phe Gly Ile Pro Leu Asp Pro Ser Arg Asn Tyr
                485                 490                 495

Thr Ala Glu Glu Lys Ile Phe Ala Gln Arg Leu Met Arg Tyr Trp Ala
            500                 505                 510

Asn Phe Ala Arg Thr Gly Asp Pro Asn Glu Pro Arg Asp Pro Lys Ala
            515                 520                 525

Pro Gln Trp Pro Pro Tyr Thr Ala Gly Ala Gln Gln Tyr Val Ser Leu
            530                 535                 540

Asp Leu Arg Pro Leu Glu Val Arg Arg Gly Leu Arg Ala Gln Ala Cys
545                 550                 555                 560

Ala Phe Trp Asn Arg Phe Leu Pro Lys Leu Leu Ser Ala Thr Asp Thr
                565                 570                 575

Leu Asp Glu Ala Glu Arg Gln Trp Lys Ala Glu Phe His Arg Trp Ser
            580                 585                 590

Ser Tyr Met Val His Trp Lys Asn Gln Phe Asp His Tyr Ser Lys Gln
```

```
                595                 600                 605

Asp Arg Cys Ser Asp Leu
         610

(2) INFORMATION FOR SEQ ID NO:20:

(i) SEQUENCE CHARACTERISTICS:
        (A) LENGTH: 614 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:20:

Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Val Gly Ala Glu
            20                  25                  30

Gly Arg Glu Asp Ala Glu Leu Leu Val Thr Val Arg Gly Gly Arg Leu
        35                  40                  45

Arg Gly Ile Arg Leu Lys Thr Pro Gly Gly Pro Val Ser Ala Phe Leu
    50                  55                  60

Gly Ile Pro Phe Ala Glu Pro Pro Met Gly Pro Arg Arg Phe Leu Pro
65                  70                  75                  80

Pro Glu Pro Lys Gln Pro Trp Ser Gly Val Val Asp Ala Thr Thr Phe
                85                  90                  95

Gln Ser Val Cys Tyr Gln Tyr Val Asp Thr Leu Tyr Pro Gly Phe Glu
            100                 105                 110

Gly Thr Glu Met Trp Asn Pro Asn Arg Glu Leu Ser Glu Asp Cys Leu
        115                 120                 125

Tyr Leu Asn Val Trp Thr Pro Tyr Pro Arg Pro Thr Ser Pro Thr Pro
    130                 135                 140

Val Leu Val Trp Ile Tyr Gly Gly His Phe Tyr Ser Gly Ala Ser Ser
145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
            180                 185                 190

Pro Gly Ser Arg Glu Ala Pro Gly Asn Val Gly Leu Leu Asp Gln Arg
        195                 200                 205

Leu Ala Leu Gln Trp Val Gln Glu Asn Val Ala Ala Phe Gly Gly Asp
    210                 215                 220

Pro Thr Ser Val Thr Leu Phe Gly Glu Ser Ala Gly Ala Ala Ser Val
225                 230                 235                 240

Gly Met His Leu Leu Ser Pro Pro Ser Arg Gly Leu Phe His Arg Ala
                245                 250                 255

Val Leu Gln Ser Gly Ala Pro Asn Gly Pro Trp Ala Thr Val Gly Met
            260                 265                 270

Gly Glu Ala Arg Arg Arg Ala Thr Gln Leu Ala His Leu Val Gly Cys
```

```
                        275                 280                 285
Pro Pro Gly Gly Thr Gly Gly Asn Asp Thr Glu Leu Val Ala Cys Leu
    290                 295                 300

Arg Thr Arg Pro Ala Gln Val Leu Val Asn His Glu Trp His Val Leu
305                 310                 315                 320

Pro Gln Glu Ser Val Phe Arg Phe Ser Phe Val Pro Val Val Asp Gly
                325                 330                 335

Asp Phe Leu Ser Asp Thr Pro Glu Ala Leu Ile Asn Ala Gly Asp Phe
                340                 345                 350

His Gly Leu Gln Val Leu Val Gly Val Val Lys Asp Glu Gly Ser Tyr
            355                 360                 365

Phe Leu Val Tyr Gly Ala Pro Gly Phe Ser Lys Asp Asn Glu Ser Leu
    370                 375                 380

Ile Ser Arg Ala Glu Phe Leu Ala Gly Val Arg Val Gly Val Pro Gln
385                 390                 395                 400

Val Ser Asp Leu Ala Ala Glu Ala Val Val Leu His Tyr Thr Asp Trp
                405                 410                 415

Leu His Pro Glu Asp Pro Ala Arg Leu Arg Glu Ala Leu Ser Asp Val
                420                 425                 430

Val Gly Asp His Asn Val Val Cys Pro Val Ala Gln Leu Ala Gly Arg
            435                 440                 445

Leu Ala Ala Gln Gly Ala Arg Val Tyr Ala Tyr Val Phe Glu His Arg
    450                 455                 460

Ala Ser Thr Leu Ser Trp Pro Leu Trp Met Gly Val Pro His Gly Tyr
465                 470                 475                 480

Glu Ile Glu Phe Ile Phe Gly Ile Pro Leu Asp Pro Ser Arg Asn Tyr
                485                 490                 495

Thr Ala Glu Glu Lys Ile Phe Ala Gln Arg Leu Met Arg Tyr Trp Ala
                500                 505                 510

Asn Phe Ala Arg Thr Gly Asp Pro Asn Glu Pro Arg Asp Pro Lys Ala
            515                 520                 525

Pro Gln Trp Pro Pro Tyr Thr Ala Gly Ala Gln Gln Tyr Val Ser Leu
    530                 535                 540

Asp Leu Arg Pro Leu Glu Val Arg Arg Gly Leu Arg Ala Gln Ala Cys
545                 550                 555                 560

Ala Phe Trp Asn Arg Phe Leu Pro Lys Leu Leu Ser Ala Thr Asp Thr
                565                 570                 575

Leu Asp Glu Ala Glu Arg Gln Trp Lys Ala Glu Phe His Arg Trp Ser
                580                 585                 590

Ser Tyr Met Val His Trp Lys Asn Gln Phe Asp His Tyr Ser Lys Gln
            595                 600                 605

Asp Arg Cys Ser Asp Leu
    610
```

(2) INFORMATION FOR SEQ ID NO:21:

(i) SEQUENCE CHARACTERISTICS:
        (A) LENGTH: 614 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
    (A) ORGANISM: human esterases (xi) SEQUENCE DESCRIPTION: SEQ ID NO:21:

```
Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Val Gly Ala Glu
            20                  25                  30

Gly Arg Glu Asp Ala Glu Leu Leu Val Thr Val Arg Gly Gly Arg Leu
            35                  40                  45

Arg Gly Ile Arg Leu Lys Thr Pro Gly Gly Pro Val Ser Ala Phe Leu
50                  55                  60

Gly Ile Pro Phe Ala Glu Pro Pro Met Gly Pro Arg Arg Phe Leu Pro
65                  70                  75                  80

Pro Glu Pro Lys Gln Pro Trp Ser Gly Val Val Asp Ala Thr Thr Phe
                85                  90                  95

Gln Ser Val Cys Tyr Gln Tyr Val Asp Thr Leu Tyr Pro Gly Phe Glu
                100                 105                 110

Gly Thr Glu Met Trp Asn Pro Asn Arg Glu Leu Ser Glu Asp Cys Leu
            115                 120                 125

Tyr Leu Asn Val Trp Thr Pro Tyr Pro Arg Pro Thr Ser Pro Thr Pro
130                 135                 140

Val Leu Val Trp Ile Tyr Gly Gly Gly Phe Tyr Ser Gly Ala Ser Ser
145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
                180                 185                 190

Pro Gly Ser Arg Glu Ala Pro Gly Asn Val Gly Leu Leu Asp Gln Arg
            195                 200                 205

Leu Ala Leu Gln Trp Val Gln Glu Asn Val Ala Ala Phe Gly Gly Asp
            210                 215                 220

Pro Thr Ser Val Thr Leu Phe Gly Glu Ser Ala Gly Ala Ala Ser Val
225                 230                 235                 240

Gly Met His Leu Leu Ser Pro Pro Ser Arg Gly Leu Phe His Arg Ala
                245                 250                 255

Val Leu Gln Ser Gly Ala Pro Asn Gly Pro Trp Ala Thr Val Gly Met
                260                 265                 270

Gly Glu Ala Arg Arg Arg Ala Thr Gln Leu Ala His Leu Val Gly Cys
            275                 280                 285

Pro Pro Gly Gly Thr Gly Gly Asn Asp Thr Glu Leu Val Ala Cys Leu
290                 295                 300

Arg Thr Arg Pro Ala Gln Val Leu Val Asn His Glu Trp His Val Leu
305                 310                 315                 320

Pro Gln Glu Ser Val His Arg Phe Ser Phe Val Pro Val Asp Gly
                325                 330                 335

Asp Phe Leu Ser Asp Thr Pro Glu Ala Leu Ile Asn Ala Gly Asp Phe
                340                 345                 350

His Gly Leu Gln Val Leu Val Gly Val Val Lys Asp Glu Gly Ser Tyr
            355                 360                 365

Phe Leu Val Tyr Gly Ala Pro Gly Phe Ser Lys Asp Asn Glu Ser Leu
370                 375                 380
```

```
Ile Ser Arg Ala Glu Phe Leu Ala Gly Val Arg Val Gly Val Pro Gln
385                 390                 395                 400

Val Ser Asp Leu Ala Ala Glu Ala Val Val Leu His Tyr Thr Asp Trp
            405                 410                 415

Leu His Pro Glu Asp Pro Ala Arg Arg Glu Ala Leu Ser Asp Val
        420                 425                 430

Val Gly Asp His Asn Val Val Cys Pro Val Ala Gln Leu Ala Gly Arg
        435                 440                 445

Leu Ala Ala Gln Gly Ala Arg Val Tyr Ala Tyr Val Phe Glu His Arg
    450                 455                 460

Ala Ser Thr Leu Ser Trp Pro Leu Trp Met Gly Val Pro His Gly Tyr
465                 470                 475                 480

Glu Ile Glu Phe Ile Phe Gly Ile Pro Leu Asp Pro Ser Arg Asn Tyr
                485                 490                 495

Thr Ala Glu Glu Lys Ile Phe Ala Gln Arg Leu Met Arg Tyr Trp Ala
            500                 505                 510

Asn Phe Ala Arg Thr Gly Asp Pro Asn Glu Pro Arg Asp Pro Lys Ala
                515                 520                 525

Pro Gln Trp Pro Pro Tyr Thr Ala Gly Ala Gln Gln Tyr Val Ser Leu
    530                 535                 540

Asp Leu Arg Pro Leu Glu Val Arg Arg Gly Leu Arg Ala Gln Ala Cys
545                 550                 555                 560

Ala Phe Trp Asn Arg Phe Leu Pro Lys Leu Leu Ser Ala Thr Asp Thr
                565                 570                 575

Leu Asp Glu Ala Glu Arg Gln Trp Lys Ala Glu Phe His Arg Trp Ser
                580                 585                 590

Ser Tyr Met Val His Trp Lys Asn Gln Phe Asp His Tyr Ser Lys Gln
            595                 600                 605

Asp Arg Cys Ser Asp Leu
    610

(2) INFORMATION FOR SEQ ID NO:22:

(i) SEQUENCE CHARACTERISTICS:
        (A) LENGTH: 614 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:22:

Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Gly Val Gly Ala Glu
            20                  25                  30

Gly Arg Glu Asp Ala Glu Leu Leu Val Thr Val Arg Gly Gly Arg Leu
            35                  40                  45

Arg Gly Ile Arg Leu Lys Thr Pro Gly Gly Pro Val Ser Ala Phe Leu
    50                  55                  60

Gly Ile Pro Phe Ala Glu Pro Pro Met Gly Pro Arg Arg Phe Leu Pro
```

-continued

```
                65                  70                  75                  80
Pro Glu Pro Lys Gln Pro Trp Ser Gly Val Asp Ala Thr Thr Phe
                85                  90                  95
Gln Ser Val Cys Tyr Gln Tyr Val Asp Thr Leu Tyr Pro Gly Phe Glu
            100                 105                 110
Gly Thr Glu Met Trp Asn Pro Asn Arg Glu Leu Ser Glu Asp Cys Leu
            115                 120                 125
Tyr Leu Asn Val Trp Thr Pro Tyr Pro Arg Pro Thr Ser Pro Thr Pro
            130                 135                 140
Val Leu Val Trp Ile Tyr Gly Gly Phe Tyr Ser Gly Ala Ser Ser
145                 150                 155                 160
Leu Asp Val Tyr Asp Gly Arg Phe Leu Val Gln Ala Glu Arg Thr Val
                165                 170                 175
Leu Val Ser Met Asn Tyr Arg Val Gly Ala Phe Gly Phe Leu Ala Leu
                180                 185                 190
Pro Gly Ser Arg Glu Ala Pro Gly Asn Val Gly Leu Leu Asp Gln Arg
                195                 200                 205
Leu Ala Leu Gln Trp Val Gln Glu Asn Val Ala Ala Phe Gly Gly Asp
            210                 215                 220
Pro Thr Ser Val Thr Leu Phe Gly Glu Ser Ala Gly Ala Ala Ser Val
225                 230                 235                 240
Gly Met His Leu Leu Ser Pro Pro Ser Arg Gly Leu Phe His Arg Ala
                245                 250                 255
Val Leu Gln Ser Gly Ala Pro Asn Gly Pro Trp Ala Thr Val Gly Met
                260                 265                 270
Gly Glu Ala Arg Arg Arg Ala Thr Gln Leu Ala His Leu Val Gly Cys
            275                 280                 285
Pro Pro Gly Gly Thr Gly Gly Asn Asp Thr Glu Leu Val Ala Cys Leu
        290                 295                 300
Arg Thr Arg Pro Ala Gln Val Leu Val Asn His Glu Trp His Val Leu
305                 310                 315                 320
Pro Gln Glu Ser Val His Arg Phe Ser Phe Val Pro Val Asp Gly
                325                 330                 335
Asp Phe Leu Ser Asp Thr Pro Glu Ala Leu Ile Asn Ala Gly Asp Phe
            340                 345                 350
His Gly Leu Gln Val Leu Val Gly Val Val Lys Asp Glu Gly Ser Tyr
        355                 360                 365
Asp Leu Val Tyr Gly Ala Pro Gly Phe Ser Lys Asp Asn Glu Ser Leu
        370                 375                 380
Ile Ser Arg Ala Glu Phe Leu Ala Gly Val Arg Val Gly Val Pro Gln
385                 390                 395                 400
Val Ser Asp Leu Ala Ala Glu Ala Val Val Leu His Tyr Thr Asp Trp
                405                 410                 415
Leu His Pro Glu Asp Pro Ala Arg Leu Arg Glu Ala Leu Ser Asp Val
            420                 425                 430
Val Gly Asp His Asn Val Val Cys Pro Val Ala Gln Leu Ala Gly Arg
            435                 440                 445
Leu Ala Ala Gln Gly Ala Arg Val Tyr Ala Tyr Val Phe Glu His Arg
        450                 455                 460
Ala Ser Thr Leu Ser Trp Pro Leu Trp Met Gly Val Pro His Gly Tyr
465                 470                 475                 480
Glu Ile Glu Phe Ile Phe Gly Ile Pro Leu Asp Pro Ser Arg Asn Tyr
                485                 490                 495
```

```
Thr Ala Glu Glu Lys Ile Phe Ala Gln Arg Leu Met Arg Tyr Trp Ala
            500                 505                 510

Asn Phe Ala Arg Thr Gly Asp Pro Asn Glu Pro Arg Asp Pro Lys Ala
            515                 520                 525

Pro Gln Trp Pro Pro Tyr Thr Ala Gly Ala Gln Gln Tyr Val Ser Leu
            530                 535                 540

Asp Leu Arg Pro Leu Glu Val Arg Arg Gly Leu Arg Ala Gln Ala Cys
545                 550                 555                 560

Ala Phe Trp Asn Arg Phe Leu Pro Lys Leu Leu Ser Ala Thr Asp Thr
                565                 570                 575

Leu Asp Glu Ala Glu Arg Gln Trp Lys Ala Glu Phe His Arg Trp Ser
            580                 585                 590

Ser Tyr Met Val His Trp Lys Asn Gln Phe Asp His Tyr Ser Lys Gln
            595                 600                 605

Asp Arg Cys Ser Asp Leu
            610
```

(2) INFORMATION FOR SEQ ID NO:23:

(i) SEQUENCE CHARACTERISTICS:
        (A) LENGTH: 614 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:23:

```
Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Gly Val Gly Ala Glu
            20                  25                  30

Gly Arg Glu Asp Ala Glu Leu Leu Val Thr Val Arg Gly Gly Arg Leu
            35                  40                  45

Arg Gly Ile Arg Leu Lys Thr Pro Gly Gly Pro Val Ser Ala Phe Leu
50                  55                  60

Gly Ile Pro Phe Ala Glu Pro Pro Met Gly Pro Arg Arg Phe Leu Pro
65                  70                  75                  80

Pro Glu Pro Lys Gln Pro Trp Ser Gly Val Val Asp Ala Thr Thr Phe
            85                  90                  95

Gln Ser Val Cys Tyr Gln Tyr Val Asp Thr Leu Tyr Pro Gly Phe Glu
            100                 105                 110

Gly Thr Glu Met Trp Asn Pro Asn Arg Glu Leu Ser Glu Asp Cys Leu
            115                 120                 125

Tyr Leu Asn Val Trp Thr Pro Tyr Pro Arg Pro Thr Ser Pro Thr Pro
            130                 135                 140

Val Leu Val Trp Ile Tyr Gly Gly Gly Phe Tyr Ser Gly Ala Ser Ser
145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
```

-continued

```
                180                 185                 190
Pro Gly Ser Arg Glu Ala Pro Gly Asn Val Gly Leu Leu Asp Gln Arg
            195                 200                 205
Leu Ala Leu Gln Trp Val Gln Glu Asn Val Ala Ala Phe Gly Gly Asp
210                 215                 220
Pro Thr Ser Val Thr Leu Phe Gly Glu Ser Ala Gly Ala Ala Ser Val
225                 230                 235                 240
Gly Met His Leu Leu Ser Pro Ser Arg Gly Leu Phe His Arg Ala
            245                 250                 255
Val Leu Gln Ser Gly Ala Pro Asn Gly Pro Trp Ala Thr Val Gly Met
            260                 265                 270
Gly Glu Ala Arg Arg Arg Ala Thr Gln Leu Ala His Leu Val Gly Cys
            275                 280                 285
Pro Pro Gly Gly Thr Gly Gly Asn Asp Thr Glu Leu Val Ala Cys Leu
290                 295                 300
Arg Thr Arg Pro Ala Gln Val Leu Val Asn His Glu Trp His Val Leu
305                 310                 315                 320
Pro Gln Glu Ser Val His Arg Phe Ser Phe Val Pro Val Asp Gly
            325                 330                 335
Asp Phe Leu Ser Asp Thr Pro Glu Ala Leu Ile Asn Ala Gly Asp Phe
            340                 345                 350
His Gly Leu Gln Val Leu Val Gly Val Val Lys Asp Glu Gly Ser Tyr
            355                 360                 365
Glu Leu Val Tyr Gly Ala Pro Gly Phe Ser Lys Asp Asn Glu Ser Leu
            370                 375                 380
Ile Ser Arg Ala Glu Phe Leu Ala Gly Val Arg Val Gly Val Pro Gln
385                 390                 395                 400
Val Ser Asp Leu Ala Ala Glu Ala Val Val Leu His Tyr Thr Asp Trp
            405                 410                 415
Leu His Pro Glu Asp Pro Ala Arg Leu Arg Glu Ala Leu Ser Asp Val
            420                 425                 430
Val Gly Asp His Asn Val Val Cys Pro Val Ala Gln Leu Ala Gly Arg
            435                 440                 445
Leu Ala Ala Gln Gly Ala Arg Val Tyr Ala Tyr Val Phe Glu His Arg
450                 455                 460
Ala Ser Thr Leu Ser Trp Pro Leu Trp Met Gly Val Pro His Gly Tyr
465                 470                 475                 480
Glu Ile Glu Phe Ile Phe Gly Ile Pro Leu Asp Pro Ser Arg Asn Tyr
            485                 490                 495
Thr Ala Glu Glu Lys Ile Phe Ala Gln Arg Leu Met Arg Tyr Trp Ala
            500                 505                 510
Asn Phe Ala Arg Thr Gly Asp Pro Asn Glu Pro Arg Asp Pro Lys Ala
            515                 520                 525
Pro Gln Trp Pro Pro Tyr Thr Ala Gly Ala Gln Gln Tyr Val Ser Leu
530                 535                 540
Asp Leu Arg Pro Leu Glu Val Arg Arg Gly Leu Arg Ala Gln Ala Cys
545                 550                 555                 560
Ala Phe Trp Asn Arg Phe Leu Pro Lys Leu Leu Ser Ala Thr Asp Thr
            565                 570                 575
Leu Asp Glu Ala Glu Arg Gln Trp Lys Ala Glu Phe His Arg Trp Ser
            580                 585                 590
Ser Tyr Met Val His Trp Lys Asn Gln Phe Asp His Tyr Ser Lys Gln
            595                 600                 605
```

Asp Arg Cys Ser Asp Leu
    610

(2) INFORMATION FOR SEQ ID NO:24:

(i) SEQUENCE CHARACTERISTICS:
        (A) LENGTH: 602 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:24:

Met His Ser Lys Val Thr Ile Ile Cys Ile Arg Phe Leu Phe Trp Phe
1               5                  10                  15

Leu Leu Leu Cys Met Leu Ile Gly Lys Ser His Thr Glu Asp Asp Ile
            20                  25                  30

Ile Ile Ala Thr Lys Asn Gly Lys Val Arg Gly Met Asn Leu Thr Val
        35                  40                  45

Phe Gly Gly Thr Val Thr Ala Phe Leu Gly Ile Pro Tyr Ala Gln Pro
    50                  55                  60

Pro Leu Gly Arg Leu Arg Phe Lys Lys Pro Gln Ser Leu Thr Lys Trp
65                  70                  75                  80

Ser Asp Ile Trp Asn Ala Thr Lys Tyr Ala Asn Ser Cys Cys Gln Asn
                85                  90                  95

Ile Asp Gln Ser Phe Pro Gly Phe His Gly Ser Glu Met Trp Asn Pro
            100                 105                 110

Asn Thr Asp Leu Ser Glu Asp Cys Leu Tyr Leu Asn Val Trp Ile Pro
        115                 120                 125

Ala Pro Lys Pro Lys Asn Ala Thr Val Leu Ile Trp Ile Tyr Gly Gly
    130                 135                 140

Gly Phe Gln Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
                165                 170                 175

Gly Ala Leu Gly Phe Leu Ala Leu Pro Gly Asn Pro Glu Ala Pro Gly
            180                 185                 190

Asn Met Gly Leu Phe Asp Gln Gln Leu Ala Leu Gln Trp Val Gln Lys
        195                 200                 205

Asn Ile Ala Ala Phe Gly Gly Asn Pro Lys Ser Val Thr Leu Phe Gly
    210                 215                 220

Glu Ser Ala Gly Ala Ala Ser Val Ser Leu His Leu Leu Ser Pro Gly
225                 230                 235                 240

Ser His Ser Leu Phe Thr Arg Ala Ile Leu Gln Ser Gly Ser Phe Asn
                245                 250                 255

Ala Pro Trp Ala Val Thr Ser Leu Tyr Glu Ala Arg Asn Arg Thr Leu
            260                 265                 270

Asn Leu Ala Lys Leu Thr Gly Cys Ser Arg Glu Asn Glu Thr Glu Ile
        275                 280                 285

Ile Lys Cys Leu Arg Asn Lys Asp Pro Gln Glu Ile Leu Leu Asn Glu

```
                    290                 295                 300
Ala Phe Val Val Pro Tyr Gly Thr Pro Leu Ser Val Asn Phe Gly Pro
305                 310                 315                 320

Thr Val Asp Gly Asp Phe Leu Thr Asp Met Pro Asp Ile Leu Leu Glu
                325                 330                 335

Leu Gly Gln Phe Lys Lys Thr Gln Ile Leu Val Gly Val Asn Lys Asp
                340                 345                 350

Glu Gly Thr Ala Phe Leu Val Tyr Gly Ala Pro Gly Phe Ser Lys Asp
                355                 360                 365

Asn Asn Ser Ile Ile Thr Arg Lys Glu Phe Gln Glu Gly Leu Lys Ile
                370                 375                 380

Phe Phe Pro Gly Val Ser Glu Phe Gly Lys Glu Ser Ile Leu Phe His
385                 390                 395                 400

Tyr Thr Asp Trp Val Asp Asp Gln Arg Pro Glu Asn Tyr Arg Glu Ala
                405                 410                 415

Leu Gly Asp Val Val Gly Asp Tyr Asn Phe Ile Cys Pro Ala Leu Glu
                420                 425                 430

Phe Thr Lys Lys Phe Ser Glu Trp Gly Asn Asn Ala Phe Phe Tyr Tyr
                435                 440                 445

Phe Glu His Arg Ser Ser Lys Leu Pro Trp Pro Glu Trp Met Gly Val
450                 455                 460

Met His Gly Tyr Glu Ile Glu Phe Val Phe Gly Leu Pro Leu Glu Arg
465                 470                 475                 480

Arg Asp Asn Tyr Thr Lys Ala Glu Glu Ile Leu Ser Arg Ser Ile Val
                485                 490                 495

Lys Arg Trp Ala Asn Phe Ala Lys Tyr Gly Asn Pro Asn Glu Thr Gln
                500                 505                 510

Asn Asn Ser Thr Ser Trp Pro Val Phe Lys Ser Thr Glu Gln Lys Tyr
                515                 520                 525

Leu Thr Leu Asn Thr Glu Ser Thr Arg Ile Met Thr Lys Leu Arg Ala
                530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
                580                 585                 590

Thr Ser Lys Lys Glu Ser Cys Val Gly Leu
                595                 600
```

NFORMATION FOR SEQ ID NO:25:

(i) SEQUENCE CHARACTERISTICS:
        (A) LENGTH: 614 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:25:

-continued

```
Met Arg Pro Pro Gln Cys Leu Leu His Thr Pro Ser Leu Ala Ser Pro
 1               5                  10                  15

Leu Leu Leu Leu Leu Leu Trp Leu Leu Gly Gly Val Gly Ala Glu
             20                  25                  30

Gly Arg Glu Asp Ala Glu Leu Leu Val Thr Val Arg Gly Gly Arg Leu
         35                  40                  45

Arg Gly Ile Arg Leu Lys Thr Pro Gly Gly Pro Val Ser Ala Phe Leu
 50                  55                  60

Gly Ile Pro Phe Ala Glu Pro Pro Met Gly Pro Arg Arg Phe Leu Pro
 65              70                  75                      80

Pro Glu Pro Lys Gln Pro Trp Ser Gly Val Val Asp Ala Thr Thr Phe
                 85                  90                  95

Gln Ser Val Cys Tyr Gln Tyr Val Asp Thr Leu Tyr Pro Gly Phe Glu
                100                 105                 110

Gly Thr Glu Met Trp Asn Pro Asn Arg Glu Leu Ser Glu Asp Cys Leu
            115                 120                 125

Tyr Leu Asn Val Trp Thr Pro Tyr Pro Arg Pro Thr Ser Pro Thr Pro
130                 135                 140

Val Leu Val Trp Ile Tyr Gly Gly Phe His Ser Gly Ala Ser Ser
145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
            180                 185                 190

Pro Gly Ser Arg Glu Ala Pro Gly Asn Val Gly Leu Leu Asp Gln Arg
            195                 200                 205

Leu Ala Leu Gln Trp Val Gln Glu Asn Val Ala Ala Phe Gly Gly Asp
210                 215                 220

Pro Thr Ser Val Thr Leu Phe Gly Glu Ser Ala Gly Ala Ala Ser Val
225                 230                 235                 240

Gly Met His Leu Leu Ser Pro Pro Ser Arg Gly Leu Phe His Arg Ala
            245                 250                 255

Val Leu Gln Ser Gly Ala Pro Asn Gly Pro Trp Ala Thr Val Gly Met
            260                 265                 270

Gly Glu Ala Arg Arg Arg Ala Thr Gln Leu Ala His Leu Val Gly Cys
            275                 280                 285

Pro Pro Gly Gly Thr Gly Gly Asn Asp Thr Glu Leu Val Ala Cys Leu
            290                 295                 300

Arg Thr Arg Pro Ala Gln Val Leu Val Asn His Glu Trp His Val Leu
305                 310                 315                 320

Pro Gln Glu Ser Val Phe Arg Phe Ser Phe Val Pro Val Val Asp Gly
                325                 330                 335

Asp Phe Leu Ser Asp Thr Pro Glu Ala Leu Ile Asn Ala Gly Asp Phe
            340                 345                 350

His Gly Leu Gln Val Leu Val Gly Val Val Lys Asp Glu Gly Ser Tyr
            355                 360                 365

Phe Leu Val Tyr Gly Ala Pro Gly Phe Ser Lys Asp Asn Glu Ser Leu
370                 375                 380

Ile Ser Arg Ala Glu Phe Leu Ala Gly Val Arg Val Gly Val Pro Gln
385                 390                 395                 400

Val Ser Asp Leu Ala Ala Glu Ala Val Val Leu His Tyr Thr Asp Trp
                405                 410                 415

Leu His Pro Glu Asp Pro Ala Arg Leu Arg Glu Ala Leu Ser Asp Val
```

```
                          420                 425                 430
Val Gly Asp His Asn Val Val Cys Pro Val Ala Gln Leu Ala Gly Arg
            435                 440                 445
Leu Ala Ala Gln Gly Ala Arg Val Tyr Ala Tyr Val Phe Glu His Arg
450                 455                 460
Ala Ser Thr Leu Ser Trp Pro Leu Trp Met Gly Val Pro His Gly Tyr
465                 470                 475                 480
Glu Ile Glu Phe Ile Phe Gly Ile Pro Leu Asp Pro Ser Arg Asn Tyr
                485                 490                 495
Thr Ala Glu Glu Lys Ile Phe Ala Gln Arg Leu Met Arg Tyr Trp Ala
            500                 505                 510
Asn Phe Ala Arg Thr Gly Asp Pro Asn Glu Pro Arg Asp Pro Lys Ala
            515                 520                 525
Pro Gln Trp Pro Pro Tyr Thr Ala Gly Ala Gln Gln Tyr Val Ser Leu
            530                 535                 540
Asp Leu Arg Pro Leu Glu Val Arg Arg Gly Leu Arg Ala Gln Ala Cys
545                 550                 555                 560
Ala Phe Trp Asn Arg Phe Leu Pro Lys Leu Leu Ser Ala Thr Asp Thr
                565                 570                 575
Leu Asp Glu Ala Glu Arg Gln Trp Lys Ala Glu Phe His Arg Trp Ser
            580                 585                 590
Ser Tyr Met Val His Trp Lys Asn Gln Phe Asp His Tyr Ser Lys Gln
            595                 600                 605
Asp Arg Cys Ser Asp Leu
            610

(2) INFORMATION FOR SEQ ID NO:26:

(i) SEQUENCE CHARACTERISTICS:
        (A) LENGTH: 454 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:26:

Glu His Cys Leu Tyr Leu Asn Ile Tyr Thr Pro Ala Asp Leu Thr Lys
1               5                   10                  15
Lys Asn Arg Leu Pro Val Met Val Trp Ile His Gly Gly Leu Met
            20                  25                  30
Val Gly Ala Ala Ser Thr Tyr Asp Gly Leu Ala Leu Ala Ala His Glu
            35                  40                  45
Asn Val Val Val Thr Ile Gln Tyr Arg Leu Gly Ile Trp Gly Phe
    50                  55                  60
Phe Ser Thr Gly Asp Glu His Ser Arg Gly Asn Trp Gly His Leu Asp
65                  70                  75                  80
Gln Val Ala Ala Leu Arg Trp Val Gln Asp Asn Ile Ala Ser Phe Gly
                85                  90                  95
Gly Asn Pro Gly Ser Val Thr Ile Phe Gly Glu Ser Ala Gly Gly Glu
            100                 105                 110
```

Ser Val Ser Val Leu Val Leu Ser Pro Leu Ala Lys Asn Leu Phe His
         115                 120                 125

Arg Ala Ile Ser Glu Ser Gly Val Ala Leu Thr Ser Val Leu Val Lys
    130                 135                 140

Lys Gly Asp Val Lys Pro Leu Ala Glu Gln Ile Ala Ile Thr Ala Gly
145                 150                 155                 160

Cys Lys Thr Thr Thr Ser Ala Ala Met Val His Cys Leu Arg Gln Lys
                165                 170                 175

Thr Glu Glu Glu Leu Leu Glu Thr Thr Leu Lys Ile Gly Asn Ser Tyr
            180                 185                 190

Leu Trp Thr Tyr Arg Glu Thr Gln Arg Glu Ser Thr Leu Leu Gly Thr
        195                 200                 205

Val Ile Asp Gly Met Leu Leu Leu Lys Thr Pro Glu Glu Leu Gln Arg
    210                 215                 220

Glu Arg Asn Phe His Thr Val Pro Tyr Met Val Gly Ile Asn Lys Gln
225                 230                 235                 240

Glu Phe Gly Trp Leu Ile Pro Met Gln Leu Met Ser Tyr Pro Leu Ser
                245                 250                 255

Glu Gly Gln Leu Asp Gln Lys Thr Ala Met Ser Leu Leu Gly Ser Pro
            260                 265                 270

Ile Pro Leu Phe Ala Ile Ala Lys Glu Leu Ile Pro Glu Ala Thr Glu
        275                 280                 285

Lys Tyr Leu Gly Gly Thr Asp Asp Thr Val Lys Lys Asp Leu Ile
    290                 295                 300

Leu Asp Leu Ile Ala Asp Val Met Phe Gly Val Pro Ser Val Ile Val
305                 310                 315                 320

Ala Arg Asn His Arg Asp Ala Gly Ala Pro Thr Tyr Met Tyr Glu Phe
                325                 330                 335

Gln Tyr Arg Pro Ser Phe Ser Ser Asp Met Lys Pro Lys Thr Val Ile
            340                 345                 350

Gly Asp His Gly Asp Glu Leu Phe Ser Val Phe Gly Ala Pro Phe Leu
        355                 360                 365

Lys Glu Gly Ala Ser Glu Glu Glu Ile Arg Leu Ser Lys Met Val Met
    370                 375                 380

Lys Phe Trp Ala Asn Phe Ala Arg Asn Gly Asn Pro Asn Gly Lys Gly
385                 390                 395                 400

Leu Pro His Trp Pro Glu Tyr Asn Gln Lys Glu Gly Tyr Leu Gln Ile
                405                 410                 415

Gly Ala Asn Thr Gln Ala Ala Gln Lys Leu Lys Asp Lys Glu Val Ala
            420                 425                 430

Phe Trp Thr Asn Leu Phe Ala Lys Lys Ala Val Glu Lys Pro Pro Gln
        435                 440                 445

Thr Asp His Ile Glu Leu
    450

(2) INFORMATION FOR SEQ ID NO:27:

(i) SEQUENCE CHARACTERISTICS:
        (A) LENGTH: 454 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
    (A) ORGANISM: human esterases (xi) SEQUENCE DESCRIPTION: SEQ ID NO:27:

```
Glu His Cys Leu Tyr Leu Asn Ile Tyr Thr Pro Ala Asp Leu Thr Lys
1               5                   10                  15

Lys Asn Arg Leu Pro Val Met Val Trp Ile His Gly Gly His Leu Met
            20                  25                  30

Val Gly Ala Ala Ser Thr Tyr Asp Gly Leu Ala Leu Ala Ala His Glu
            35                  40                  45

Asn Val Val Val Thr Ile Gln Tyr Arg Leu Gly Ile Trp Gly Phe
50                      55                  60

Phe Ser Thr Gly Asp Glu His Ser Arg Gly Asn Trp Gly His Leu Asp
65                  70                  75                  80

Gln Val Ala Ala Leu Arg Trp Val Gln Asp Asn Ile Ala Ser Phe Gly
                85                  90                  95

Gly Asn Pro Gly Ser Val Thr Ile Phe Gly Glu Ser Ala Gly Gly Glu
            100                 105                 110

Ser Val Ser Val Leu Val Leu Ser Pro Leu Ala Lys Asn Leu Phe His
            115                 120                 125

Arg Ala Ile Ser Glu Ser Gly Val Ala Leu Thr Ser Val Leu Val Lys
130                 135                 140

Lys Gly Asp Val Lys Pro Leu Ala Glu Gln Ile Ala Ile Thr Ala Gly
145                 150                 155                 160

Cys Lys Thr Thr Thr Ser Ala Ala Met Val His Cys Leu Arg Gln Lys
                165                 170                 175

Thr Glu Glu Glu Leu Leu Glu Thr Thr Leu Lys Ile Gly Asn Ser Tyr
            180                 185                 190

Leu Trp Thr Tyr Arg Glu Thr Gln Arg Glu Ser Thr Leu Leu Gly Thr
        195                 200                 205

Val Ile Asp Gly Met Leu Leu Leu Lys Thr Pro Glu Glu Leu Gln Arg
        210                 215                 220

Glu Arg Asn Phe His Thr Val Pro Tyr Met Val Gly Ile Asn Lys Gln
225                 230                 235                 240

Glu Phe Gly Trp Leu Ile Pro Met Gln Leu Met Ser Tyr Pro Leu Ser
            245                 250                 255

Glu Gly Gln Leu Asp Gln Lys Thr Ala Met Ser Leu Leu Gly Ser Pro
            260                 265                 270

Ile Pro Leu Phe Ala Ile Ala Lys Glu Leu Ile Pro Glu Ala Thr Glu
        275                 280                 285

Lys Tyr Leu Gly Gly Thr Asp Asp Thr Val Lys Lys Lys Asp Leu Ile
        290                 295                 300

Leu Asp Leu Ile Ala Asp Val Met Phe Gly Val Pro Ser Val Ile Val
305                 310                 315                 320

Ala Arg Asn His Arg Asp Ala Gly Ala Pro Thr Tyr Met Tyr Glu Phe
                325                 330                 335

Gln Tyr Arg Pro Ser Phe Ser Ser Asp Met Lys Pro Lys Thr Val Ile
            340                 345                 350

Gly Asp His Gly Asp Glu Leu Phe Ser Val Phe Gly Ala Pro Phe Leu
            355                 360                 365

Lys Glu Gly Ala Ser Glu Glu Glu Ile Arg Leu Ser Lys Met Val Met
370                 375                 380
```

```
Lys Phe Trp Ala Asn Phe Ala Arg Asn Gly Asn Pro Asn Gly Lys Gly
385                 390                 395                 400

Leu Pro His Trp Pro Glu Tyr Asn Gln Lys Glu Gly Tyr Leu Gln Ile
            405                 410                 415

Gly Ala Asn Thr Gln Ala Ala Gln Lys Leu Lys Asp Lys Glu Val Ala
            420                 425                 430

Phe Trp Thr Asn Leu Phe Ala Lys Lys Ala Val Glu Lys Pro Pro Gln
            435                 440                 445

Thr Asp His Ile Glu Leu
        450
```

(2) INFORMATION FOR SEQ ID NO:28:

(i) SEQUENCE CHARACTERISTICS:
        (A) LENGTH: 454 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:28:

```
Glu His Cys Leu Tyr Leu Asn Ile Tyr Thr Pro Ala Asp Leu Thr Lys
1               5                   10                  15

Lys Asn Arg Leu Pro Val Met Val Trp Ile His Gly Gly His Leu Glu
            20                  25                  30

Val Gly Ala Ala Ser Thr Tyr Asp Gly Leu Ala Leu Ala Ala His Glu
            35                  40                  45

Asn Val Val Val Thr Ile Gln Tyr Arg Leu Gly Ile Trp Gly Phe
    50                  55                  60

Phe Ser Thr Gly Asp Glu His Ser Arg Gly Asn Trp Gly His Leu Asp
65                  70                  75                  80

Gln Val Ala Ala Leu Arg Trp Val Gln Asp Asn Ile Ala Ser Phe Gly
                85                  90                  95

Gly Asn Pro Gly Ser Val Thr Ile Phe Gly Glu Ser Ala Gly Gly Glu
            100                 105                 110

Ser Val Ser Val Leu Val Leu Ser Pro Leu Ala Lys Asn Leu Phe His
            115                 120                 125

Arg Ala Ile Ser Glu Ser Gly Val Ala Leu Thr Ser Val Leu Val Lys
            130                 135                 140

Lys Gly Asp Val Lys Pro Leu Ala Glu Gln Ile Ala Ile Thr Ala Gly
145                 150                 155                 160

Cys Lys Thr Thr Thr Ser Ala Ala Met Val His Cys Leu Arg Gln Lys
            165                 170                 175

Thr Glu Glu Glu Leu Leu Glu Thr Thr Leu Lys Ile Gly Asn Ser Tyr
            180                 185                 190

Leu Trp Thr Tyr Arg Glu Thr Gln Arg Glu Ser Thr Leu Leu Gly Thr
            195                 200                 205

Val Ile Asp Gly Met Leu Leu Leu Lys Thr Pro Glu Glu Leu Gln Arg
            210                 215                 220
```

```
Glu Arg Asn Phe His Thr Val Pro Tyr Met Val Gly Ile Asn Lys Gln
225                 230                 235                 240

Glu Phe Gly Trp Leu Ile Pro Met Gln Leu Met Ser Tyr Pro Leu Ser
                245                 250                 255

Glu Gly Gln Leu Asp Gln Lys Thr Ala Met Ser Leu Leu Gly Ser Pro
            260                 265                 270

Ile Pro Leu Phe Ala Ile Ala Lys Glu Leu Ile Pro Glu Ala Thr Glu
            275                 280                 285

Lys Tyr Leu Gly Gly Thr Asp Asp Thr Val Lys Lys Lys Asp Leu Ile
290                 295                 300

Leu Asp Leu Ile Ala Asp Val Met Phe Gly Val Pro Ser Val Ile Val
305                 310                 315                 320

Ala Arg Asn His Arg Asp Ala Gly Ala Pro Thr Tyr Met Tyr Glu Phe
                325                 330                 335

Gln Tyr Arg Pro Ser Phe Ser Ser Asp Met Lys Pro Lys Thr Val Ile
                340                 345                 350

Gly Asp His Gly Asp Glu Leu Phe Ser Val Phe Gly Ala Pro Phe Leu
                355                 360                 365

Lys Glu Gly Ala Ser Glu Glu Ile Arg Leu Ser Lys Met Val Met
370                 375                 380

Lys Phe Trp Ala Asn Phe Ala Arg Asn Gly Asn Pro Asn Gly Lys Gly
385                 390                 395                 400

Leu Pro His Trp Pro Glu Tyr Asn Gln Lys Glu Gly Tyr Leu Gln Ile
                405                 410                 415

Gly Ala Asn Thr Gln Ala Ala Gln Lys Leu Lys Asp Lys Glu Val Ala
                420                 425                 430

Phe Trp Thr Asn Leu Phe Ala Lys Lys Ala Val Glu Lys Pro Pro Gln
                435                 440                 445

Thr Asp His Ile Glu Leu
            450
```

(2) INFORMATION FOR SEQ ID NO:29:

(i) SEQUENCE CHARACTERISTICS:
      (A) LENGTH: 454 amino acids
      (B) TYPE: amino acid
      (C) STRANDEDNESS: single
      (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
      (A) ORGANISM: human esterases (xi) SEQUENCE DESCRIPTION: SEQ ID NO:29:

```
Glu His Cys Leu Tyr Leu Asn Ile Tyr Thr Pro Ala Asp Leu Thr Lys
1               5                   10                  15

Lys Asn Arg Leu Pro Val Met Val Trp Ile His Gly Gly His Leu Asp
            20                  25                  30

Val Gly Ala Ala Ser Thr Tyr Asp Gly Leu Ala Leu Ala Ala His Glu
            35                  40                  45

Asn Val Val Val Thr Ile Gln Tyr Arg Leu Gly Ile Trp Gly Phe
50                  55                  60

Phe Ser Thr Gly Asp Glu His Ser Arg Gly Asn Trp Gly His Leu Asp
```

```
                65                  70                  75                  80
Gln Val Ala Ala Leu Arg Trp Val Gln Asp Asn Ile Ala Ser Phe Gly
                            85                  90                  95
Gly Asn Pro Gly Ser Val Thr Ile Phe Gly Glu Ser Ala Gly Gly Glu
                100                 105                 110
Ser Val Ser Val Leu Val Leu Ser Pro Leu Ala Lys Asn Leu Phe His
                115                 120                 125
Arg Ala Ile Ser Glu Ser Gly Val Ala Leu Thr Ser Val Leu Val Lys
            130                 135                 140
Lys Gly Asp Val Lys Pro Leu Ala Glu Gln Ile Ala Ile Thr Ala Gly
145                 150                 155                 160
Cys Lys Thr Thr Thr Ser Ala Ala Met Val His Cys Leu Arg Gln Lys
                        165                 170                 175
Thr Glu Glu Glu Leu Leu Glu Thr Thr Leu Lys Ile Gly Asn Ser Tyr
                    180                 185                 190
Leu Trp Thr Tyr Arg Glu Thr Gln Arg Glu Ser Thr Leu Leu Gly Thr
                195                 200                 205
Val Ile Asp Gly Met Leu Leu Leu Lys Thr Pro Glu Glu Leu Gln Arg
            210                 215                 220
Glu Arg Asn Phe His Thr Val Pro Tyr Met Val Gly Ile Asn Lys Gln
225                 230                 235                 240
Glu Phe Gly Trp Leu Ile Pro Met Gln Leu Met Ser Tyr Pro Leu Ser
                        245                 250                 255
Glu Gly Gln Leu Asp Gln Lys Thr Ala Met Ser Leu Leu Gly Ser Pro
                    260                 265                 270
Ile Pro Leu Phe Ala Ile Ala Lys Glu Leu Ile Pro Glu Ala Thr Glu
                275                 280                 285
Lys Tyr Leu Gly Gly Thr Asp Asp Thr Val Lys Lys Lys Asp Leu Ile
            290                 295                 300
Leu Asp Leu Ile Ala Asp Val Met Phe Gly Val Pro Ser Val Ile Val
305                 310                 315                 320
Ala Arg Asn His Arg Asp Ala Gly Ala Pro Thr Tyr Met Tyr Glu Phe
                        325                 330                 335
Gln Tyr Arg Pro Ser Phe Ser Ser Asp Met Lys Pro Lys Thr Val Ile
                    340                 345                 350
Gly Asp His Gly Asp Glu Leu Phe Ser Val Phe Gly Ala Pro Phe Leu
                355                 360                 365
Lys Glu Gly Ala Ser Glu Glu Ile Arg Leu Ser Lys Met Val Met
            370                 375                 380
Lys Phe Trp Ala Asn Phe Ala Arg Asn Gly Asn Pro Asn Gly Lys Gly
385                 390                 395                 400
Leu Pro His Trp Pro Glu Tyr Asn Gln Lys Glu Gly Tyr Leu Gln Ile
                        405                 410                 415
Gly Ala Asn Thr Gln Ala Ala Gln Lys Leu Lys Asp Lys Glu Val Ala
                    420                 425                 430
Phe Trp Thr Asn Leu Phe Ala Lys Lys Ala Val Glu Lys Pro Pro Gln
                435                 440                 445
Thr Asp His Ile Glu Leu
            450

(2) INFORMATION FOR SEQ ID NO:30:

(i) SEQUENCE CHARACTERISTICS:
        (A) LENGTH: 454 amino acids
        (B) TYPE: amino acid
```

-continued (C) STRANDEDNESS: single
(D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
(A) ORGANISM: human esterases (xi) SEQUENCE DESCRIPTION: SEQ ID NO:30:

```
Glu His Cys Leu Tyr Leu Asn Ile Tyr Thr Pro Ala Asp Leu Thr Lys
1               5                   10                  15

Lys Asn Arg Leu Pro Val Met Val Trp Ile His Gly Gly Leu Met
            20                  25                  30

Val Gly Ala Ala Ser Thr Tyr Asp Gly Leu Ala Leu Ala Ala His Glu
        35                  40                  45

Asn Val Val Val Thr Ile Gln Tyr Arg Leu Gly Ile Trp Gly Phe
    50                  55                  60

Phe Ser Thr Gly Asp Glu His Ser Arg Gly Asn Trp Gly His Leu Asp
65                  70                  75                  80

Gln Val Ala Ala Leu Arg Trp Val Gln Asp Asn Ile Ala Ser Phe Gly
                85                  90                  95

Gly Asn Pro Gly Ser Val Thr Ile Phe Gly Glu Ser Ala Gly Gly Glu
            100                 105                 110

Ser Val Ser Val Leu Val Leu Ser Pro Leu Ala Lys Asn Leu Phe His
        115                 120                 125

Arg Ala Ile Ser Glu Ser Gly Val Ala Leu Thr Ser Val Leu Val Lys
    130                 135                 140

Lys Gly Asp Val Lys Pro Leu Ala Glu Gln Ile Ala Ile Thr Ala Gly
145                 150                 155                 160

Cys Lys Thr Thr Thr Ser Ala Ala Met Val His Cys Leu Arg Gln Lys
                165                 170                 175

Thr Glu Glu Glu Leu Leu Glu Thr Thr Leu Lys Ile Gly Asn Ser Tyr
            180                 185                 190

Leu Trp Thr Tyr Arg Glu Thr Gln Arg His Ser Thr Leu Leu Gly Thr
        195                 200                 205

Val Ile Asp Gly Met Leu Leu Leu Lys Thr Pro Glu Glu Leu Gln Arg
    210                 215                 220

Glu Arg Asn Phe His Thr Val Pro Tyr Met Val Gly Ile Asn Lys Gln
225                 230                 235                 240

Glu Phe Gly Trp Leu Ile Pro Met Gln Leu Met Ser Tyr Pro Leu Ser
                245                 250                 255

Glu Gly Gln Leu Asp Gln Lys Thr Ala Met Ser Leu Leu Gly Ser Pro
            260                 265                 270

Ile Pro Leu Phe Ala Ile Ala Lys Glu Leu Ile Pro Glu Ala Thr Glu
        275                 280                 285

Lys Tyr Leu Gly Gly Thr Asp Asp Thr Val Lys Lys Lys Asp Leu Ile
    290                 295                 300

Leu Asp Leu Ile Ala Asp Val Met Phe Gly Val Pro Ser Val Ile Val
305                 310                 315                 320

Ala Arg Asn His Arg Asp Ala Gly Ala Pro Thr Tyr Met Tyr Glu Phe
                325                 330                 335

Gln Tyr Arg Pro Ser Phe Ser Ser Asp Met Lys Pro Lys Thr Val Ile
```

```
            340                 345                 350
Gly Asp His Gly Asp Glu Leu Phe Ser Val Phe Gly Ala Pro Phe Leu
            355                 360                 365

Lys Glu Gly Ala Ser Glu Glu Ile Arg Leu Ser Lys Met Val Met
370                 375                 380

Lys Phe Trp Ala Asn Phe Ala Arg Asn Gly Asn Pro Asn Gly Lys Gly
385                 390                 395                 400

Leu Pro His Trp Pro Glu Tyr Asn Gln Lys Glu Gly Tyr Leu Gln Ile
                405                 410                 415

Gly Ala Asn Thr Gln Ala Ala Gln Lys Leu Lys Asp Lys Glu Val Ala
                420                 425                 430

Phe Trp Thr Asn Leu Phe Ala Lys Lys Ala Val Glu Lys Pro Pro Gln
                435                 440                 445

Thr Asp His Ile Glu Leu
    450

(2) INFORMATION FOR SEQ ID NO:31:

(i) SEQUENCE CHARACTERISTICS:
        (A) LENGTH: 454 amino acids
        (B) TYPE: amino acid
        (C) STRANDEDNESS: single
        (D) TOPOLOGY: unknown (ii) MOLECULE TYPE: protein (iii) HYPOTHETICAL: YES (iv) ANTI-SENSE: YES (v) FRAGMENT TYPE: N-terminal (vi) ORIGINAL SOURCE:
        (A) ORGANISM: human esterases (xi) SEQUENCE DESCRIPTION: SEQ ID NO:31:

Glu His Cys Leu Tyr Leu Asn Ile Tyr Thr Pro Ala Asp Leu Thr Lys
1               5                   10                  15

Lys Asn Arg Leu Pro Val Met Val Trp Ile His Gly Gly Leu Met
                20                  25                  30

Val Gly Ala Ala Ser Thr Tyr Asp Gly Leu Ala Leu Ala Ala His Glu
            35                  40                  45

Asn Val Val Val Thr Ile Gln Tyr Arg Leu Gly Ile Trp Gly Phe
        50                  55                  60

Phe Ser Thr Gly Asp Glu His Ser Arg Gly Asn Trp Gly His Leu Asp
65                  70                  75                  80

Gln Val Ala Ala Leu Arg Trp Val Gln Asp Asn Ile Ala Ser Phe Gly
                85                  90                  95

Gly Asn Pro Gly Ser Val Thr Ile Phe Gly Glu Ser Ala Gly Gly Glu
                100                 105                 110

Ser Val Ser Val Leu Val Leu Ser Pro Leu Ala Lys Asn Leu Phe His
            115                 120                 125

Arg Ala Ile Ser Glu Ser Gly Val Ala Leu Thr Ser Val Leu Val Lys
        130                 135                 140

Lys Gly Asp Val Lys Pro Leu Ala Glu Gln Ile Ala Ile Thr Ala Gly
145                 150                 155                 160

Cys Lys Thr Thr Thr Ser Ala Ala Met Val His Cys Leu Arg Gln Lys
                165                 170                 175

Thr Glu Glu Glu Leu Leu Glu Thr Thr Leu Lys Ile Gly Asn Ser Tyr
                180                 185                 190
```

```
Leu Trp Thr Tyr Arg Glu Thr Gln Arg Glu Ser His Leu Leu Gly Thr
        195             200             205

Val Ile Asp Gly Met Leu Leu Leu Lys Thr Pro Glu Glu Leu Gln Arg
        210             215             220

Glu Arg Asn Phe His Thr Val Pro Tyr Met Val Gly Ile Asn Lys Gln
225             230             235             240

Glu Phe Gly Trp Leu Ile Pro Met Gln Leu Met Ser Tyr Pro Leu Ser
                245             250             255

Glu Gly Gln Leu Asp Gln Lys Thr Ala Met Ser Leu Leu Gly Ser Pro
                260             265             270

Ile Pro Leu Phe Ala Ile Ala Lys Glu Leu Ile Pro Glu Ala Thr Glu
        275             280             285

Lys Tyr Leu Gly Gly Thr Asp Asp Thr Val Lys Lys Lys Asp Leu Ile
        290             295             300

Leu Asp Leu Ile Ala Asp Val Met Phe Gly Val Pro Ser Val Ile Val
305             310             315             320

Ala Arg Asn His Arg Asp Ala Gly Ala Pro Thr Tyr Met Tyr Glu Phe
                325             330             335

Gln Tyr Arg Pro Ser Phe Ser Ser Asp Met Lys Pro Lys Thr Val Ile
            340             345             350

Gly Asp His Gly Asp Glu Leu Phe Ser Val Phe Gly Ala Pro Phe Leu
            355             360             365

Lys Glu Gly Ala Ser Glu Glu Glu Ile Arg Leu Ser Lys Met Val Met
        370             375             380

Lys Phe Trp Ala Asn Phe Ala Arg Asn Gly Asn Pro Asn Gly Lys Gly
385             390             395             400

Leu Pro His Trp Pro Glu Tyr Asn Gln Lys Glu Gly Tyr Leu Gln Ile
                405             410             415

Gly Ala Asn Thr Gln Ala Ala Gln Lys Leu Lys Asp Lys Glu Val Ala
            420             425             430

Phe Trp Thr Asn Leu Phe Ala Lys Lys Ala Val Glu Lys Pro Pro Gln
        435             440             445

Thr Asp His Ile Glu Leu
    450
```

We claim:

1. A method of enhancing organophosphate detoxifying capability of an esterase chosen from among human acetylcholinesterases, human butrylcholinesterases or human carboxylesterases comprising substituting a histidine residue for at least one amino acid within 6 Å of an active site serine.

2. A method of claim 1 wherein the histidine substitution is next to the serine.

3. A method of claim 1 wherein the esterase is human acetylcholinesterase or human butrylcholinesterase.

4. A method of claim 1 wherein the esterase is human carboxylesterase.

5. A method of detoxifying an organophosphate comprising the steps of:

(1) modifying an esterase chosen from among acetylcholinesterases, butrylcholinesterases or carboxylesterases to enhance organophosphate-detoxifying capability of said esterase by substituting a histidine residue for at least one amino acid within 6 Å of an active site serine of said esterase, and (2) contacting the organophosphate with at least one of the esterases produced in step (1).

6. A method of claim 5 wherein the esterase is a cholinesterase.

7. A method of claim 6 wherein the esterase is human butyryl cholinesterase.

8. A method of claim 6 wherein the esterase is acetylcholinesterase.

9. A method of claim 5 wherein the esterase is a carboxylesterase.

10. An esterase of the formula:

Met His Ser Lys Val Thr Ile Ile Cys Ile Arg Phe Leu Phe Trp (Seq. #2)
Phe Leu Leu Leu Cys Met Leu Ile Gly Lys Ser His Thr Glu Asp
Asp Ile Ile Ile Ala Thr Lys Asn Gly Lys Val Arg Gly Met Asn
Leu Thr Val Phe Gly Gly Thr Val Thr Ala Phe Leu Gly Ile Pro
Tyr Ala Gln Pro Pro Leu Gly Arg Leu Arg Phe Lys Lys Pro Gln
Ser Leu Thr Lys Trp Ser Asp Ile Trp Asn Ala Thr Lys Tyr Ala
Asn Ser Cys Cys Gln Asn Ile Asp Gln Ser Phe Pro Gly Phe His
Gly Ser Glu Met Trp Asn Pro Asn Thr Asp Leu Ser Glu Asp Cys
Leu Tyr Leu Asn Val Trp Ile Pro Ala Pro Lys Pro Lys Asn Ala
Thr Val Leu Ile Trp Ile Tyr Gly Gly His Phe Gln Thr Gly Thr
Ser Ser Leu His Val Tyr Asp Gly Lys Phe Leu Ala Arg Val Glu
Arg Val Ile Val Val Ser Met Asn Tyr Arg Val Gly Ala Leu Gly
Phe Leu Ala Leu Pro Gly Asn Pro Glu Ala Pro Gly Asn Met Gly
Leu Phe Asp Gln Gln Leu Ala Leu Gln Trp Val Gln Lys Asn Ile
Ala Ala Phe Gly Gly Asn Pro Lys Ser Val Thr Leu Phe Gly Glu
Ser Ala Gly Ala Ala Ser Val Ser Leu His Leu Leu Ser Pro Gly
Ser His Ser Leu Phe Thr Arg Ala Ile Leu Gln Ser Gly Ser Phe
Asn Ala Pro Trp Ala Val Thr Ser Leu Tyr Glu Ala Arg Asn Arg
Thr Leu Asn Leu Ala Lys Leu Thr Gly Cys Ser Arg Glu Asn Glu
Thr Glu Ile Ile Lys Cys Leu Arg Asn Lys Asp Pro Gln Glu Ile
Leu Leu Asn Glu Ala Phe Val Val Pro Tyr Gly Thr Pro Leu Ser
Val Asn Phe Gly Pro Thr Val Asp Gly Asp Phe Leu Thr Asp Met
Pro Asp Ile Leu Leu Glu Leu Gly Gln Phe Lys Lys Thr Gln Ile
Leu Val Gly Val Asn Lys Asp Glu Gly Thr Ala Phe Leu Val Tyr
Gly Ala Pro Gly Phe Ser Lys Asp Asn Asn Ser Ile Ile Thr Arg
Lys Glu Phe Gln Glu Gly Leu Lys Ile Phe Phe Pro Gly Val Ser
Glu Phe Gly Lys Glu Ser Ile Leu Phe His Tyr Thr Asp Trp Val
Asp Asp Gln Arg Pro Glu Asn Tyr Arg Glu Ala Leu Gly Asp Val
Val Gly Asp Tyr Asn Phe Ile Cys Pro Ala Leu Glu Phe Thr Lys
Lys Phe Ser Glu Trp Gly Asn Asn Ala Phe Phe Tyr Tyr Phe Glu
His Arg Ser Ser Lys Leu Pro Trp Pro Glu Trp Met Gly Val Met
His Gly Tyr Glu Ile Glu Phe Val Phe Gly Leu Pro Leu Glu Arg
Arg Asp Asn Tyr Thr Lys Ala Glu Glu Ile Leu Ser Arg Ser Ile
Val Lys Arg Trp Ala Asn Phe Ala Lys Tyr Gly Asn Pro Asn Glu
Thr Gln Asn Asn Ser Thr Ser Trp Pro Val Phe Lys Ser Thr Glu
Gln Lys Tyr Leu Thr Leu Asn Thr Glu Ser Thr Arg Ile Met Thr
Lys Leu Arg Ala Gln Gln Cys Arg Phe Trp Thr Ser Phe Phe Pro
Lys Val Leu Glu Met Thr Gly Asn Ile Asp Glu Ala Glu Trp Glu

-continued

Trp Lys Ala Gly Phe His Arg Trp Asn Asn Tyr Met Met Asp Trp

Lys Asn Gln Phe Asn Asp Tyr Thr Ser Lys Lys Glu Ser Cys Val

Gly Leu.

\* \* \* \* \*